United States Patent [19]

Paradies

[11] Patent Number: 5,112,844
[45] Date of Patent: May 12, 1992

[54] IMIDAZOLE DERIVATIVES AND USE AS ANTI-BACTERIA, ANTI-FUNGAL AND ANTI-VIRAL AGENTS

[75] Inventor: Henrich H. Paradies, Iserlohn, Fed. Rep. of Germany

[73] Assignee: Medice chem.-pharm. Fabrik Putter GmbH & Co. KG, Iserlohn, Fed. Rep. of Germany

[21] Appl. No.: 681,445

[22] Filed: Apr. 3, 1991

Related U.S. Application Data

[60] Continuation of Ser. No. 593,550, Oct. 2, 1990, abandoned, which is a continuation of Ser. No. 434,543, Oct. 30, 1989, abandoned, which is a continuation of Ser. No. 321,499, Mar. 9, 1989, abandoned, which is a division of Ser. No. 82,891, Aug. 6, 1987, Pat. No. 4,877,883.

[30] Foreign Application Priority Data

Aug. 7, 1986 [DE] Fed. Rep. of Germany ....... 3626700

[51] Int. Cl.$^5$ .................. A61K 31/415; C07D 233/54
[52] U.S. Cl. .................. 514/398; 514/396; 548/335; 548/337
[58] Field of Search ............... 514/398, 396; 548/335, 548/337

[56] References Cited

FOREIGN PATENT DOCUMENTS 2706839 8/1978 Fed. Rep. of Germany ...... 548/337

Primary Examiner—Johann Richter
Attorney, Agent, or Firm—Townsend & Townsend

[57] ABSTRACT

The synthesis of quaternary five membered N-n-alkyl-heterocycles, especially of 4-hydroxy-N(1)-n-alkyl-imidazolium, 2,5-substituted N(3)-n-alkyl-thiazolium and substituted N(2) pyrazolium salts are described. The N-surfactants obtained have a very small critical micelle concentration (CMC) of $10^{-5}$–$10^{-7}$ Mol/Liter, and are capable of forming micelles of different sizes and forms depending on the nature of the anions. The N-detergents can be used as pharmaceuticals.

2 Claims, 13 Drawing Sheets

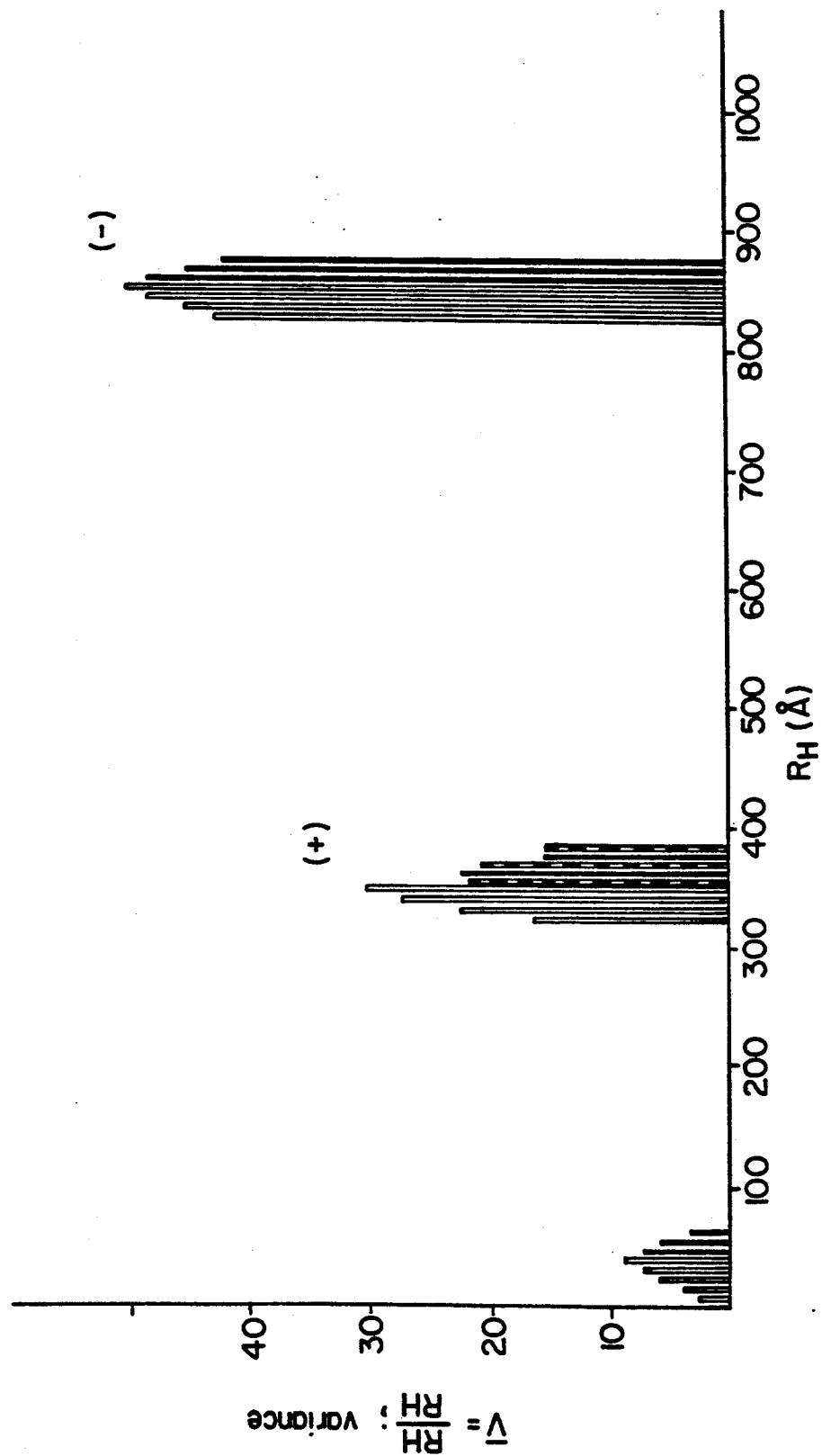
FIG._1.

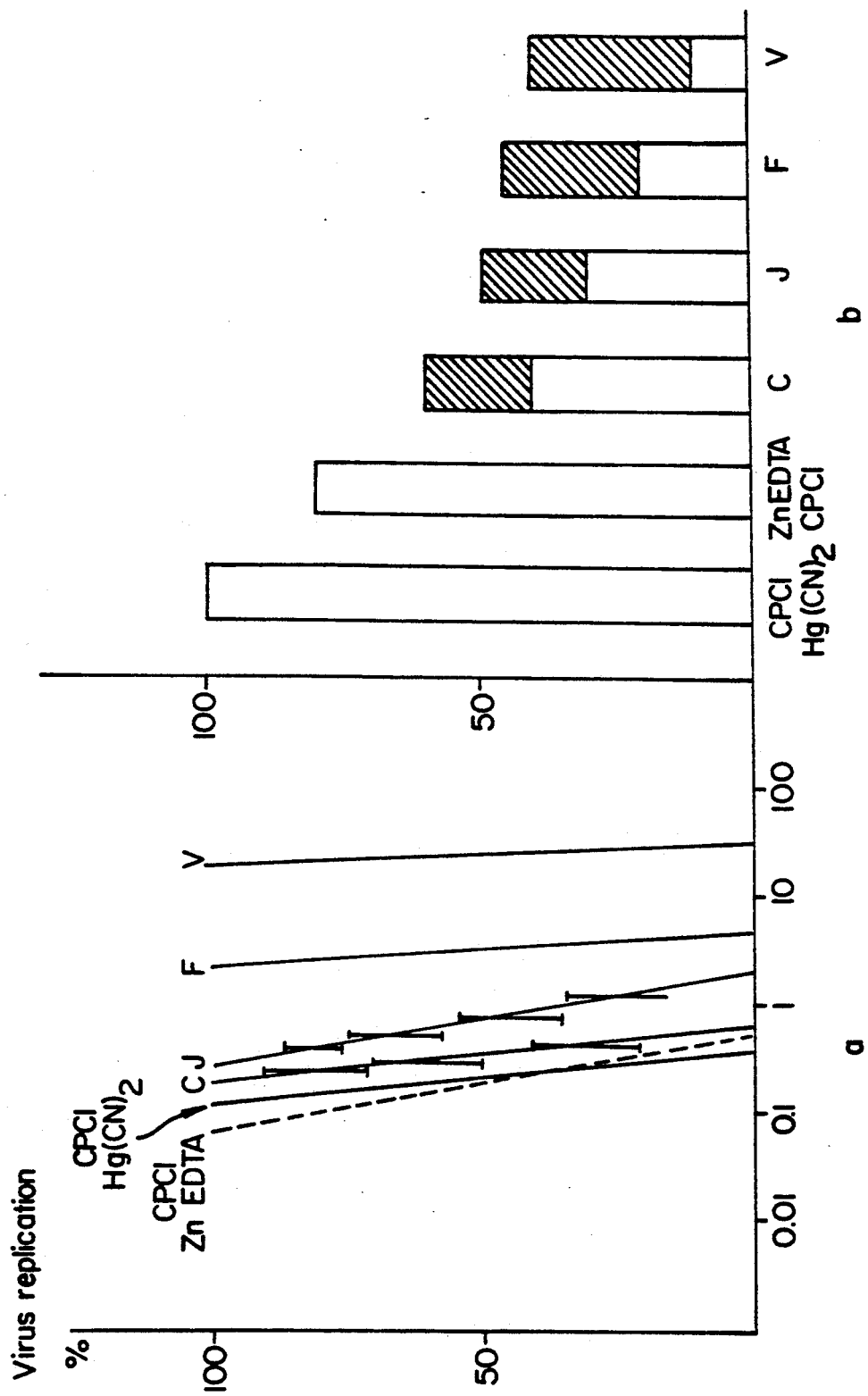
FIG._2.

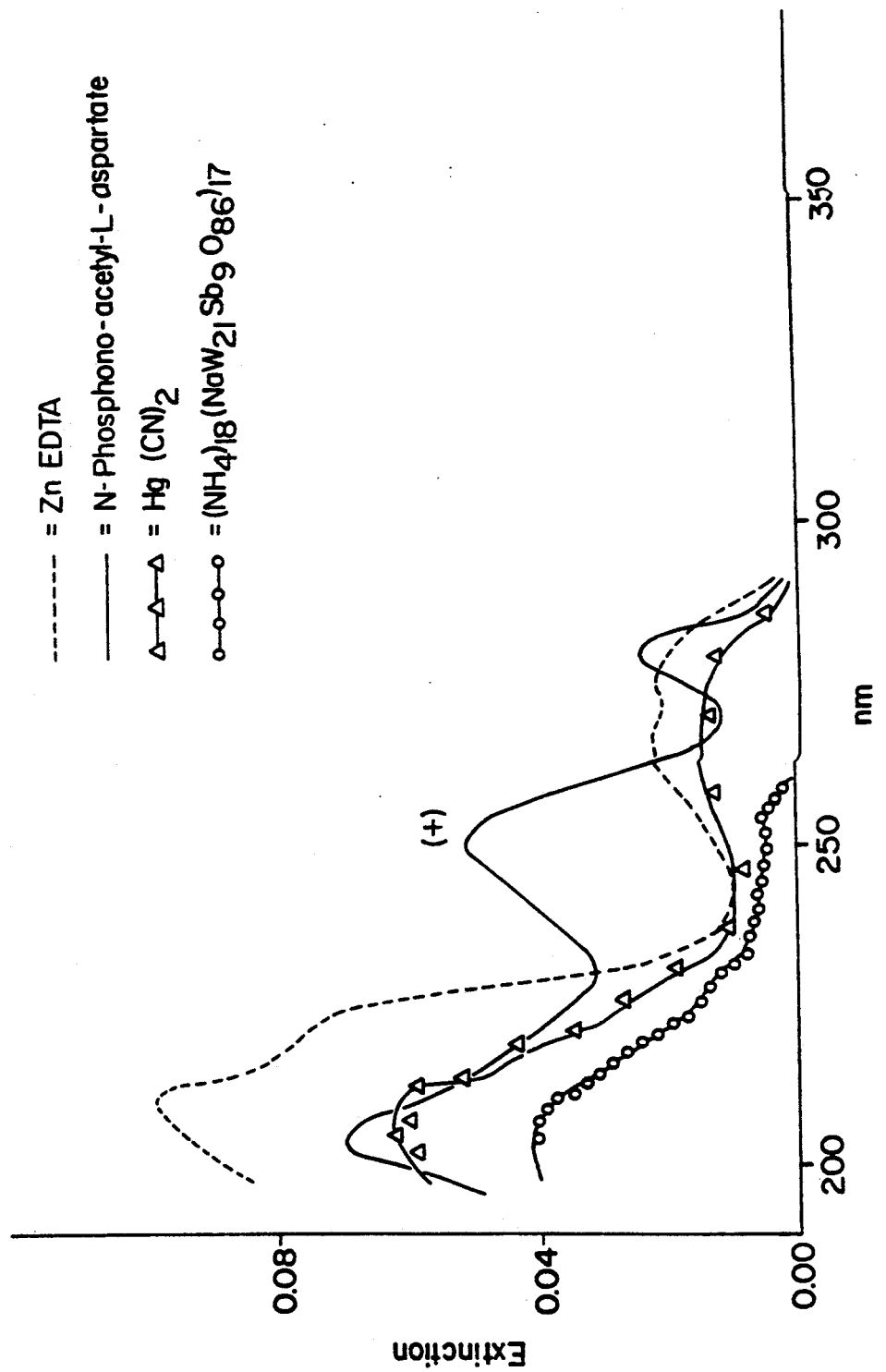

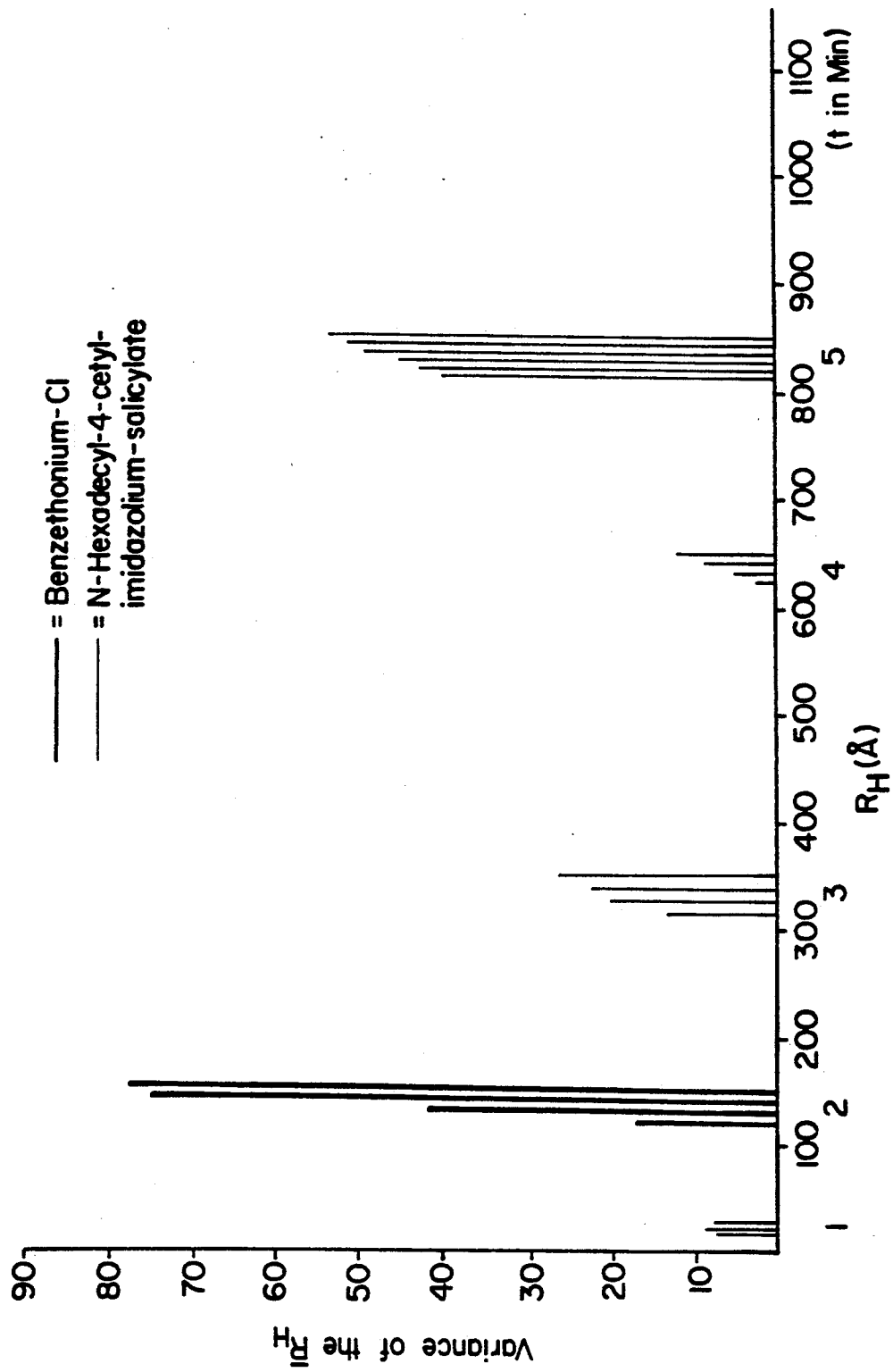
FIG._4.

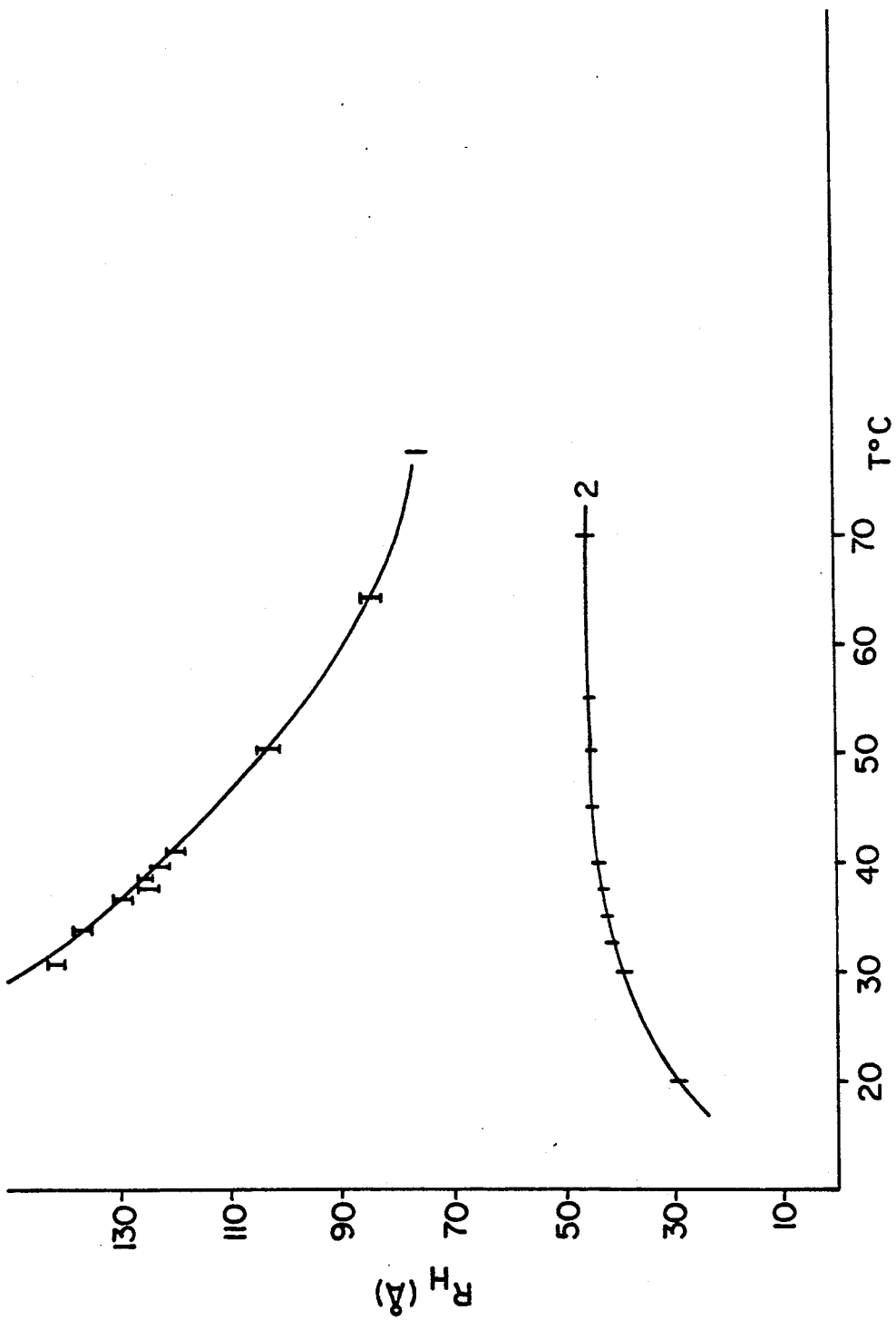
FIG._5.

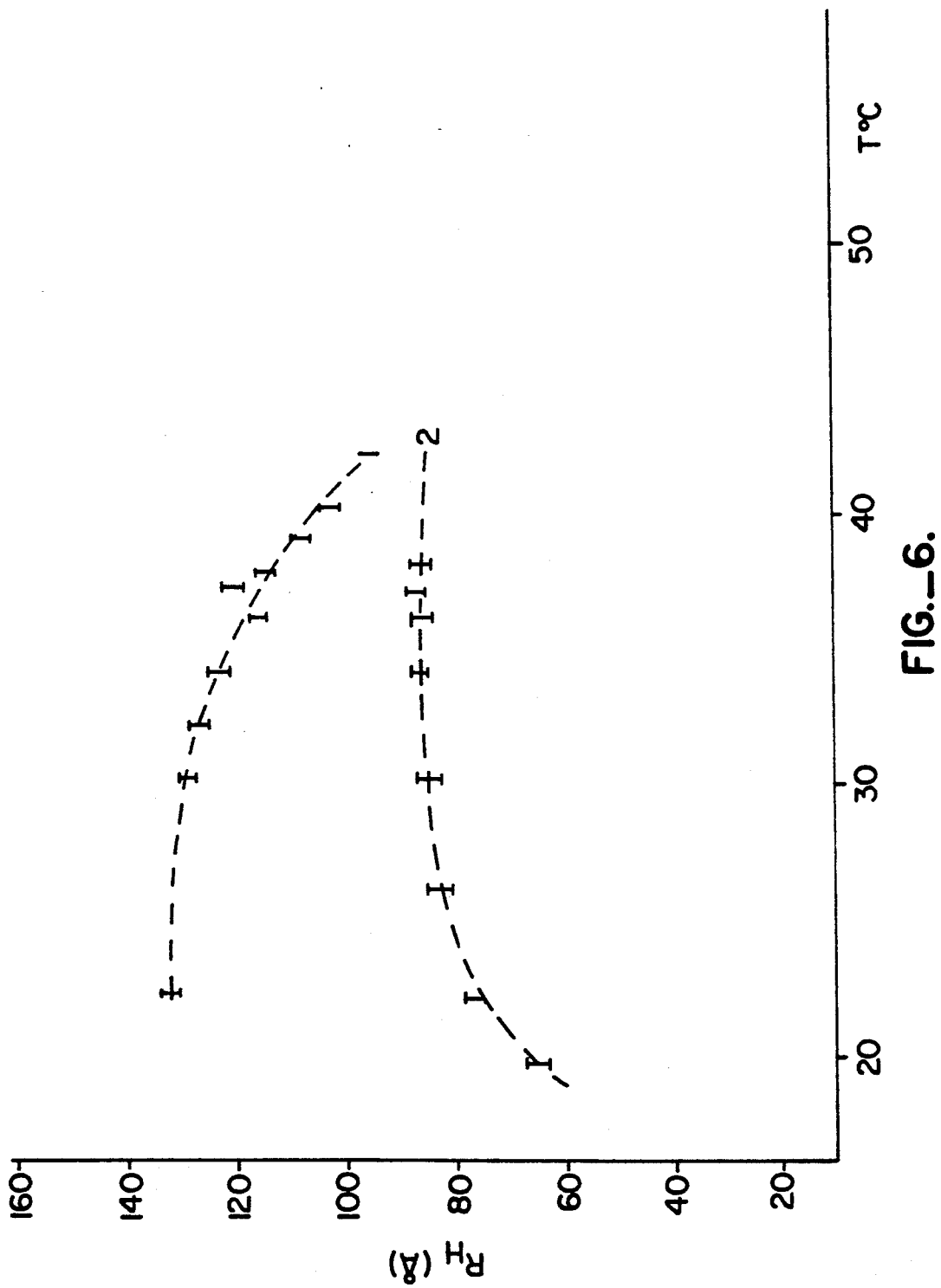
FIG._6.

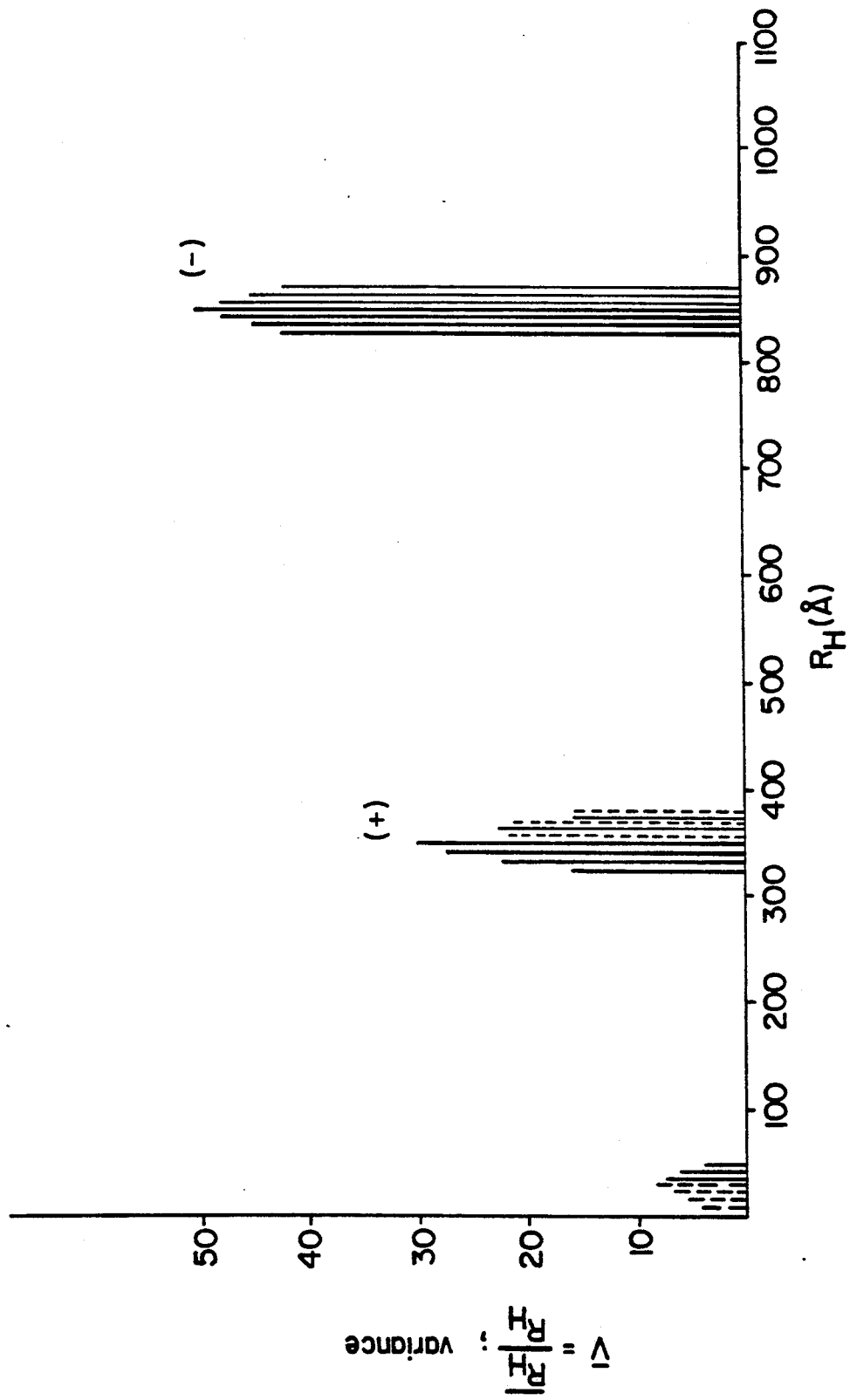
FIG._7.

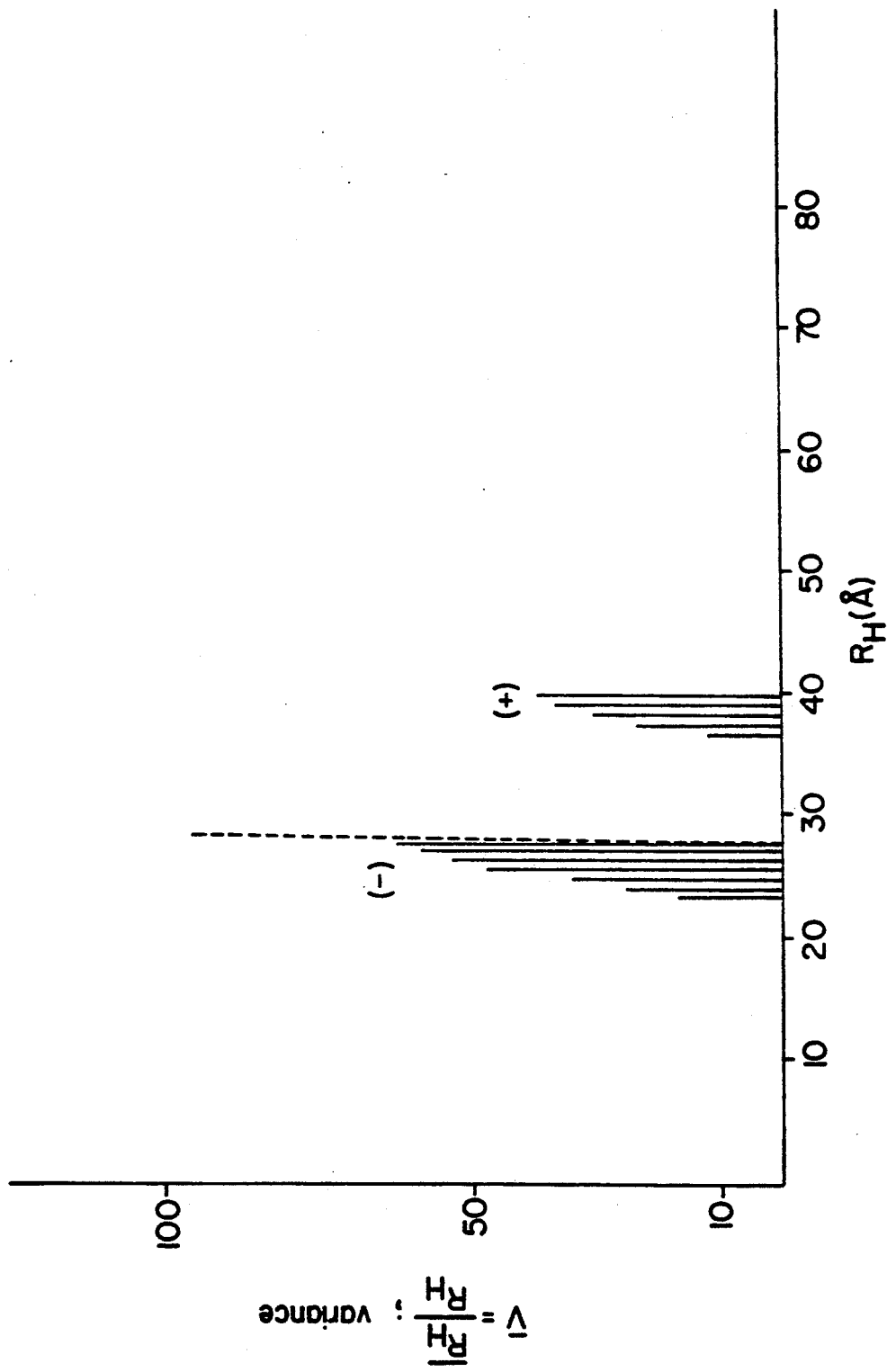
FIG._8.

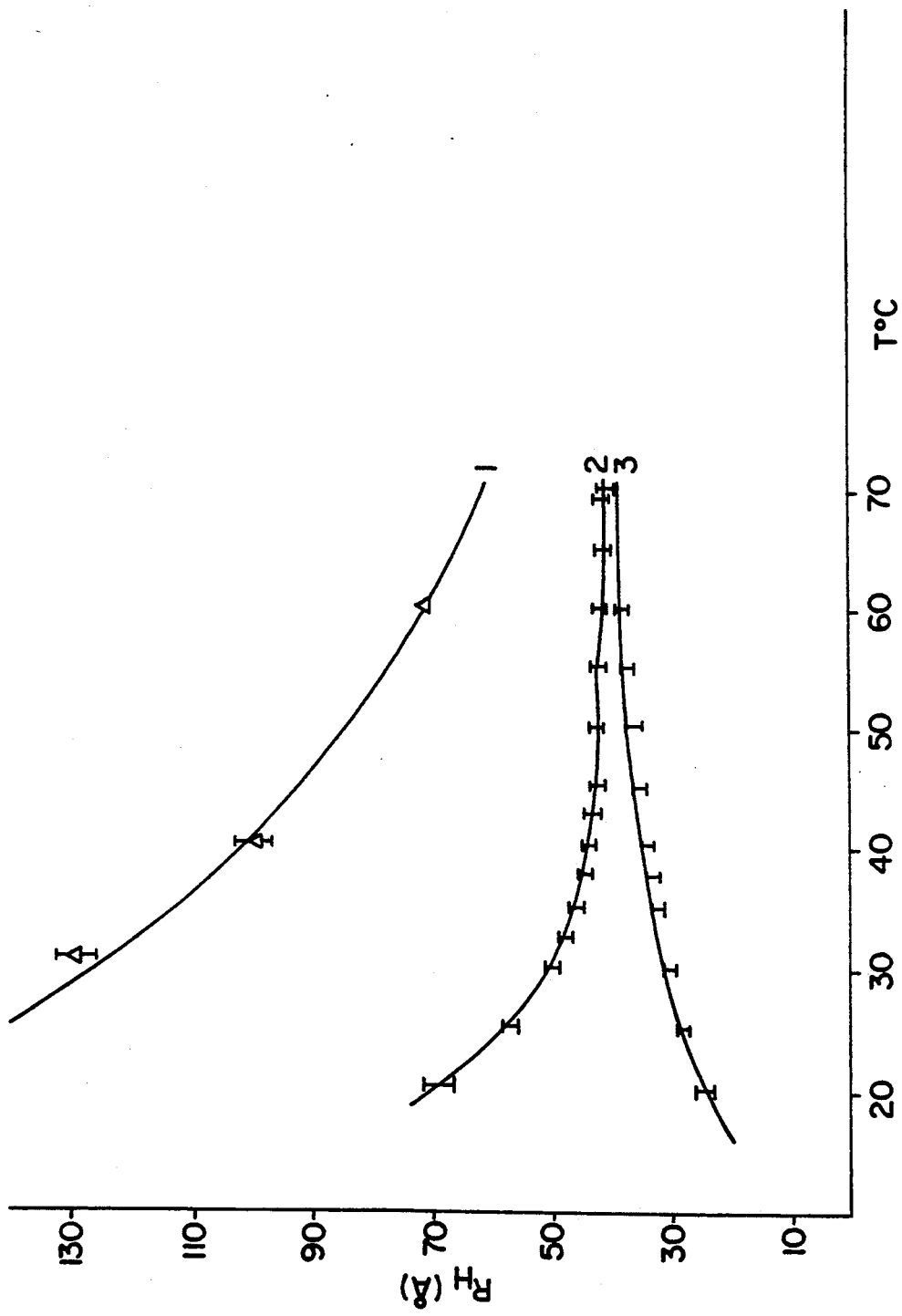
FIG._9.

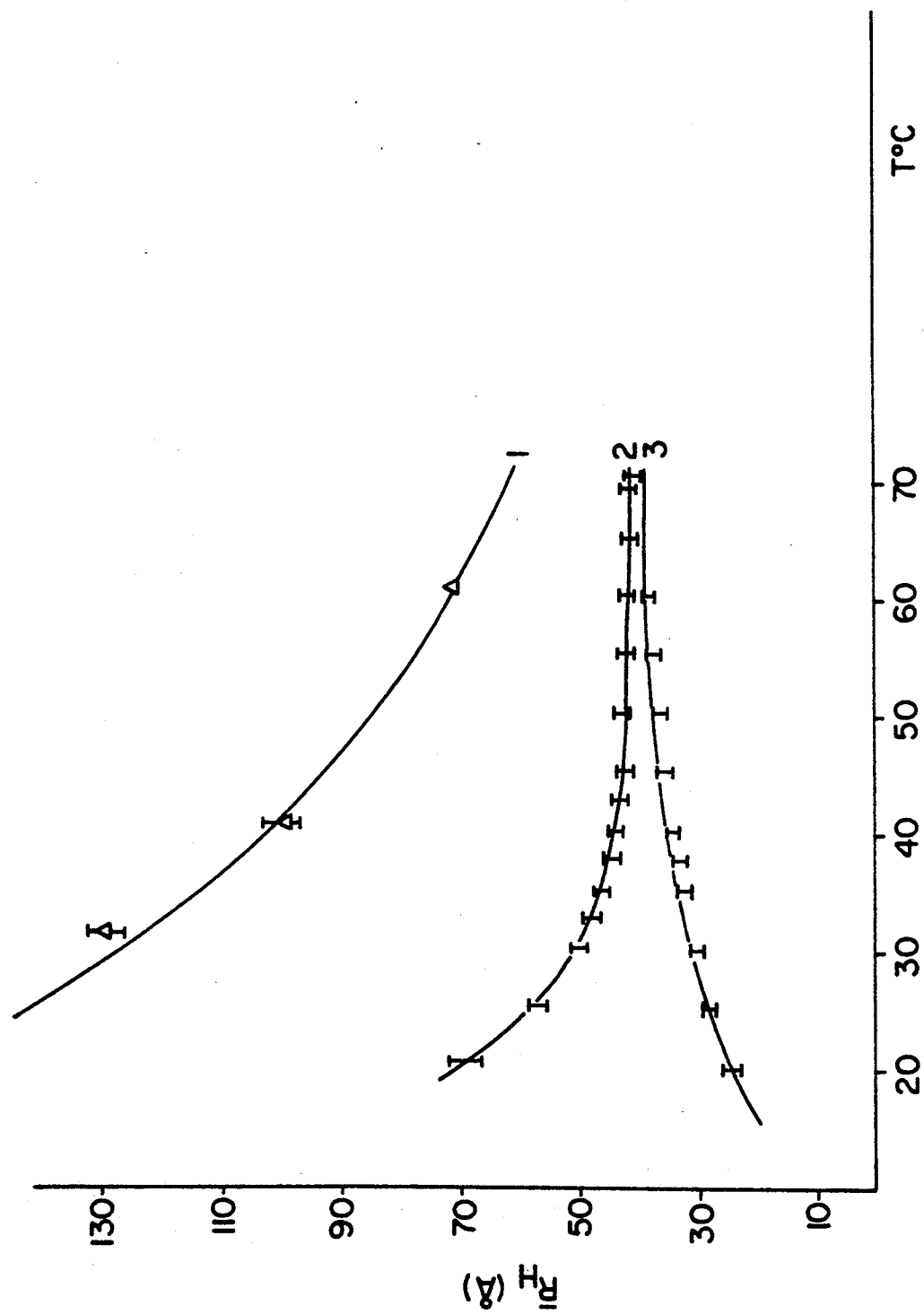
FIG._10.

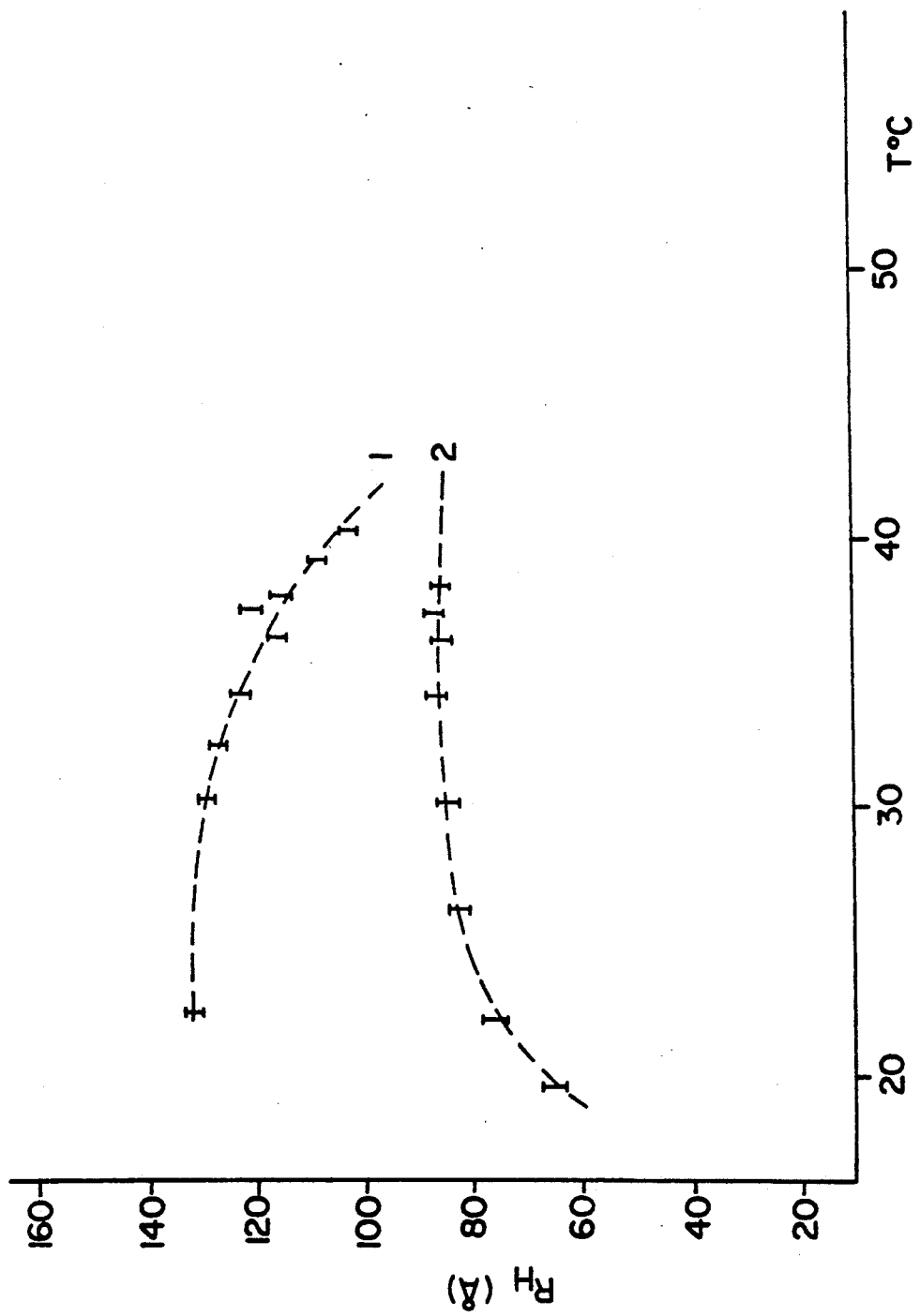
FIG._11.

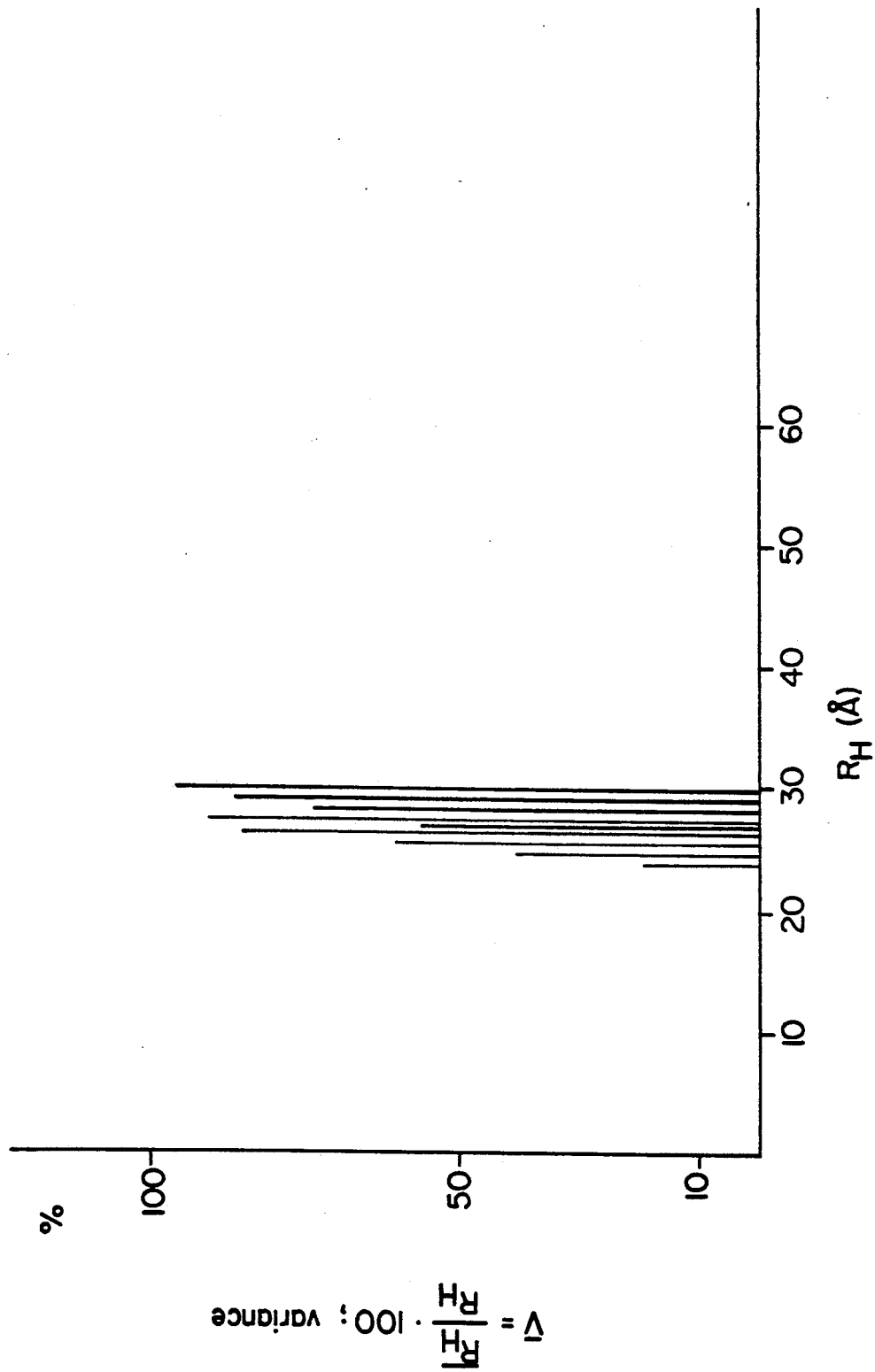
FIG._12.

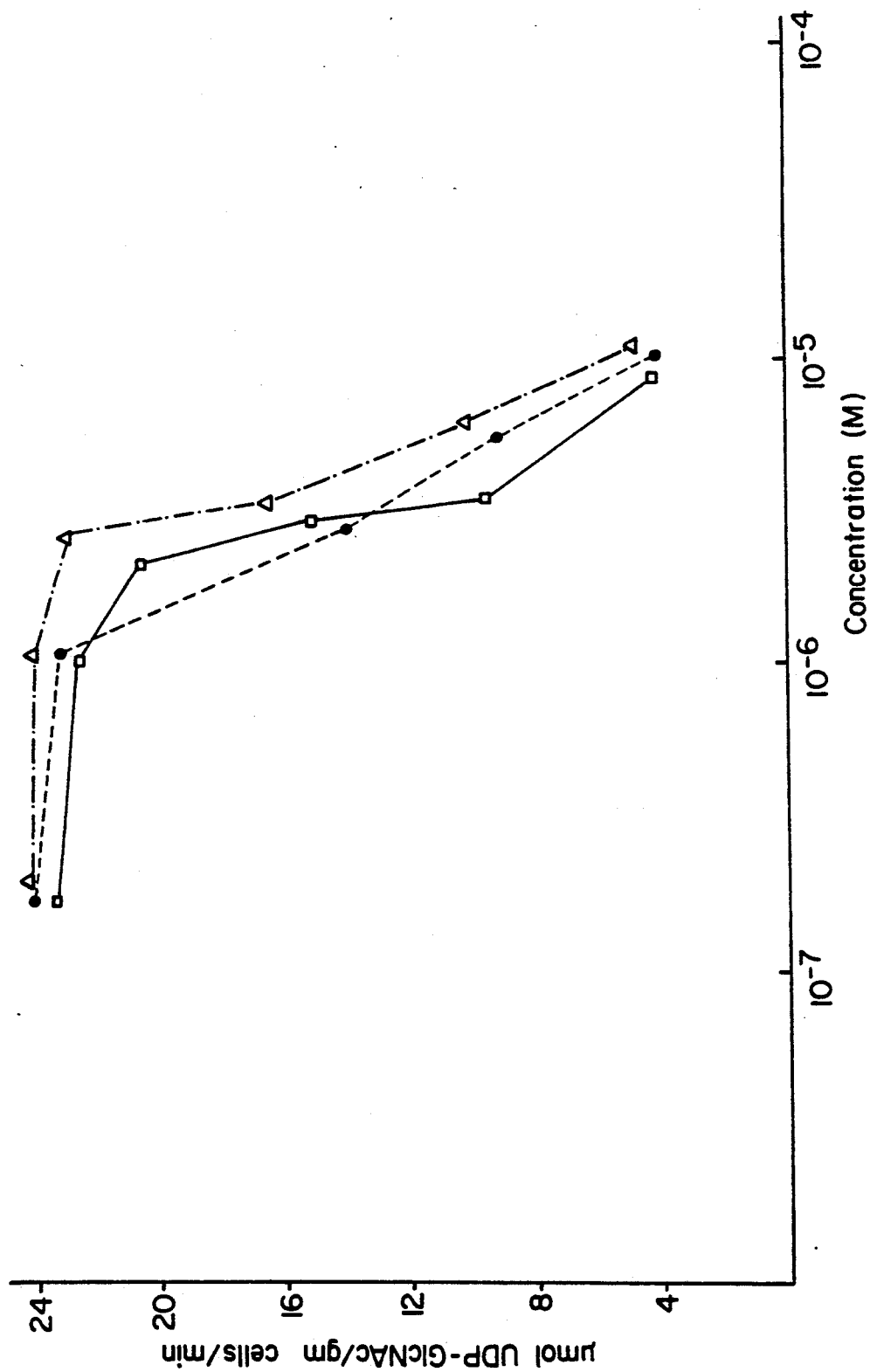
FIG._13.

IMIDAZOLE DERIVATIVES AND USE AS ANTI-BACTERIA, ANTI-FUNGAL AND ANTI-VIRAL AGENTS

This application is a continuation of application Ser. No. 07/593,550, filed Oct. 2, 1990, now abandoned, which is a continuation of Ser. No. 07/434,543, filed Oct. 30, 1989, now abandoned, which is a continuation of Ser. No. 07/321,499, filed on Mar. 9, 1989, now abandoned, which is a divisional of Ser. No. 07/082,891, filed on Aug. 6, 1987, now U.S. Pat. No. 4,877,883.

The present invention relates to pharmaceutical preparations, known cationic tensides as constituents of the pharmaceutical preparation, new chemical compounds (cationic tensides) which are used in particular as constituent of the pharmaceutical preparations, processes for producing the pharmaceutical preparation and processes for producing the known and new chemical compounds (cationic tensides).

STATE OF THE ART AND ITS DISADVANTAGES

Micelles in aqueous solution, both non-ionic, cationic and anionic, have been described in the literature in numerous publications (Mittal, K. L. (1977) Micellization, Solubilization and microemulsions, Plenum Press, New York.—Mittal, K. L. (1979), Solution Chemistry of Surfactants, Plenum Press, New York.—Menger, F. M. (1977). In Bioorganic Chemistry III. Macro- and Multicomponent Systems (E. E. Van Tanelen, Ed.), Academic Press, New York.—Menger, F. M. (1979a) Acc. Chem. Res. 12, 111-117. On the Structures of Micelles.—J. H. Fendler, E. J. Fendler (1975) Catalysis in micellar and macromolecular Systems, Academic Press). Their structure and their galenical, medical and technical use is the subject of numerous investigations. Thus, the antiseptic effect of cetylpyridinium chloride, benzethonium chloride and benzalkonium chloride or their bromides is known. It is also known that in small concentrations they exhibit bactericidal effect in vitro against a large number of grampositive and gramnegative bacteria, the gramnegative reacting substantially more sensitively than the gram-positive. Also, certain gramnegative bacteria are resistant to these quaternary ammonium bases, e.g. *Pseud. cepalia, Mycobact. tuberculosis.*

Normally, cationic micelles in aqueous phase additionally have in their hydrophobic core, which is largely defined by the aliphatic chain and its length, a hydrophobic-hydrophilic boundary layer (Stern layer) which is hydrated and to some extent accommodates the counter ions. The size of this boundary layer is generally between 7-10 Å. They are also surrounded by the Guy-Chapman layer of 10-20 Å containing non-electrostatically bound counter ions, e.g. $Cl^-Br^-$, $HSO_4^-$ and unstructured water. Only the concentrations of the counter ions and other ions effect a reduction of the critical micelle formation concentration (cmc) at constant temperature, pressure and chemical potential, and the nature of the counter ions can govern the form and size of the micelles in aqueous phase. This is done however only by the fraction of counter ions located in the Stern layer in the vicinity of the quaternary nitrogen.

The pure hitherto known cationic quaternary ammonium bases, officially also referred to as invert soaps, have only a limited and non-specific antimicrobial effect (cf. e.g. W. Forth, D. Henschler, W. Rummel. Allgemeine und spezielle Pharmakologie und Toxikologie, 4th edition, B. I. Wissenschaftsverlag, 1983, p. 616). For this reason their use for example as preservatives or disinfectants in the operative fields of medicine or in infection wards (antiseptics) is limited in spite of their low toxicity. Domagk recognised in 1935 (cf. Wallhäussser, K. H.: Sterilisation, Desinfektion, Konservierung, Keimidentifizierung, Betriebshygiene. 2nd edition, Thieme, Stuttgart, 1978) that the quaternary ammonium bases are only bactericidally effective when at least one of the substituents at the nitrogen consists of a linear alkyl chain with 8-18 carbon atoms, the optimum chain length being $C_{12}-C_{16}$. The best known representatives of this substance class are the benzalkonium salts (chlorides and bromides). In addition, hexadecylpyridinium chloride and benzethonium chloride are known and have achieved medical and pharmaceutical significance. The effect of these invert soaps depends of course very greatly on their environment. By soaps for example the effect is largely cancelled as it is also in the acidic pH range. Blood, pus, stools and dirt likewise lead to inactivation. Moreover, they have a protein-precipitating action which starts even at low concentrations of the $N^+$ tensides, i.e. in the range of 1-2% by weight of aqueous solutions. At a concentration of these known tensides amounting to only 2-3 times the critical cmc, although no protein-precipitating effect (denaturing) occurs, a reversible inactivation does take place of enzyme systems and support proteins by unfolding of the active three-dimensional structure ("loss of activity through unfolding").

Also known are the antibacterial and non-specific effect of quaternary ammonium compounds and their surfactant effect, of dequalinium acetate, cetyldimethylammonium bromide (CTAB) and hexadecylpyridinium chloride (CPCl), (cf. e.g. Goodman and Gilman's, The Pharmacological Basis of Therapeutics, EDS. A. G. Goodman, L. S. Goodman, Th. W. Rall, F. Murad, 1985, 7th Edition, Collier, MacMillan Publishing Company, N.Y., p. 971; Merck Index, 1985). The micellar properties of these compounds have been related to their surface activity and antimicrobial properties (cf. Attwood, D, and Florence, A. T., Surfactant Systems, Champan and Hall, London and New York, 1983). However, the non-specific surface activity of these quaternary aliphatic and aromatic ammonium bases cannot be regarded a priori as prerequisite for the antibacterial, antifungal and keratolytic effect because nonionic detergents, e.g. Brij, Triton×100, Lubrol etc. do not become reactive.

Organic quaternary ammonium bases of the type $(R_n, R_1, R_2, R_m, N^+)Y^-$ $(HET=N^+—(CH_2)_x—CH_3)Y^-$ and $[(H_3C)_3.C—CH_2—C(CH_3)_2—X_1—[O-(CH_2)_2)_2—N^+(CH_3)_2—CH_2—X_2]Y^-$ are only partially known, e.g. hexadecyltrimethylammonium chloride and bromide (cetyltrimethylammonium), hexadecylpyridinium chloride or bromide (cetylpyridinium chloride) and N,N'-dimethyl-N-2,2-4-(1,1,3,3-tetrymethylbutyl)phenoxyethylphenylmethanium chloride (benzethonium chloride, methylbenzethonium chloride) and the benzalkonium chlorides with alkyl radicals of $C_8H_{17}$ to $C_{18}H_{37}$. These known $N^+$ tensides all have a small critical micelle formation constant (cmc) in the range of $10^{-4}-10^{-5}$ mol, depending on the environmental conditions such as ionic strength, temperature, pressure and addition of organic solvents of specific dielectric constants. The influence of an anion, $Y^-$, and of fractionated bonds, number of anions at the micelle surface (Stern layer) and their influence on the geometric form of the overall cationic micelle of the aforementioned quaternary organic ammonium bases, have so far been the subject of little investigation. This also applies to the form of the aforementioned tensides in the presence of potentiating mixtures, such as glycerol, dimethyl sulfoxide ethanol, propanol and their stability to temperature and absorptive capacity for hydrophobic (lipophilic) pharmaceutical active substances. Here, no quantifiable investigations are available for the aforementioned $N^+$ tensides either.

Tensides of the general formula (HET=$N^+$—$(CH_2)_x$—$CH_3)Y^-$, the heterocycle being a benzimidazole, pyrimidine, imidazole, thiazole, benzthiazole or purine radical, have so far not been described, and nor has their micellar behaviour in aqueous solutions in the presence and absence of potentiating mixtures. This applies equally to substituted pyridinium compounds which in addition, as will be shown later, can form in aqueous solution vesicles of specific size and form.

The relatively broad and undifferentiated effect mechanism of the already known quaternary organic ammonium bases and the resulting field of use as antiseptics and their toxic action at higher therapeutical doses has restricted the pharmaceutical use of these organic quaternary ammonium bases. Also, for 1% by weight or higher concentrations in aqueous solutions, creams and ointments hypersensitive, allergic and topical irritations have been observed so that specific therapeutical use is possible only to a limited extent.

The bactericidal effect of chlorhexidine is known in the case of grampositive and gramnegative bacteria but gramnegative bacilli are resistant.

Pharmaceutic preparations permitting a more specific therapy with pharmaceutical active substances included in micelles, e.g. of antiviral, antifungal, antineoplastic nature, are not available in therapeutically effective doses and a suitable pharmaceutical preparation (galenic).

A great disadvantage of the hitherto known pharmaceutical preparations of quaternary organic ammonium bases, this applying in the presence of potentiating mixtures as well, is the polydispersity of the colloidal micellar solutions. Depending on the pharmaceutic preparation form, pH value, ionic strength, counter ion $Y^-$ and temperature, hitherto in a pharmaceutical preparation micelles of various form and size and stability and absorptive capacity for pharmaceutical active substances were present.

In the broadest sense micelles are taken to mean aggregates of dissolved molecules formed by association. In the narrower sense mainly used today micelles is a term applied to aggregates which form from tenside molecules in aqueous solutions above a specific temperature (Krafft point) or a characteristic concentration. This concentration is called the critical micellization concentration, cmc. When the cmc is exceeded the monomer concentration remains practically constant and the excess tenside molecules form micelles. They may occur in various shapes (spheres, rods, discs) depending on the chemical constitution of the tenside and on the temperature, concentration or ionic strength of the solution. The micelles have characteristic aggregation numbers with usually only a small distribution spread. Reaching the cmc manifests itself by abrupt changes in the surface tension (which is utilized to measure the cmc), the osmotic pressure, the electrical conductivity and the viscosity.

Micelles are thermodynamic stable association colloids of surfactant substances in which the hydrophobic radicals of the monomers lie in the interior of the aggregates and are held together by hydrophobic interaction nvan-der-Waals forces); the hydrophilic groups face the water and by solvation provide the solubility of the colloid.

Further information on micelles will be found in Römpps Chemielexikon, 8th edition, Franckh'sche Verlagsbuchhandlung Stuttgart, 1985, page 2600 et seq.

An object of the present invention is to provide a pharmaceutical preparation which contains the active substance in the most stable form possible and in which the active substance is liberated at the location of the pathological process as rapidly and completely as possible.

This problem is solved according to the invention by a pharmaceutical preparation which is characterized in that it is made up of a micelle consisting of a cationic tenside with a monovalent anion and a hydrophobic pharmaceutical active substance dispersed in a solvent whose pH value is $\leq 7$, the critical micellization concentration (cmc) lying in the range of $1.0 \cdot 10^{-7}$ to $1.5 \cdot 10^{-4}$ mol/liter.

Preferably, this pharmaceutical preparation is made up of a micelle consisting of a cationic tenside with a monovalent anion in an amount of 0.01 to 0.1% by weight with respect to the total pharmaceutical preparation, and a hydrophobic pharmaceutical active substance in an amount of 0.001 to 0.5% by weight with respect to the total pharmaceutical preparation, dispersed in a solvent whose pH value is $\leq 7.0$, in an amount of 99.40 to 99.989% by weight with respect to the total pharmaceutical preparation, the critical micellization concentration (cmc) lying in the range of $1.0 \cdot 10^{-7}$ to $1.5 \cdot 10^{-4}$ mol/liter.

The micelles described here in aqueous phase have with a hydrophobic chain length of 15-($CH_2$) groups including their quaternary nitrogen in the aromatic structure a diameter of approx. 50–100 Å depending on the nature of the counter ions.

DESCRIPTION AND PREPARATION OF THE QUATERNARY AMMONIUM BASES

The cationic tenside according to the invention is preferably a compound of the general formula

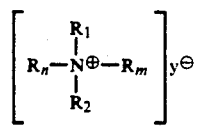

wherein preferably $R_1$ = an alkyl radical with 1–12 C atoms or an aralkyl
$R_2$ = an alkyl radical with 1–12 C atoms or an aralkyl
$R_n$ = a straight-chain or branched alkyl radical, which may be substituted with 1–22, preferably 10–20 C atoms or an alkenyl radical with 8–20 C atoms, preferably 8–10 C atoms or a 5- or 6-member aromatic heterocycle with one or 2 nitrogen atoms and optionally one sulfur atom or one oxygen atom
$R_m$ = a straight-chain or branched alkyl radical, which may be substituted with 1–22, preferably 10–20 C atoms or an alkenyl radical with 8–20 C atoms, preferably 8-10 C atoms or a 5- or 6-member aromatic heterocycle with one or 2 nitrogen atoms and optionally one sulfur atom or one oxygen atom, or a quinolinium radical, and $y^-$ = a monovalent anion.

Further preferred embodiments are:

The straight-chain or branched alkyl are preferred to be those with $C_6-C_{22}$, in particular however $C_{12}-C_{20}$, carbon atoms, for example n-heptyl, 2-methylhexyl, 3-methylhexyl, 3-ethylpentyl, 2,2, 2,3, 2,4, or 3,3-dimethylpentyl, n-octyl, 4-methylheptyl, 2,2,2, 2,2,4, 2,3,3, 2,3,4-trimethylpentyl, n-nonyl, n-decyl, n-undecyl, n-dodecyl, n-tridecyl, n-tetradecyl, n-pentadecyl, n-hexadecyl (cetyl), n-heptadecyl, n-octadecyl, n-nonadecyl or n-eicosyl (arachinyl).

Preferred is a straight-chain alkyl having an even number of 10-20 carbon atoms, e.g. n-dodecyl, n-tetradecyl, n-hexadecyl (cetyl), n-octadecyl or n-eicosyl. They all have the same bonding and absorptive capacity for inorganic and organic (hydrophobic) active substances, for example $Hg(CN)_2$, ZnEDTA, ZnO, and $K_{18}(KW_{21}Sb_9O_{86})_{17}$ as inorganic antiviral active substances, and azathioprine, nystatin, amphotericin, idoxuridine, cytarabine and trifluorothymidine as organic active substances.

Preferred is an alkenyl having 12-20 carbon atoms for $R_n$ if $R_m$ is a methyl, ethyl up to a hexyl radical, specifically alkenyl, having a double bond, such as 9-cis-dodecenyl, 9-cis-tetradecenyl, 9-cis-hexadecenyl, 6-cis-octadecenyl, 6-trans-octadecenyl and 9-cis-octadecenyl.

$R_1$, $R_2$ and $R_m$ is preferred to be methyl, ethyl or also hexyl.

An aromatic heterocycle for $R_n$ of the formula (I) is a 5 or 6-member aromatic heterocycle having one or two nitrogen atoms, and optional a nitrogen and a sulfur atom, e.g. a pyridine, a pyrimidine, a pyrazine (1,4-diazine), a pyrazole, an imidazole, a thiazole and purine radical (7N-imidazolium[4,5-d]pyrimidine) or a benzo-condensed thiazole and imidazole radical, e.g. $N_3$-benzimidazole or benzthiazole.

Substituents of this heterocycle are at the nitrogen atom and possibly at a carbon atom a low alkyl, e.g. methyl or ethyl, or a hydroxy low alkyl, e.g. hydroxymethyl or 2-hydroxyethyl, oxo, hydroxy or halogen, e.g. chlorine or bromine.

A heterocycle is preferably 2 or 4-low alkyl pyridinium, e.g. 2 or 4-methyl or 2 or 4-ethylpyridinium, di-low alkyl pyridinium, e.g. 2,6-dimethyl, 2-methyl-3-ethyl, 2-methyl-4-ethyl, 2-methyl-5-ethyl or 2-methyl-6-ethyl-pyridinium, 2, 3 or 4-halogen pyridinium, e.g. 2, 3 or 4-chloropyridinium or 2, 3 or 4-bromopyridinium, 2-low alkyl imidazolinium, oxazolinium or thiazolinium, e.g. 2-methyl or 2-ethyl imidazolinium, oxazolinium or thiazolinium or 2-low alkyl-8-halogen quinolinium, e.g. 2-methyl-8-chloroquinolinium.

$Y^\ominus$ is an anion, preferably chloride, bromide, iodide or ethyl sulfate, a low alkonate, such as formate acetate, propionate, hydrogen sulfate ($HSO_4-$), malate or fumarate, salicylate, alginate or gluconate.

A cationic tenside of the general formula (I) is preferably N-benzyl-N,N-dimethyl-N-2-[2-(4-(1,1,3,3-tetramethylbutyl)phenoxy)-ethoxy]-ethylammonium chloride, N-benzyl-N,N-dimethyl-N-2[2-(3-methyl-4-(1,1,3,3-tetramethylbutyl)-phenoxy)-ethoxy]ethylammonium chloride (methylbenzethonium chloride), n-dodecyltrimethylammonium chloride or bromide, trimethyl-n-tetradecylammonium chloride or bromide, n-hexadecyltrimethylammonium chloride or bromide (cetyltrimethylammonium chloride or bromide), trimethyl-n-octadecylammonium chloride or bromide, ethyl-n-dodecyldimethylammonium chloride or bromide, ethyldimethyl-n-tetradecylammonium chloride or bromide, ethyl-n-hexadecyldimethylammonium chloride or bromide, ethyldimethyl-n-octadecylammonium chloride or bromide, n-alkyl-benzyldimethylammonium chloride or bromide (benzalkonium chloride or bromide), e.g. benzyl-n-dodecyldimethylammonium chloride or bromide, benzyldimethyl-n-tetradecylammonium chloride or bromide, benzyl-n-hexadecyldimethylammonium chloride or bromide or benzyldimethyl-n-octadecylammonium chloride or bromide, N-(n-decyl)-pyridinium chloride or bromide, N-(n-dodecyl)-pyridinium chloride or bromide, N-(n-tetradecyl)-pyridinium chloride or bromide, N-(n-hexadecyl)-pyridinium chloride or bromide (cetylpyridinium chloride) or N(n-octadecyl)-pyridinium chloride or bromide or a mixture of these tensides.

A cationic tenside of the general formula (I) $R_nN^\oplus(R_1,R_2)R_mY^\ominus$ is preferably with $R_n=R_1=R_2$ e.g. $R_nN^\oplus(CH_3)_3Y^\ominus$ or as substance e.g. n-heptyl-trimethyl-ammonium chloride (bromide), 3-methyl-hexyl-trimethyl-ammonium chloride, n-nonyl-trimethyl-ammonium chloride, n-undecyl-trimethyl-ammonium chloride, n-hexadecyl-trimethyl-ammonium chloride, n-octadecyl or n-eicosyl-trimethyl-ammonium bromide with an even number of 12-20 carbon atoms.

On the basis of a microemulsion and/or ointment e.g. in the presence of up to 10% (g/g) DMSO these N tensides have the same antifungal, antibacterial and keratolytic properties as the non-covalently bound pharmaceutical active substances.

The tensides of the general formula $R_nN^\oplus(R_1,R_2)R_mY^\ominus$ are to be prepared analogously to that described in the standard work "Cationic Surfactants" by E. Jungermann, Dekker, N.Y., 1970, cf. also the handbook which appears each year "McCutcheon's Emulsifiers and Detergents" Manufacturing Confectioner Publishing Co. Other alkyl pyridinium halides can be obtained by reaction of stoichiometric amounts of pyridine derivatives with long-chain alkyl halides in good yield. Other processes proceed from the corresponding ultracyclic N-compounds and 1,3-propane methane, as for example described in F. J. Fendler et al., J. Chem. Soc., Perkin III, 1097 (1977). Other processes leading to similarly good yields are for example described in Attwood, D., Elwarthy, P. H., and Kaye, S. B., J. Phys. Chem. 74, 3529 (1970) and may be used analogously for the synthesis of the substances of formula II. The pharmaceutical active substances are available commercially.

The synthesis of the compounds of the general formula $R_n,R_m,R_1,R_2N^\oplus Y^\ominus$ or $R_n,R_mN^\oplus(CH_3)_2Y^\ominus$ is carried out specifically in accordance with the following procedure:

a) The corresponding alkyl iodide or bromide is allowed to stand with an excess of trimethylamine (halide:amine=1:1.45) for 24 hours at 20° C. in an autoclave for preparing the corresponding quaternary ammonium base. No solvent other than methanol which has been saturated with the trimethylamine or $R_1$, $R_2$ alkylamine was used. The reaction mixture is stirred into 5 times the volume of ether and heated in reflux for 20 min. The solid residue forming after cooling in ether is filtered off. The recrystallization is from chloroform. The crystals are washed repeatedly with anhydrous ether. The recrystallizations until constant melting point were carried out from ethanol/ether (1:1, % g/g) in the presence of activated charcoal. The crystals were dried overnight at 80° C. over calcium chloride under vacuum at 1 mm/Hg.

b) To prepare $R_n,R_m,R_1,R_2N\oplus Y\ominus$ the corresponding amines, $R_1,R_2$-N⊕-amines, were refluxed with the stoichiometric amounts of $R_n,R_m$-iodides in absolute ethanol-hexane (1:2% g/g) for 48 hours. Thereafter the reaction was cooled and the mixture poured into a 5-times excess of ether and filtered off. The recrystallization was carried out as indicated under a).

c) To convert the quaternary ammonium halides to the corresponding bromides, chlorides or also iodides, the following methods are possible:

300 g Amberlite IRA-400 (4 mequiv/g) in the chloride form is introduced into a column (45×5 cm) and with a very slow throughflow time washed with 1 liter of a 20% aqueous solution of potassium chloride or potassium bromide or potassium iodide or $KY\ominus$. The matrix was then washed with deionized water until no reaction occurred to chloride or bromide or iodide.

Thereafter the column matrix was charged with a 10% aqueous solution of a quaternary ammonium bromide. The following elution was carried out with water with a flow rate of 1 ml/min. The corresponding quaternary ammonium bromide or halide was obtained by concentration of the eluate in a rotary evaporator. The recrystallization was carried out as described under a). The following table 4 shows some cationic tensides of the form $R_nN\oplus(CH_3)_3Y\ominus$ which have been prepared by this process.

A subclass of the compounds of the general formula (I) is the compound of the general formula

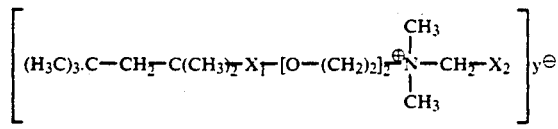

These are derivatives of the benzethonium halides. By substitution of the radicals $X_1$ and $X_2$, where $X_1$ may be equal to $X_2$, these compounds can be made analogously as already described in U.S. Pat. No. 2,115,250 (1938) or U.S. Pat. Nos. 2,170,111 (1939) and 2,229,024 (1941). These specific N-tensides are particularly stable even in the presence of a potentiating mixture and suprisingly have a high absorptive capacity for micellar inclusion of pharmaceutical active substances. Moreover, when carried out according to this method they are independent of the environment. $Y\ominus$ is an anion, for example chloride, bromide or *also* iodide, a low alkonate, such as formate, acetate, propionate, malate or fumarate, salicylate, alginate or gluconate.

TABLE 4

Preparation and melting point and elementary analysis of the quarternary ammonium compounds of the type $RN^-(CH_3)_3Y\ominus$ from $R_n, R_m, R_1, R_2 N\oplus Y\ominus$ with $R_1 = R_2$ and $R_n = R_m$.

| No. | R | $Y\ominus$ | cmc mol | Fp. °C. | C | H | N | Y |
|---|---|---|---|---|---|---|---|---|
| 1 | Methyl | Br | $1.5 \times 10^{-5}$ | | 27.90 | 6.56 | 6.49 | |
| 2 | Ethyl | I | $2.0 \times 10^{-5}$ | >300^c | 27.92 | 6.56 | 6.51 | |
|   |       |   |                     | >300^d |       |      |      |   |
| 3 | n-Propyl | I | $2.0 \times 10^{-5}$ | 190 | 31.51 | 7.05 | 6.09 | |
|   |          |   |                     | 189 | 31.46 | 7.04 | 6.11 | |
| 4 | Isopropyl | I | $3.5 \times 10^{-5}$ | >300 | 31.50 | 7.08 | 6.09 | |
|   |           |   |                     | 316 | 31.46 | 7.04 | 6.11 | |
| 5 | n-Butyl | I | $4.1 \times 10^{-5}$ | 231 | 34.69 | 7.48 | 5.72 | |
|   |         |   |                     | 226 | 34.58 | 7.46 | 5.76 | |
| 6 | t-Butyl | I | $6.0 \times 10^{-6}$ | 256 | 34.66 | 7.47 | 5.72 | |
|   |         |   |                     | 260 | 34.58 | 7.46 | 5.76 | |
| 7 | n-Pentyl | I | $7.0 \times 10^{-5}$ | 224 | 37.28 | 7.86 | 5.41 | |
|   |          |   |                     |     | 37.37 | 7.84 | 5.45 | |
| 8 | 1-Methylbutyl | I | $1.0 \times 10^{-6}$ | 224 | 37.48 | 7.87 | 5.43 | 49,17 |
|   |               |   |                     |     | 37.37 | 7.84 | 5.45 | 49,34 |
| 9 | n-Hexyl | I | $7.9 \times 10^{-6}$ | 160 | 39.68 | 8.19 | 5.11 | |
|   |         |   |                     | 166 | 39.86 | 8.18 | 5.16 | |
| 10 | Cyclopentyl | I | $6.0 \times 10^{-6}$ | 271 | 37.78 | 7.13 | 5.41 | 49,63 |
|    |             |   |                     |     | 37.66 | 7.11 | 5.47 | 49,74 |
| 11 | Cyclohexyl | I | $7.1 \times 10^{-6}$ | 271 | 40.25 | 7.48 | 5.18 | |
|    |            |   |                     |     | 40.16 | 7.49 | 5.20 | |
| 12 | Allyl | I | $1.5 \times 10^{-7}$ | 104 | 31.81 | 6.22 | 6.15 | 55,76 |
|    |       |   |                     | 102 | 31.73 | 6.21 | 6.17 | 55,89 |
| 13 | 2-Propynyl | I | $6.0 \times 10^{-5}$ | 181 | 32.09 | 5.40 | 6.19 | 56,29 |
|    |            |   |                     |     | 32.01 | 5.37 | 6.22 | 56,39 |
| 14 | 3-Butenyl | I | $3.5 \times 10^{-5}$ | 236 | 34.93 | 6.70 | 5.78 | 52,56 |
|    |           |   |                     |     | 34.87 | 6.69 | 5.81 | 52,63 |
| 15 | Phenyl | I | $7.0 \times 10^{-5}$ | 227 | 41.12 | 5.38 | 5.31 | 48,15 |
|    |        |   |                     | 227 | 41.08 | 5.36 | 5.32 | 48,23 |
| 16 | Benzyl | I | $7.3 \times 10^{-5}$ | 179 | 43.33 | 5.82 | 5.00 | |
|    |        |   |                     | 179 | 43.33 | 5.82 | 5.05 | |
| 17 | 4-Chlorbutyl | I | $5.1 \times 10^{-6}$ | 182 | 29.42 | 5.97 | 5.01 | |
|    |              |   |                     |     | 30.28 | 6.17 | 5.05 | |
| 18 | 4-Brombutyl | I | $7.0 \times 10^{-6}$ | 131 | 25.30 | 5.40 | 4.62 | |
|    |             |   |                     |     | 26.10 | 5.32 | 4.35 | |
| 19 | 4-Iodobutyl | I | $1.5 \times 10^{-7}$ | 160 | 23.43 | 4.75 | 4.00 | 67,80 |
|    |             |   |                     |     | 22.78 | 4.64 | 3.79 | 68,79 |
| 20 | 2-Ethoxyethyl | Br | $2.0 \times 10^{-7}$ | 174 | 39.07 | 8.44 | 6.49 | 38,48 |
|    |               |    |                     |     | 39.63 | 8.55 | 6.60 | 37,67 |
| 21 | 2-Phenoxyethyl | Br | $1.5 \times 10^{-7}$ | 162 | 50.74 | 6.98 | 5.34 | 30,79 |
|    |                |    |                     |     | 50.78 | 6.97 | 5.38 | 30,71 |

TABLE 4-continued

Preparation and melting point and elementary analysis of the quarternary ammonium compounds of the type $RN^+(CH_3)_3 Y^\ominus$ from $R_n$, $R_m$, $R_1$, $R_2 N^\oplus Y^\ominus$ with $R_1 = R_2$ and $R_n = R_m$.

| No. | R | $Y^\ominus$ | cmc mol | Fp. °C. | \multicolumn{4}{c|}{Analysis found} |
| | | | | | C | H | N | Y |
|---|---|---|---|---|---|---|---|---|
| 22 | p-Methylbenzyl | Br | $2.0 \times 10^{-7}$ | 197 | 53.97 | 7.78 | 5.66 | 32.49 |
|    |                 |    |                     |     | 54.10 | 7.43 | 5.74 | 32.72 |
| 23 | p-Fluorbenzyl  | Br | $2.5 \times 10^{-7}$ | 237 | 48.32 | 6.10 | 5.61 |       |
|    |                 |    |                     |     | 48.40 | 6.09 | 5.65 |       |
| 24 | p-Chlorbenzyl  | Br | $3.0 \times 10^{-5}$ | 207 | 45.39 | 5.71 | 5.29 |       |
|    |                 |    |                     |     | 45.39 | 5.75 | 5.26 |       |
| 25 | p-Brombenzyl   | Br | $4.0 \times 10^{-5}$ | 220 | 38.93 | 4.92 | 4.52 | 51.59 |
|    |                 |    |                     |     | 38.86 | 4.89 | 4.53 | 51.71 |

The cationic tenside according to the invention is preferably a compound of the general formula $$[HET=N^+-(CH_2)_x-CH_3]Y^-$$

wherein
  $HET=N^+$ is a substituted or non-substituted pyridinium radical or
  a substituted or non-substituted pyrimidinium radical or
  a substituted pyrazine-(1,4-diazinium) radical or
  an imidazolium radical (4.5-d)pyrimidine radical, substituted or non-substituted, or
  a substituted or non-substituted imidazolium radical or
  a substituted or non-substituted pyrazolium radical or
  a substituted or non-substituted thiazolium radical, or
  a substituted or non-substituted benzthiazolium radical or
  a substituted or non-substituted benzimidazolium radical,
  $x = 8$ to 20 and
  $y^- =$ chloride, bromide, iodide, formate, acetate, propionate, hydrogen sulfate, malate, fumarate, salicylate, alginate, gluconate or ethyl sulfate.

Preferred embodiments of this cationic tenside are the following compounds:

In the following embodiments, in which $y^-$ occurs, this $y^-$ denotes in each case one of the above thirteen anions.

N-alkyl pyridinium of the formula $$\left[\bigcirc N^\oplus-(CH_2)_x-CH_3\right] y^\ominus$$

hexadecylpyridinium of the formula $$\left[\bigcirc N^\oplus-(CH_2)_{15}-CH_3\right] y^\ominus$$

N-alkyl-4-hydroxypyridinium of the formula $$\left[HO-\bigcirc N^\oplus-(CH_2)_x-CH_3\right] y^\ominus$$

hexadecyl-4-hydroxypyridinium of the formula $$\left[HO-\bigcirc N^\oplus-(CH_2)_{15}-CH_3\right] y^\ominus$$

2,5,6 substituted $N_1$-alkyl pyridinium compounds of the formula

[structure with $R_3$, $R_1$, $R_2$, $N^\oplus$, $(CH_2)_x-(CH_3)$] $y^\ominus$ $R_1 = R_2 = R_3 = H$
$R_1 = NH_2; R_2 = OH; R_3 = H$
$R_1 = NH_2; R_2 = OH; R_3 =$
$R_1 = OH; R_2 = OH; R_3 = CH_3$
$R_1 = OH; R_2 = OH; R_3 = H$
$R_1 = F; R_2 = OH; R_3 = H$
$R_1 = OH; R_2 = OH; R_3 = F$ 2,5,6 substituted $N_1$-hexadecylpyrimidinium of the formula

[structure with $R_3$, $R_1$, $R_2$, $N^\oplus$, $(CH_2)_{15}-CH_3$] $y^\ominus$ $R_1 = R_2 = R_3 = H$
$R_1 = NH_2; R_2 = OH; R_3 = H$
$R_1 = NH_2; R_2 = OH; R_3 =$
$R_1 = OH; R_2 = OH; R_3 = CH_3$
$R_1 = OH; R_2 = OH; R_3 = H$
$R_1 = F; R_2 = OH; R_3 = H$
$R_1 = OH; R_2 = OH; R_3 = F$ 4-n-alkyl-pyrazinium-2-carboxamide of the formula 4-hexadecylpyrazinium-2-carboxamide of the formula

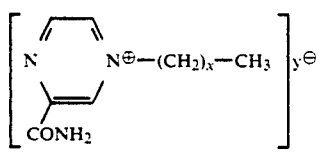

7-n-alkyl-imidazolium[4,5-d]-pyrimidine of the formula

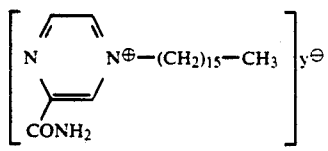

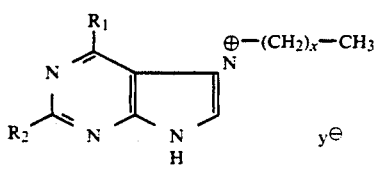

$R_1$ = OH: $R_2$ = OH
$R_1$ = H: $R_2$ = H
$R_1$ = F: $R_2$ = $NH_2$
$R_1$ = F: $R_2$ = OH
$R_1$ = $NH_2$: $R_2$ = H
$R_1$ = $NH_2$: $R_2$ = $NH_2$ 7-hexadecylimidazolium[4,5-d]pyrimidine of the formula

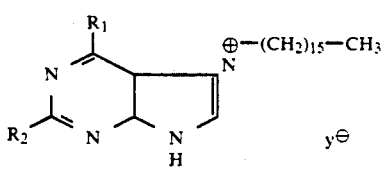

$R_1$ = OH: $R_2$ = OH
$R_1$ = H: $R_2$ = H
$R_1$ = F: $R_2$ = $NH_2$
$R_1$ = F: $R_2$ = OH
$R_1$ = $NH_2$: $R_2$ = H
$R_1$ = $NH_2$: $R_2$ = $NH_2$ 3-n-alkyl-5,6-substituted benzimidazolium compounds of the formula

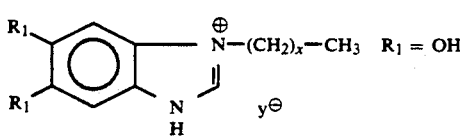

4-substituted 2-hexadecylpyrazolium compounds of the formula

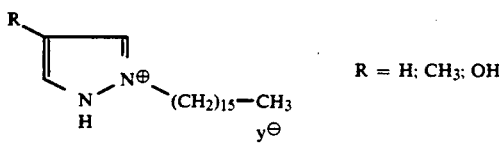

1-n-alkyl-4-substituted imidazolium compounds

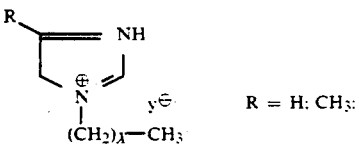     R = H: $CH_3$:

1-hexadecyl-4-substituted imidazolium compounds of the formula

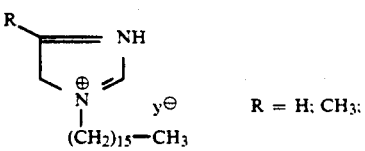     R = H: $CH_3$:

3-n-alkyl-5,6-substituted thiazolium compounds of the formula

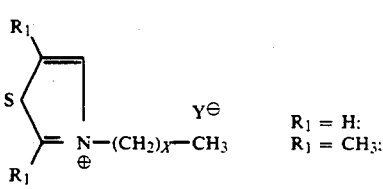     $R_1$ = H:
                         $R_1$ = $CH_3$:

3-n-hexadecyl-2,5-substituted thiazolium compounds of the formula

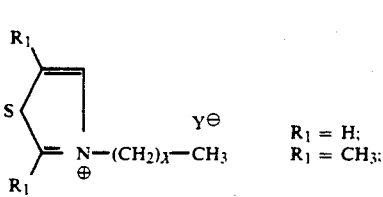    $R_1$ = H:
                         $R_1$ = $CH_3$:

3-n-alkyl-5,6-substituted benzthiazolium compounds of the formula

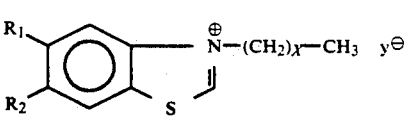

$R_1$ = $R_2$ = H
$R_1$ = $CH_3$
$R_1$ = $R_2$ = OH
$R_1$ = $R_2$ = $CH_3$

4-[1,1 bis n-alkyl (low alkyl)]N-hexadecylpyridinium compounds of the formula

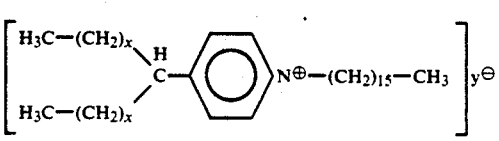

3,5 bis[(n-alkyloxy)carbonyl]N-hexadecylpyridinium compounds of the formula

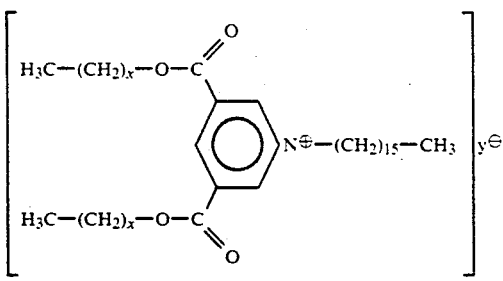

4-(17-tritriacontyl)-n-methyl-pyridinium chloride of the formula

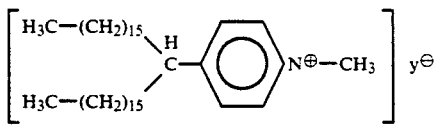

3,5 bis[(n-hexadecyloxy)carbonyl)]-N-methyl-pyridinium chloride

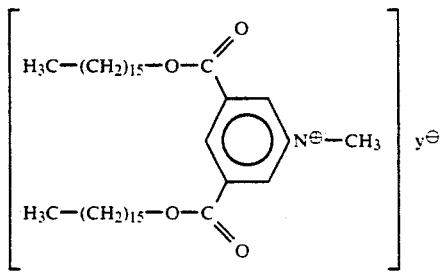

Cationic tensides of the general formula

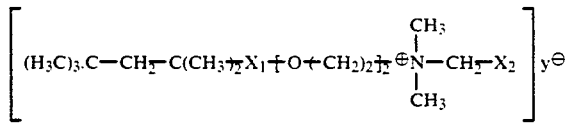

wherein
- $x_1$ = a non-substituted phenyl radical or a phenyl radical substituted in the 4-position or in the 3,5-position or in the 1,2,4,5-position.
- $x_2$ = a non-substituted phenyl radical or a phenyl radical substituted in the 4-position or in the 3,5-position or in the 1,2,4,5-position and
- $y^-$ = the anions according to claim 78.

GENERAL REMARKS ON THE PREPARATION OF THE $(HET=N^+-(CH_2)_x-CH_3)Y^-$ COMPOUNDS II

The cationic tensides according to the invention of the general formula II are novel apart from hexadecyl-pyridinium halide.

In the cationic tenside of the general formula II $HET=N^+$ is preferably a substituted or non-substituted pyridinium radical or a substituted or non-substituted pyridinium radical or a substituted pyrazine-(1,4-diazinium) radical or an imidazolium radical (4,5-d) pyrimidine radical, substituted or non-substituted, or a substituted or non-substituted imidazolium radical or a substituted or non-substituted pyrazolium radical, or a substituted or non-substituted thiazolium radical or a substituted or non-substituted benzthiazolium radical, or a substituted or non-substituted benzimidazolium radical.

These cationic tensides are characterized in that they have a very small critical micellization constant (cmc) of approximately $1.5 \times 10^{-7}$ mol, are very highly antimicrobial and antifungal, do not exhibit any polydispersity in the presence of inorganic anions or potentiating mixtures and in some cases themselves are microbial metabolism products (antimetabolites) which are not toxic for the host cell.

The formation of the salt-like structure of this class of cationic tensides of the form $(HET=N^\oplus-(CH_2)_x-CH_3)Y^\ominus$ is inter alia due to the electron density distribution of the heteroaromatic cores and their basicity, including the influence of the substituents. A necessary condition leading to the formation of quaternary salts of this five and six-member heteroaromatic class is that the electron density at the nitrogen which is rendered quaternary has a magnitude determined by MO-SCF calculations of $-0.08$ (e.g. pyrazine-$N_4$) to $-0.159$ (e.g. imidazole-$N_1$, pyrine-$N_7$). The stability of the individual heterocyclic cationic tensides described here is moreover also governed by their symmetry and the length of the alkyl chain at the quaternary nitrogen:

In the case of the imidazole, benzimidazole, for example, stabilization is by formation of the salt at the quantternary nitrogen $N_1$ and the free electron pair at $N_3$ and the resulting high symmetry. The same applies to the $N_9$-tautomer of purine and its symmetrically arranged substituents which influence the negative charges at the $N_1$ ($-0.124$), $N_3$ ($-0.108$) and $N_9$ ($-0.149$) in such a manner that the quaternization at the $N_9$ is preferred in that the aforementioned order $N_1 \rightarrow N_3 \rightarrow N_9$ is reversed. The yields can be increased by the choice of suitable solvents. Whereas for pyridine, pyrimidine and imidazole radicals symmetrical effects at the core play an important part in the case for example of pyrazine the electronic effect in the 2-position is significant but there are also very pronounced inductive effects (e.g. 2-amino group), less than mesomers. This also applies to pyrazole.

The length of the alkyl chain at the quaternary nitrogen atom governs not only the melting point and hydrophobicity of the cationic micelles subsequently formed in aqueous solutions; in addition, the yields decrease with increasing chain length whilst the reaction times increase for example in nitrobenzene of 2-ethoxyethanol.

Stable and easily crystallizable compounds are obtained for $C_{12}$-$C_{18}$, the counter ion $Y^\ominus$ being without exception bromide and chloride. The other compounds can easily be recrystallized from acetone or chloroform. The corresponding iodine compounds are sensitive to heat and light.

SPECIFIC PREPARATION OF THE $(HET=N^\oplus-(CH_2)_x-CH_3)Y^\oplus$ COMPOUNDS a) The corresponding compounds of pyridine or substituted pyridine, as six-member heterocycle, can be prepared from the corresponding alkyl bromides or iodides in methanol at 35° C. and pyridine or substituted pyridines with a yield of 70%. The corresponding molar amounts of the alkyl bromide, almost all of which are available commercially but which must be subsequently preparatively purified by high-pressure liquid chromatography (HPLC), are firstly dissolved in methanol (10 times excess volume with respect to pyridine) and under nitrogen the stoichiometric amount of pyridine, also dissolved in methanol, added dropwise whilst stirring. Heating is carried out for 6 hours under reflux whilst stirring at 70° C. so that the reaction yield is almost quantitative. Thus, for example, the yield of hexadecyl-4-hydroxypyridinium chloride or bromide in methanol as solvent is 95%, with ethanol 80% and in ether/ethanol only 40%. Dodecylpyridinium chloride is obtained with a yield of almost 70%. 3,5-dihydroxydodecylpyridinium bromide is formed quantitatively in accordance with the above procedure from dodecyl bromide and 3,5-dihydroxypyridine in boiling chloroform after 4 hours (melting point 180° C.).

Purification of the corresponding pyridinium compounds: By repeated recrystallization from mixtures of methanol/ether, starting with 40/60 (v/v); 50/50 (v/v) and finally 90/100 (v/v), the desired products are obtained with constant melting point, uniform molecular weight and specific surface-active properties (measured by the concentration dependence of the surface tension). In addition these compounds exhibit the typical $^1$H-NMR signals outlined above. The numerous $CH_2$ groups and the $CH_3$ group generate a clearly visible absorption band in the IR spectrum at 2930 cm$^{-1}$ and 2850 cm$^{-1}$ (methylene group) a medium-weak band at 2960 cm$^{-1}$ and a weak band at 2870 cm$^{-1}$ which can be assigned to the methyl group.

A rapid and quantitative separation of the n-alkyl pyridinium halides from unconverted n-alkyl bromides and pyridine is achieved by preparative high-pressure liquid chromatography on an RP18 column with the aid of an elution mixture consisting of 60% (v/v) methanol (ethanol) and acetone nitrile 40% (v/v) isocratic at 9.52 atm column pressure (UV detection at 260 nm).

b) Pyrimidine compounds

1) Hexadecylpyrimidinium bromide, 0.01 mol, 5-aminopyrimidine (0.95 g) and hexadecyl bromide, 0.01 mol (3.05 g), are reacted in 20 ml methanol whilst stirring under nitrogen at 20° C. for 24 hours in the presence of catalytic amounts (0.5 mg) sodium amide.

The resulting $N_1$-hexadecyl-5-aminopyrimidinium bromide is dissolved in acetone at 76° C. and after cooling to room temperature the $N_1$-hexadecyl-5-aminopyridinium bromide crystallizes with a melting point of 122° C. Yield 35%.

0.01 mol of this $N_1$-hexadecyl-5-aminopyrimidinium bromide (3.20 g) are stirred in methanol/water 50/50 (v/v) at 0° C. in an ice bath with 1 g $NaNO_2$ and 0.1 ml concentrated hydrobromic acid under nitrogen for 6 hours. Thereafter the mixture is brought to room temperature and subsequently refluxed at 80° C. for 2 hours under nitrogen whilst stirring. The resulting hexadecylpyrimidinium bromide is extracted with 2-ethoxyethanol and caused to crystallize out at 10° C. Yield 30%, melting point 105° C. (bromide), 189° C. (chloride).

Preparative separation of non-converted products can also be achieved by high-pressure liquid chromatography as described for the pyridinium derivatives.

2) Pyrimidinium compounds substituted in 2,5,6-position are obtained by reaction in 2-ethoxy ethanol under pressure in an autoclave at 100° C. with a reaction duration of 8 hours from the corresponding n-alkyl bromides or iodides and the substituted pyrimidine compounds and the yields are between 30 and 40%. The recrystallizations are carried out from chloroform for all the substituted pyrimidinium compounds.

Preparative separation of unconverted products can be carried out as described above by high-pressure liquid chromatography.

3) $N_1$-n-alkyl compounds of pyrimidine can be obtained in good yields by reaction of n-alkyl-Mgx(x=Br, Cl) with pyrimidine or 2,6,5,6-substituted pyrimidines in the presence of 1,2-dimethoxyethane and/or n-heptane. No hetarine or addition-elimination or elimination-addition mechanism takes place.

0.01 mol (1.0 g) 5-fluuoropyrimidine are dissolved in 1,2-dimethoxymethane (100 ml) whilst stirring in a three-neck flask under nitrogen. From a dropping funnel 0.08 mol (same order of magnitude as above) n-decylmagnesium chloride (0.09 mo$\triangleq$29.6 g n-hexadecylmagnesium bromide) dissolved in 20 ml heptane is added dropwise slowly at 20° C. This solution is brought to 40° C., stirred for 12 hours and when the reaction is completed from a dropping funnel 20 ml 50% by weight hydrobromic acid is added dropwise at constant temperature. After 1 hour the excess Grignard reagent is reacted. It is cooled to 0° C. and any excess of Grignard reagent still present eliminated by adding methanol, the quaternary $N_1$-pyrimidinium bases then being extracted by 2-ethoxyethanol. The first recrystallization is carried out from chloroform/methanol at 0° C. and the further recrystallizations at room temperature.

Melting point: 5-fluoro-$N_1$-decylpyrimidinium bromide 199° C. (decomposition).

Melting point: 5-fluoro-hexadecylpyrimidinium bromide 175° C. (decomposition).

c) Preparation of 7-n-alkyl-imidazolium[4,5-d]pyrimidine derivatives (purine), e.g. 7-hexadecylimidazolium-2,6-dihydroxy[4,5-d]pyrimidine bromide 1.5 g 2,6-dihydroxy purine (0.01 mol) are dissolved in 100 ml acetone in a four-neck flask at 35°. From two dropping funnels whilst stirring under nitrogen firstly triethyloxonium boron fluoride ($Et_3O^{\oplus}BF_4$) in triple excess (5.7 g=0.03 mol) with respect to n-hexadecyl bromide (3.3 g, 0.01 mol) which is dispensed in the second dropping funnel is added dropwise simultaneously with n-hexadecyl Br. The reaction is continued with constant stirring for 6 hours at 40° C. and subsequently refluxing is carried out at 65° C. for 10 hours. After completion of the reaction 100 ml ethanol is added, the quaternary ammonium base formed filtered over a sintered-glass crucible (1G4) and recrystallized from a mixture consisting of 2-ethoxyethanol/chloroform, 1:1. Yield: 0.5 g, melting point: 122° C.

The compound is hygroscopic and forms a crystalline adduct with two parts chloroform.

The UV spectra exhibit the typical absorption properties of the purine derivatives. This also applies to the $^1$H-NMR spectra, measured in $d_6$-$Me_2SO_4$.

d) The corresponding benzothiazole and benzimidazole-n-alkyl compounds, particularly when they are halogenated in the 2-position, form with this process with a yield of 50% and can be very easily recrystallized from chloroform.

e) The corresponding quaternary salts of the pyrazole may also be prepared by process c). Process b3) may also be employed with n-hexylmagnesium bromide or n-alkylmagnesium chloride because neither an addition-elimination nor an elimination-addition mechanism takes place. The 4-H-pyrazolium salts with R=$CH_3$, OH, H form with a high yield of 60%.

Since the n-alkyl radical can be localized both at the $N_1$ and at the $N_2$ or both, the reaction product must be separated as described above by high-pressure liquid chromatography in an RP-18 column in an acetone/acetonitrile elution mixture. This is also necessary when the corresponding n-alkyl bromide is brought to react in a sealed tube or autoclave with a pyrazole derivative at 100° C. in the presence of piperidine. The ratio of di-N-substituted to mono-$N_2$-substituted pyrazolium derivatives is 1.5:1.

f) The imidazolium compounds, both the $N_1$-substituted and the $N_1$, $N_2$-disubstituted, can be prepared like the corresponding pyridinium compounds.

To prepare the $N_1$-substituted imidazolium compounds the procedure described under b3) is adopted. The yields are 30%. Acetone is a suitable reaction medium.

g) The quaternization of the pyrazine at the $N_4$ when substituted in the 2-position takes place with a 50% yield when for example a chlorine or a carboxamide (carbamoyl) group is located in the 2-position. If the method under b1) is adopted yields of 20–30% are obtained, depending on the size of the alkyl radical. If the known procedure for preparing pyridinium compounds (a) is adopted the yields are increased to 50%.

As usual and as explained above the $(CH_2)_x$ chain with $x = 10$–20 governs the size and the cmc in aqueous solutions. The resulting size, form and molecular weight distribution of the micelle in aqueous solution at pH 7.0 depend on the nature of the counter ion $Y^\ominus$.

The covalently bound pharmaceutical active substances may for example be extended to 9-$\beta$-arabino-1,4-adenine, 5-fluorocytosine, aza-uridine, 6-mercaptopurine or thioguanine. These also include the nucleosides or nucleotides of the thymidine series which inhibit the growth of neoplastic tumors inter alia by inhibiting the DNA synthesis. Also to be mentioned here are the antiviral substances of the 1,3,5-triazines, e.g. the 2-acetamido-4-morphino-1,3,5-triazine, which has virustatic properties against Herpes zoster.

TABLE 2

Characteristic properties of the $N^\oplus$ tensides of the general formula HET $N^\oplus \equiv (CH_2)_x - CH_3$ $Y^\ominus$

| No. | HET $N^\oplus \equiv (CH_2)_x - CH_3$ | $Y^\ominus$ | Fp. °C. | Analysis (%) Found C | H | N | Y | cmc × $10^{-6}$M |
|---|---|---|---|---|---|---|---|---|
| 1. | Hexadecyl-4-Hydroxy-pyridinium | Br.½H₂O | 85 | 59.86 | 10.94 | 4.37 | 24.83 | 0.95 |
| 2. | Dodecyl-pyridinium | Cl.H₂O | 73 | 71.46 | 11.20 | 4.90 | | 1.52 |
| 3. | 2-Hydroxy,6-amino-hexadecyl-pyrimidinium | Cl | 155 | 61.45 | 18.69 | 10.76 | 9.10 | 2.00 |
| 4. | Hexadecyl-pyrimidinium | Br | 105 | 62.02 | 10.09 | 7.25 | | 2.50 |
| 5. | 2,6-Dihydroxy,5-Fluor, hexadecyl-pyrimidinium | Cl.2H₂O | 172 | 61.13 | 22.68 | 7.14 | 9.05 | 0.85 |
| 6. | 2-Hydroxy,5-methyl,6-amino-hexadecyl-pyrimidinium | Br | 192 | 56.18 | 16.67 | 9.36 | | 1.00 |
| 7. | Dodecyl-pyrimidinium | Cl | 85 | 64.79 | 13.78 | 9.45 | | 1.20 |
| 8. | 2,6-Dihydroxy-dodecyl-pyrimidinium | Br | 70 | 53.07 | 17.12 | 7.75 | 22.06 | 1.90 |
| 9. | 2-Carboxamide-4-hexadecyl-1,4-diazinium | Cl | 195(dec.) | 71.30 | 6.77 | 11.89 | | 0.30 |
| 10. | 7-Hexadecylimidazolium-2,6-dihydroxy[4,5-d]pyrimidin | Cl.1H₂O | 112 | 60.80 | 17.13 | 13.51 | | 0.50 |
| 11. | 7-Hexadecylimidazolium-2,6-diamino-[4,5-d]pyrimidine | Br.½H₂O | 170(dec.) | 55.17 | 8.93 | 18.41 | 17.49 | 1.30 |
| 12. | 3-Hexadecylbenzimidazolium | Cl.H₂O | 100 | 72.53 | 10.80 | 7.35 | | 6.70 |
| 13. | 4-Methyl- -2-hexadecyl-pyrazolium | Cl | 172 | 69.67 | 11.89 | 8.14 | | 0.70 |
| 14. | 5-Methyl-1-hexadecylimidazolium | Cl | 142 | 69.69 | 11.89 | 8.12 | | 3.90 |
| 15. | 3-Hexadecylthiazolium | Br.2H₂O | 155 | 58.20 | 17.83 | 3.59 | | 0.91 |
| 16. | 2,5-Dimethyl-3-hexadecyl-thiazolium | Br.1H₂O | 170(dec.) | 57.15 | 20.50 | 3.34 | 19.01 | 15.00 |
| 17. | 3-Hexadecyl-6-methyl-benzimidazolium | Cl.2H₂O | 119(dec.) | 69.81 | 14.13 | 7.09 | | 17.00 |
| 18. | 3-Dodecyl-6-methyl-benzimidazolium | Br.1H₂O | 98 | 59.40 | 12.52 | 7.29 | | 7.30 |
| 19. | 3-Hexadecyl-5,6-dihydroxy-benzthiazolium | Cl.2H₂O | 70 | 60.60 | 28.54 | 3.07 | 7.79 | 7.90 |
| 20. | 3-Dodecyl-benzthiazolium | Br.1H₂O | 90 | 70.20 | 14.57 | 4.31 | | 10.90 |

TABLE 3

Yields and hydrodynamic radius of N-tensides of the formula HET = N—$(CH_2)_x$—CH and benzethonium derivatives in dependence upon $Y^\ominus$

| No. | Tenside | Counter ion $Y^\ominus$ | $<R_H>$ (Å) | Yield (%) |
|---|---|---|---|---|
| 1 | N-Cetyl-4-methyl-imidazolinium | Br$^\ominus$ | 140.0 | |
| | | Cl$^\ominus$ | 70.0 | 60 |
| | | NO₃⁻ | 20.0 | 70 |
| 2 | N-Hexadecyl-4-cetyl-imidazolinium | Cl$^\ominus$ | 100 | 40 |
| | | HSO₄⁻ | 150 | 30 |
| 3 | N-Hexadecyl-5-carboxamide pyridinium | Br$^\ominus$ | 120.0 | 60 |
| | | Cl$^\ominus$ | 55.0 | 60 |
| | | Fumarate | 70.0 | 70 |
| | | Maleate | 120.0 | 30 |
| 4 | 8-Ketohexadecylpyridinium | Cl$^\ominus$ | 50.5 | 00 |
| | | Br$^\ominus$ | 140.0 | 80 |

TABLE 3-continued

Yields and hydrodynamic radius of N-tensides
of the formula HET = N—(CH$_2$)$_x$—CH
and benzethonium derivatives in dependence upon Y$^\ominus$

| No. | Tenside | Counter ion Y$^\ominus$ | <R$_H$> (Å) | Yield (%) |
|---|---|---|---|---|
|   |   | NO$_3^-$ | 170.0 | 100 |
| 5 | Methyl-3-stearyloxy-propyl-pyridinium | Cl$^\ominus$ | 140.0 | 60 |
|   |   | Salicylate | 1000.0 | 60-80 (20.25° C.) |
| 6 | Cetyl-2,3-dihydroxy-propyl-hexadecyl-pyridinium | Cl$^\ominus$ | 150.0 | 20 |
|   |   | Br$^\ominus$ | 180.4 | 25 |
|   |   | OH$^\ominus$ | 210.4 | 30 |
|   |   | Maleate | 120.0 | 41 |
| 7 | 3,5-bis[(n-hexadecyloxy-carbonyl]-N-methyl-pyridinium | Salicylate | 1000 | 60 |
|   |   | Fumarate | 2500 | 70 |
|   |   | Cl$^\ominus$ | 350 | 50 |
| 8 | a) 2.-4-Dihydroxy-5-methyl-hexadecyl-pyridinium | Cl$^\ominus$ | 1000 | 30 |
|   |   | Br$^\ominus$ | 1500 | 30 |
|   | b) 2.-4-Dihydroxy-5-Fluoro hexadecyl-pyridinium | Br$^\ominus$ | 210 | 30 |
|   |   | Cl$^\ominus$ | 150 | 30 |
| 9 | a) 2-Carboxamid-3-hexadecyl-1,4-pyridinium | Cl$^\ominus$ | 220 | 30 |
|   |   | NO$_3^-$ | 440 | 30 |
|   | b) 2-carboxamid-3-dodecyl-1,4-pyridinium | NO$_3^-$ | 366 | 30 |
|   |   | Fumarate | 750 | 30 |
| 10 | 3-[[(Dimethylamino)-carboxyl]oxyl]-1-hexadecyl-pyridinium | Cl$^\ominus$ | 450 | 30 |
|   |   | Fumarate | 700 | 60 |
|   |   | Br$^\ominus$ | 1000 | 40 |
| 11 | 3-hexadecyl-benzimidazo-linium | Cl$^\ominus$ | 300 | 50 |
|   |   | Maleate | 1500 | 40 |
|   |   | Fumarate | 250 | 30 |
|   |   | NO$_3^-$ | 500 | 70 |
|   |   | SO$_4^{2-}$ | 350 | 70 |
| 12 | Benzyldimethyl[2-[2-(p-1,1,3,3,tetramethylbutyl-p.p'-dimethyl-phenoxy)ethoxy]ethyl]ammonium | Cl$^\ominus$ | 150 | 30 |
|   |   | Br$^\ominus$ | 3000 | 40 |
|   |   | NO$_3^\ominus$ | 150 | 10 |
|   |   | Maleate | 3000 | 20 |
|   |   | Fumarate | 2500 | 25 |
|   |   | Salicylate | 3000 | 20 |

The following FIG. 4 shows the variance of the hydrodynamic radius of benzethonium chloride and N-hexadecyl-4-cetylimidazolium salicylate in dependence upon the hydrodynamic radius after various periods of ultrasonic treatment in minutes, measured by inelastic laser light scattering.

FURTHER PREFERRED EMBODIMENTS OF THE INVENTION

Whereas the overall range of the critical micellization concentration (cmc) is from $1.0 \cdot 10^{-7}$ to $1.5 \cdot 10^{-4}$ mol/liter, the cmc preferably lies in the range from 1.0 to $8.5 \cdot 10^{-7}$/liter.

Preferably, the cationic tenside with the monovalent anion is contained in an amount of 0.05 to 0.1% by weight with respect to the total pharmaceutical preparation.

Particularly good results are achieved when the cationic tenside with the monovalent anion is contained in an amount of 0.08-0.1% by weight with respect to the total pharmaceutical preparation.

Preferably, the hydrophobic pharmaceutical active substance is contained in an amount of 0.06-0.5% by weight with respect to the total pharmaceutical preparation.

Particularly good results are achieved when the hydrophobic pharmaceutical active substance is contained in an amount of 0.001-0.005% by weight with respect to the total pharmaceutical preparation.

Preferably, the solvents are water or water+glycerol or water+glycerol+ethanol.

Preferably, the monovalent anion is a monobasic or dibasic fatty acid radical.

Preferably, the monovalent anion is acetate, propionate, fumarate, maleate, succinate, aspartate or glutamate.

Preferably the monovalent anion is a sugar radical.

Preferably, the monovalent anion is gluconate, galacturonate or alginate.

Preferably, the monovalent anion is chloride, bromide, iodide or hydrogen sulfate.

Preferably, the hydrophobic pharmaceutical active substance is an antimicrobial active substance or an antifungal active substance or an antiproliferative active substance or an antiviral active substance.

Preferably, the hydrophobic pharmaceutical active substance is an inorganic compound of the elements zinc or mercury or tungsten and/or antimony. Preferably, the inorganic compound is Z$_n$SO$_4$ or Z$_n$O or Hg(CN)$_2$ or (NH$_4$)$_{18}$(NaW$_{21}$Sb$_9$O$_{86}$)$_{17}$ or an alkali or alkaline earth salt of phosphonic acid ROP(O)Me$_2$ or an N-phosphonoacetyl-1-aspartate.

Preferably, the hydrophobic pharmaceutical active substance is an antibiotical and antiviral active substance or an antifungal active substance or an antineoplastic active substance.

Preferably, the solvent is water and/or ethanol and/or glycerol. Preferably, the solvent is water and/or ethanol and/or dimethylsulfoxide.

Whereas the pH value of the solvent must be $\leq 7$, the preferable pH value of the solvent=5 or is in the vicinity of 5.

The pharmaceutical preparation may be made according to the invention substantially in that firstly the solvent is placed into a reaction vessel, then the cationic tenside is added whilst stirring at room temperature, then the hydrophobic pharmaceutical active substance is added to the resulting isotropic micellar solution at room temperature and stirring continued until complete dissolving thereof.

Particularly favourable results are achieved with the cationic tensides of the general formula II when x=14, i.e. the alkyl chain has 15 C atoms.

These straight-chain $C_{15}$ derivatives of the N-tensides are distinguished in particular by their simple chemical preparation. In addition, they surprisingly have the lowest cmc (it is about $2.5 \cdot 10^{-7}$ mol/liter). They are furthermore very easy to control by $Y^-$ (form, molecular weight distribution, polydispersity). Also, they are variable due to the size of the alkyl chain and thus as regards absorption of the pharmaceutical active substances. Finally, they can be easily crystallized.

As already mentioned the radical hexadecylpyridinium is known per se (as pure chemical compound). Not known is the influence according to the invention of the associated anion ($Y^-$) on the micelle size and the form of the micelle. With regard to the independent substance protection claimed according to the application for all the novel compounds disclosed a generic designation is given below which covers preferably the novel compounds according to the invention. This term reads "isoelectronic heterocyclic nitrogen bases with 5 or 6 rings containing either 2 N-atoms in the 1,2-position or 1,3-position or 1,4-position or an S-atom in 1-position with an N-atom in 3-position".

PRODUCTION PROCESS FOR THE PHARMACEUTICAL PREPARATION

General Remarks on the Preparation of the Aqueous Phase

To obtain preferably a monodisperse homogeneous and isotropic aqueous solution of the $N^+$-tensides both as regards form (spherical, oval, elongated) and size and as regards molecular weight distribution, the solutions indicated, together with their included hydrophobic pharmaceutical active substances, must be a. ultrasonically treated for example at 100 watt for one minute, possibly thereafter then by b, b. subsequently purified by column chromatography, e.g. on an Agarose A 0.5 m, Sepharose 2 B, Sephadex G 200, DEAE-Sepharose Cl-6B at pH 6.0 or an Ultragel AcA44 (pH 6.0–6.5) or BiO-Gel 1.5 m at pH $\leq 7.0$; or c. centrifuge on a linear density gradient, e.g. of 1–30% by weight sucrose, in a preparative ultracentrifuge in an SW-27 rotor at 25,000 rpm for 12 hours. When using a zonal centrifugation with the same gradient (20° C.) at 10,000 rpm large amounts of homogeneous populations of micelles and vesicles can be centrifuged.

d. Purified by DEAE-Cellulose column chromatography at pH 5.0–6.5 (pH $\leq 7$), e.g. by phosphate gradient (linear from 0.01M $KH_2PO_4$/0.01M $K_2HPO_4$, pH 6.5 up to 0.05M $KH_2PO_4$/0.05M $K_2HPO_4$ in the total elution volume of 1000 ml) until the desired population of micelles or vesicles has been obtained.

It is thus possible to obtain the desired homogeneous populations of micelles or vesicles along with their included pharmaceutical active substances in the form of reproducible constant molecular weights and geometrical configurations. This makes it possible to separate quantitatively monomers of the tensides from the micelles and from unincluded pharmaceutical active substances.

Preparation of the Homogeneous Micellar Solution in Aqueous Phase

The aqueous phase may be pure water. As a rule, however, an aqueous solution of an electrolyte is used. For example, an aqueous solution of NaCl or $CaCl_2$ ($MgCl_2$) may be used. In addition, active pharmaceutical agents of the aforementioned type may be introduced and are then dissolved in micellar manner, possibly subjecting them to sonic radiation.

Most processes are restricted to an encapsulation of hydrophilic substances. It is possible with the present invention to include in micelles hydrophobic, for example lipophilic, inorganic ($(Hg)CN_2$) and organic active substances (amphotericin B). Also, hydrophilic anions of pharmaceutical significance, for example salicylate, can be included at the external surface of the micelle depending upon the nature of the N-tenside (in particular of formula II).

The invention can be employed to include either hydrophilic or lipophilic substances or both substances. In the case of hydrophobic active substances the latter are then dissolved with the N-tenside of the formulas I and II in a glycerol/ethanol mixture consisting of 15% by weight glycerol, 15% by weight ethanol and 70% by weight water or 50% by weight ethanol and 50% by weight water, possibly shaken or ultrasonically treated and thereafter diluted to the aqueous phase with a content of glycerol/ethanol of at the most 15 g glycerol, 5 g ethanol in 100 g water. Subsequent gel permeation chromatography or preparative HPLC can remove undesirable material and provide a homogeneous isotropic solution. Whereas hydrophobic substances are made mainly via an organic phase (50%) and subsequent dilution (water), hydrophilic pharmaceutical active substances are preferably used in the aqueous liquid employed for dispersing the micellar solution. If necessary any unaccepted active substances can be removed from the dispersion using known techniques, e.g. dialysis, centrifuging, gel permeation chromatography.

The form and size and the degree of hydration of the micellar solutions of the N-tensides depends inter alia on $y^-$ and to a lesser extent on the structure of the heterocycle although no doubt also on the hydrophobic chain length $(CH_2)_x$. Thus, for example, in the presence of $Br^-$ or salicylate$^-$ large rod-shaped micelles of hexadecylpyridinium can be obtained of an order of magnitude of $L=10,000$ Å and a diameter of 100–500 Å whereas in the presence of chloride micelles of the order of magnitude of 50–100 Å are obtained in aqueous solution. In this case the shape and size of the micelle defines the concentration of the (micellar) active substance to be encapsulated and thus behaves in a manner opposite to liposomes.

The advantage of the invention compared with the encapsulation with liposomes resides in 1. the density of these N-tensides which due to the previously aforementioned forces cannot liberate the micellarly bound pharmaceutical active substance and 2. the control of the form and size of the micelles by $y^-$ and thus the control of the absorptive capacity for hydrophobic and hydrophilic active substances without major incisive influence of the heterocycle on the cmc.

The resulting formation of the small and large micelles of the N-tensides in aqueous phase can be proved by physical measuring methods, e.g. with freeze-dried samples ("freeze fracture") under an electronmicroscope or by X-ray small angle scattering, dynamic light scattering, nuclear resonance spectroscopy ($^1$H, $^{13}$C and $^{31}$P) and by transmission electronmicroscopy. FIGS. 2 and 3 show for example electronmicroscope pictures of micellarly included Hg(CN)$_2$ in hexadecylpyridinium and benzethonium chloride.

In the nuclear resonance spectrum sharp signals with weak line width are obtained providing an indication of the formation of micelles with a diameter less than 600 Å. Sharp signals at δ about 0.89 ppm (—CH$_3$), δ about 1.28 ppm (—CH$_2$—) and δ about 3.23 ppm (—N—(CH$_3$)$_2$ are for example characteristic of the micelles of the N-tensides of the general formula I and II. For included active materials in these micelles of the N-tensides a methyl signal at δ about 0.87 to 0.89 ppm is characteristic but is split into a triplet and has a substantially smaller line width than the methyl signal which occurs as a singlet at δ=0.89 ppm but which originates however only from the micelle.

These aqueous phases containing the micelles according to the invention with included active substances are administration systems which possibly after concentration, e.g. by ultrafiltration, ultracentrifugation or lyophilization with subsequent dissolving in an aqueous phase, are suitable for oral (p.o.) or local administration.

In the case of oral administration the micellarly bound pharmaceutical active substances of the N-tensides of the aqueous phase are mixed with pharmaceutically neutral diluents or carriers or with usual additives, for example coloring agents or flavouring agents, and administered as syrup or in the form of capsules.

Thus, a homogeneous isotropic micellar aqueous solution consists preferably of an N-tenside of the formula II and I with an antiviral active substance, in particular Hg(CN)$_2$, or ZnSO$_4$, ZnEDTA, idoxuridine, 5-ethyl-2'-deoxyuridine or trifluorothymidine, amantadine, rimantadine (α-methyladamantane) and viderabine (9-β-arabino <1,4>-adenine) and ribavirin (1-β-D-ribofuranosyl-1,2,4-triazole-3-carboxamide) and with 2,6-di-amini-cubane 1,1':3,3'-bis-cyclobutane or singly substituted 2,6-di-amino compounds (CF$_3$, Cl, OCH$_3$) dispersed in the presence or absence of glycerol/ethanol (20° C.; ionic strength <0.2M).

A homogeneous isotropic micellar aqueous solution exists of an N-tenside of the formula II and/or formula I preferably with an antifungal active agent, preferably with 5-fluorocytosine, clotrimazole, econazole, miconazole or oxyconazole (Z form) and with amphotericin B, nystatin and ZnO.EDTA as inorganic antifungal active substance, and Hg$_2$(CH)$_4$Hg(CN)$_2$ is present here as polymer, the dimer being the basic structural unit (dispersed in aqueous solution).

A homogeneous isotropic aqueous solution consists of an N-tenside of the formula I and/or of the formula II preferably with an antineoplastic active agent, in particular 5-fluorocyanide, Hg(CN)$_2$.4 (ascorbate or acetylacetonate), azauridine, cytarabine, azaribine, 6-mercaptopurine, deoxycoformycine, azathioprine, thioguanine, vinblastine, vincristine, daunorubicine, doxorubicine dispersed in the presence or absence of glycerol/ethanol.

A homogeneous isotropic aqueous solution consists of an N-tenside mainly of the formula II or the formula I preferably with amino glycosides such as canamycin, gentamycin, neomycin etc. or tetracyclines, chloramphenicol or erythromycin as bacteriostatic (gramposi- tive) or clindamycin (against non-sporiferous anaerobic bacteria) or rifampicin as bactericidal substance, and bacitracin, tyrotricin and polymycins, dispersed in the presence or absence of glycerol/ethanol.

The homogeneous mixture can also be subsequently dispersed in gels on the basis of alginate, hydrogel structures such as Sephadex agarose, propyl cellulose, propylhydroxy cellulose, in the presence of DMSO, glycerol, the pharmaceutical active agents being contained micellarly in the desired concentrations.

Dispersing is effected for example by vibration, stirring or ultrasonic treatment of the aqueous phase containing the previously made homogeneous isotropic mixture. The formation of the micellar structures with the included active substances, pH≦7.0, 20° C., takes place spontaneously, i.e. without appreciable additional energy supply from outside, and at a high rate. The concentration of N-tenside of the formula I and II and the included compound can be increased if the cmc is exceeded by at least tenfold in the aqueous phase at constant chemical potential and temperature.

The cmc is a variable quantity for the amount of the monomers of the N-tensides which can be dissolved in a specific volume of water employing pH fluctuations ≦7.0. The cmc, which according to the invention does not depend very much on the nature of the counter ion, which only governs the form, since the operation is carried out far above the cmc, can be determined by electrochemical methods (conductivity, potentiometry) by measuring the transfer cells in conjunction with the counter ions, the surface tension, vapor pressure reduction, freezing point reduction and osmotic pressure, measuring the density, refractive index, the elastic and inelastic light scattering (diffusion coefficients, Stokes radius) and the viscosity, and by gelfiltration and X-ray small angle scattering measurements. Nanoseconds fluorescence and the measurement of the fluorescence polarization permit additionally determinations of the pharmaceutical active substances included by the N-tensides of the formula I and II, for example by ZnEDTA or Hg(CN)$_2$ as quenchers and amphotericin B as intensifier. Positronium elimination measurements on these micellar solutions described with the included active substances also allow information to be gained on the amount (concentration) of the included pharmaceutical active substance in dependence upon the nature and concentration of y$^-$.

Aqueous phases having a pH value >7.0 are centrifuged after the dispersion. The neutralization to pH≦7.0 is necessary to prevent a destruction of the heterocycle in formula I and of the active substance and/or the micelles under basic conditions. Physiologically common and compatible acids are for example diluted aqueous mineral acids and hydrochloric acid, sulfuric acid or phosphoric acid or organic acid, for example low alkane acids such as acetic acid or propionic acid. Usually the aqueous phases of the cationic N-tensides of the formul I and II react acid to neutral but they can be exactly set to pH values between 3 and 7.0 by Soerensen buffers or organic inert buffers such as HEPES, MOPS or MES.

Preparation of the Homogeneous Micellar Solution in Non-aqueous Phases

The choice of the respective solvents depends on the solubility of the particular pharmaceutical active substance. Suitable solvents are for example methylene chloride, chloroform, alcohols, e.g. methanol, ethanol and propanol, low alkane carboxylic acid esters (acetic ethyl ester), ether or mixtures of these solvents. After preparation of the micellar solution and adding the pharmaceutical active substance, dissolved in the organic solvent, said organic solvent is removed either by the methods a)-d) mentioned above or by blowing off with inert gas, e.g. helium or nitrogen.

EXAMPLE 1

10 mg hexadecylpyridinium chloride is dissolved in 100 ml of a water/ethanol mixture (85:15; w/w) at 25° C. whilst stirring and 10 ml glycerol added. The pH value should be 6.5 but can be set with HCl to said value or to another pH value (=7.0). This solution is then cooled to 20±0.01° C. and then subjected to an ultrasonic treatment (Bronson Sonifier, Massachusetts, U.S.A.) for two minutes at 10 watt. The formation of the micelles is determined by measuring the diffusion coefficient by means of inelastic light scattering and the Stokes radius ($R_H$) then calculated by the equation $$D^{o}_{20,w} = \frac{k_B \cdot T}{6\pi\eta_o \cdot R_H} \quad (1)$$

$T = t° + 273$
$\eta_o$ = viscosity of the solvent
$k_B$ = Boltzmann's constant
$D^{o}_{20,w}$ = diffusion constant In the presence of Cl⊖ as Y⊖ it should not be greater than 50 Å and in the presence of Br⊖ it should not be greater than 1000 Å. To form microemulsions of micelles of specific size a film-like residue obtained by evaporating the aforementioned solution in a rotary evaporator is dispersed at room temperature (20° C.) in 1/10 of the original volume by 10-minute vibrating. A slightly opalescent aqueous solution is obtained. For inclusion of a pharmaceutical active substance, e.g. 5-fluorouracil, cytarabine or idoxuridine, these substances, which are sparingly soluble in water, can be introduced directly, i.e. in solid form or as aqueous suspension. Thus, for example, trifluoruridine, 1.0–3.0 mg, is added at 20° C. whilst stirring either as microemulsion (suspension) or directly to the aqueous micellar solution of the quaternary ammonium base. A quantitative dosing of the aforementioned nucleoside and adenine nucleoside compounds can be achieved also by dialysis:

The micellar solution of the aforementioned concentration (buffered, unbuffered, pH≅6.0, ionic strength variable, T=293° K.) is introduced into a dialysis hose (the company Servant or Pharmacia), sealed and under constant stirring at room temperature dialyzed for 2 hours against a set solution of pH≦7.0 which contains the aforementioned pyridine or/and adenine nucleoside of specific concentration. The decrease in the extinction at 260 nm with the time of the dialysis permits a check of the micellar incorporation of the aforementioned active substances into the hydrophobic core of the hexadecylpyridinium chloride (Tab. 1).

TABLE 1

| Experiment | $R_H$ (Å) (± 5.0Å) | (20° C., pH 5.5) Concentration Trifluorouridine mg/100 ml | Idoxuridine mg/100 ml | Yield (%) | |
|---|---|---|---|---|---|
| 1 | 45,0 | 5 | 7,5 | 95 | 95 |
| 2 | 45,0 | 7,5 | 10,5 | 95 | 98 |
| 3 | 50,5 | 10,0 | 12,5 | 94 | 98 |
| 4 | 60,0 | 12,0 | 15,0 | 96 | 98 |
| 5 | 60,0 | 15,0 | 17,0 | 96 | 97 |
| 6 | 65,0 | 17,0 | 20,0 | 96 | 96 |

TABLE 1-continued

| Experiment | $R_H$ (Å) (± 5.0Å) | (20° C., pH 5.5) Concentration Trifluorouridine mg/100 ml | Idoxuridine mg/100 ml | Yield (%) | |
|---|---|---|---|---|---|
| 7 | 71,5 | 20.0 | 21,5 | 100 | 98 |
| 8 | 75,0 | 25.0 | 23,0 | 100 | 100 |
| 9 | 75,0 | 30.0 | 24,0 | 100 | 100 |
| 10 | 78,0 | 50.0 | 30,0 | 100 | 100 |

The resulting formation of small micellar structures in the aforementioned solution can be detected in the NMR spectrum by the signals $\delta=1.25$ (methylene), $\delta=0.86$ (methyl). By incorporation of the aforementioned pharmaceutical active substances, depending on the saturation in the hydrophobic core, a displacement of $\delta=1.25$ (methylene) takes place but not $\delta=0.86$ (methyl).

The size of the micelles can be determined easily by inelastic light scattering according to formula (1) (Table 1). The size and the shape for obtaining a homogeneous and monodisperse solution can also be achieved by HPLC chromatography, gelpermeation and agarose chromatography.

FIG. 5 shows, by curve no. 1, the temperature dependence of Stokes' radius of 8-ketohexadecylpyridinium chloride with micellarly included Z-miconazole, and by curve no. 2, the temperature dependence of Stokes' radius of 8-ketohexadecylpyridinium chloride with micellarly included Z-miconazole+Hg(CN)$_2$.

A concentration of the micelles thus made can be achieved by pressure dialysis by means of fiberglass cartridges of defined pore size. It is also possible to achieve not only a defined concentration of pharmaceutical active substance but also to keep constant the micelle size, aggregation rate, hydration (solvation) because no fusion of the micelles ("intermicellar growth") occurs. This means that the number of micelles pro volume unit increases with their included pharmaceutical active substance (concentration of hydrodynamic particles with the same molecular weight) but not the aggregation rate or the number of any monomers present which are separated by ultrafiltration.

EXAMPLE 2

Analogously to example 1 per test 15 mg benzethonium chloride is dissolved in 150 g water/ethanol (85/15; w/w) at 25° C. whilst stirring and 0.5 ml glycerol added. The pH value is normally between 4.8 and 5.5. To obtain a clear non-opalescent solution the latter is subjected to an ultrasonic treatment at 25° C. for two minutes at 20 watt. The formation of the micelles of defined size is completed after cooling to 20° C. after five minutes. For incorporation of the aforementioned antiviral active substances, e.g. trifluorouridine, idoxuridine, the procedure given under example 1 can be adopted.

For inclusion of miconazole (Z form) the micellar solution thus made is dispersed in the presence of miconazole of specific concentration, subjected to ultrasonic treatment (2 minutes), then chromatographed over agarose, and the micelles can be eluted with the hydrophobically included Z-miconazole as uniform monodisperse peak. The size and concentration of active substance can be determined by inelastic light scattering and UV spectroscopy. FIG. 6 shows, by curve no. 1, the temperature dependence of Stokes' radius of benzyldimethyl{2-[2-(p-1,1,3,3-tetramethylbutyl-p,p'-dimethyl-phenoxy)ethoxy]ethyl}-ammonium chloride with micellarly included viderabine; and by curve no. 2, the temperature dependence of Stokes' radius of benzyldimethyl{2-[2-(p-1,1,3,3-tetramethylbutyl-p,p'-dimethyl-phenoxy)ethoxy]ethyl}-ammonium chloride with 5-trifluoro-thymedine.

Analogously to example 1 10 mg benzethonium chloride and a desired concentration of Z miconazole can be dissolved each in 5 ml of a chloroform methanol (3:1) mixture, then concentrated by hollow fiber pressure dialysis and thereafter dispersed in water or a desired buffer. A clear aqueous solution is obtained which comprises micelles of the order of magnitude of $R_H = 60-80$ Å in the presence of $Cl^\ominus$ or $R_H = 100-1000$ Å in the presence of salicylate with included active substance.

By addition of 1% (g/g) alginate and/or 5% (g/g) dimethylsulfoxide thixotropic gels can also be made with the aforementioned included active substances. By increasing the benzethonium chloride concentration, along with the included active substances, up to 2% (g/g) effective oils can also be prepared.

EXAMPLE 3

Analogously to examples 1 and 2 the counter ions $Y^\ominus = Cl^\ominus$, $Br^\ominus$ etc. can be exchanged after preparation according to the process by ion exchange chromatography on DEAE Sephadex A 50 or DEAE Sepharose or by dialysis exchange for the respective or desired counter ion $Y^\ominus$.

a) An aqueous micellar solution made by example 1 and 2 is brought to pH = 7.0 with 0.01N NaOH (20° C.). This can be done either by titration or dialysis against 0.01N NaOH for 10 hours. Subsequently, dialysis is carried out against 1N fumarate or maleate solution, for which the Na salts of fumaric or maleic acid can be used. The dialysis is completed after 12 hours. A loss of antiviral active substances mentioned above does not occur.

b) An aqueous micellar solution, pH 6.0, made by example 1 and 2 is eluted on a DEAE Sephadex A 50 (1.0 × 100 cm) column previously charged with a buffered (0.01M $K_2HPO_4$ buffer) 0.1N salicylate solution with a flow rate of 10 ml/30 min (20° C.). The excess salicylate is removed by dialysis against a large excess water/ethanol/glycerol (90/5/5; g/g) from the column eluate. The DEAE Sephadex A 50 chromatography can also be carried out under pressure by the countercurrent method with the same solvent system. With exchange chromatography (DEAE Sephadex A 50, DEAE Sepharose 2B, 5B, DEAE-Cellulose, spherical) a homogeneous peak is obtained which can be analyzed by the criteria shown in examples 1 and 2. DEAE Sephadex and DEAE Sepharose have the advantage that considerable quantities of micellar quaternary ammonium bases can both be purified and examined for monodispersity.

EXAMPLE 4

Analogously to example 1 a micellar solution of hexadecylpyridinium chloride is prepared with the following pharmaceutical active substances:
100 g solution contain:

| | |
|---|---|
| hexadecylpyridinium chloride | 0.10 g |
| atropine hydrochloride (±) | 0.002 g |
| zinc II chloride | 0.004 g |

-continued

| | |
|---|---|
| glycerol | 10.0 g |
| ethanol | 4.894 g |
| water | 85.0 g |
| pH | 6.2 |

This preparation has a hydrodynamic radius of 35.0±5.0 Å and an aggregation rate of N = 35 for a molecular weight of the monomer of hexadecylpyridinium chloride of 393.0. Each micelle of this diameter contains on an average 100 μg zinc and/or 50 μg atropine (−).

FIG. 7 shows the variance in the hydrodynamic radius $R_H$ of this preparation. In FIG. 7, the heavy solid line represents N-dodecyl-5-carboxamidepyridinium fumarate at pH 5.8, the light solid line represents N-dodecyl-5-carboxamidepyridinium fumarate at pH 5.8 plus atropine-HCl, the light dashed line represents cetylpyridinium chloride at pH 5.5 plus $Hg(CN)_2$ atropine-HCl, and the heavy dashed line represents cetylpyridinium chloride at pH 5.5. It also shows the separation according to the invention of the racemate atropine into the optical antipodes, e.g. hyocyamine (−). The micellar size distribution is not changed by ZnII chloride.

FIG. 8 shows the variance in the hydrodynamic radius $R_H$ of the N-hexadecyl-4-methylpyridinium chloride (dashed line) and N-hexadecyl-4-methylpyridinium chloride + atropine HCl (solid line).

EXAMPLE 5

5 mg 4-(17-tritriacontyl)-N-methylpyridinium chloride and 1-2.0 mg amphotericin B is dissolved in 10 ml of a chloroform/methanol mixture (2:1) under nitrogen at 25° C. and this solution is evaporated in a rotary evaporator. The film-like residue is shaken in 5 ml distilled water for five to 10 minutes. This solution is thereafter subjected to ultrasonic treatment for three minutes until it is no longer opalescent. Depending on the requirements, this solution can subsequently be brought to the pH value of 5.5-6.5 by adding 0.5 ml of a five-times concentrate of phosphate-buffered isotonic saline solution.

The solution made in this manner is introduced into a stirred ultrafiltration cell (e.g. Amicon$^R$) which is provided in place of the ultrafilter with a straight-pore filter having a pore diameter of 0.05 μm, filtered in the absence of $Me^{2+}$ ions ($Me^{2+} = Ca^{2+}$, $Mg^{2+}$) so that the volume in the cell does not drop below 30 ml. This results in vesicles of a uniform size of < 50000 Å.

The shape, size and molecular weight distribution can be determined as in examples 1 and 2. The pyridinium amphiphile is prepared from the corresponding iodides with silver chloride in 10% (v/v) ethanol/water. The colorless crystals have an Fp = 64° C. (recrystallized from acetone) and crystallize with one molecule of water.

1 H-NMR ($CDCl_3/Me_4Si$): δ0.93, (6H, t, J∼4 Hz), 1.28 (60H, m), 2.8 (1H, q, J<2 Hz, not resolved), 4.75 (3H, s), 7.7-9.5 (4H, m). An $H_2O$-dependent signal at δ4.4 is characteristic.

Anal. calc. for $C_{39}H_{74}NCl \cdot H_2O$ (MW 610.50) C 76.72; H 12-55; Cl 5.81; found: C 76.53, H 12.43; Cl 5.78.

EXAMPLE 6

Analogously to example 5 10 mg 3.5-bis[(n-hexadecylonxy)carbonyl]-N-methyl-pyridinium chloride (Fp = 102.5°) with 2.0 mg amantidine or rimantidine is dissolved in 10 ml of an ethanol/water mixture (1:2) under nitrogen at 20° C. After ultrasonic treatment (5 min., 20° C., 10 watt) the vesicles formed with their included active substances amantidine or rimantadine can be separated in a Sepharose 2B by size and molecular weight to obtain a homodisperse solution of vesicles with small molecular polydispersity. In the $^1$H-NMR spectrum the clear signals of methylene ($\delta = 1.28$) and methyl protons ($\delta = 0.86$) can be seen.

These unilamellar vesicles formed in examples 5 and 6 can be rendered visible under an electron microscope. For this purpose the vesicle dispersion is first subjected to the freeze-fracture method. This can also be done by negative straining by means of the two drop method on Formvar or carbon grids. It is additionally possible by these two techniques to render visible any populations of vesicles.

The method of inelastic light scattering used under examples 1 and 2 makes it possible to determine the form and size of these vesicles and their included pharmaceutical active substances (FIG. 9). Curve 1 in FIG. 9 represents the temperature dependence of Stokes' radius of 3,5-bis[(n-hexadecyloxy)carbonyl]-N-methyl-pyridinium chloride with lamellarly included amantidine, not ultrasonically treated. Curve 2 represents the temperature dependence of Stokes' radius of 3,5-bis[(n-hexadecyloxy)carbonyl]-N-methyl-pyridinium chloride with lamellarly included amantidine, ultrasonically treated. Curve 3 represents the temperature dependence of Stokes' radius of 3,5-bis[(n-hexadecyloxy)carbonyl]-N-methyl-pyridinium chloride with lamellarly included rimantadine, ultrasonically treated.

3.5-bis[(n-hexadecyloxy)carbonyl]-N-methyl-pyridinium chloride, Fp = 102.0°–102.5° (acetone). $^1$H-NMR (CDCl$_3$/Me$_4$Si): $\delta$0.85 (6H, t, J 5 Hz), 1.30 (56H, m), 4.40 (4H, t, J<7 Hz), 5.03 (3H, s) 9.20 (1H, t, J<2 Hz), 10.00 (2H, d, J<2 Hz).

Analyt. calc.: C$_{40}$H$_{72}$NO$_4$Cl(MW 666.47): C 72.10, H 10.88, C 15.32; found: C 71.44, H 10.84, Cl 5.23.

EXAMPLE 7

3 ml gentamycin is dissolved analagously to examples 1 and 2 or in one of the tensides named in Table 3 of the quaternary ammonium bases in 1 ml of chloroform/methanol mixture (3:1) and this solution evaporated until a thin film is formed. This film is then dispersed in 10 ml water. Subsequently, the solution can be set to the desired pH>3<6.5 with buffer. A clear solution is obtained.

This clear solution contains depending on the tenside used according to Table 3 a monodisperse distribution of micelles charged with gentamycin in the desired order of magnitude and yield (FIG. 10). Curve 1 in FIG. 10 represents the temperature dependence of Stokes' radius (hydrodynamic radius) of N-cetyl-4-methyl-imidazolium chloride with micellarly included rimantadine measured by inelastic laser light scattering. Curve 2 represents the temperature dependence of Stokes' radius of N-hexadecyl-5-carboxamide-chloride with micellarly included 5-fluorocytosine. Curve 3 represents the temperature dependence of Stokes' radius of 2,4-dihydroxy-5-methyl-hexadecylpyridinium chloride with micellarly included gentamycin.

EXAMPLE 8

A micellar solution of hexadecylpyridinium chloride (cetylpyridinium) is prepared analogously to example 1 (20° C.) and contains the following active substances:

100 g solution contain:

| | |
|---|---|
| cetylpyridinium chloride | 0.10 g |
| atropine hydrochloride (±) | 0.004 g |
| mercury II cyanide | 0.004 g |
| glycerol | 10.892 g |
| ethanol | 5.0 g |
| water | 84.0 g |
| pH, T = 293° K. | 5.7 |

This preparation has according to the invention a hydrodynamic radius of 35.0±10.0 Å and an aggregation number, n, of 35 with a molecular weight of the monomer of cetylpyridinium chloride of 393.0. Each micelle of this diameter contains on an average 5 $\mu$g Hg(CN)$_2$ and/or ~5.0 $\mu$g atropine (−) (FIG. 12). In FIG. 12, the light line represents hexadecyl-pyridinium-chloride, 0.2M NaCl, pH 5.8, and the heavy line represents hexadecyl-pyridinium-chloride, 0.2M NaCl plus Hg(CN)$_2$, pH 5.8.

This preparation is a homogeneous solution which contains micelles of the order of magnitude of 30–50 Å ($R_H$). It inhibits the growth of influenza A virus as shown by the following Table 6 (FIG. 11). Curve 1 in FIG. 11 represents the temperature dependence of Stokes' radius of N-hexadecylpyridinium chloride and micellarly included Hg(CN)$_2$, not ultrasonically treated. Curve 2 represents the temperature dependence of Stokes' radius of N-hexadecylpyridinium chloride and micellarly included Hg(CN)$_2$, ultrasonically treated.

TABLE 6

| Inhibitor[a] | Titration of infection[b], Plaque forming units | Inhibition[c] |
|---|---|---|
| 1-adamantaneamine HCl | 2 × 10$^6$ | −1.11 |
| Aqueous Hg(CN)$_2$ solution | 1 × 10$^6$ | −1.30 |
| Cetylpyridinium chloride | 1.5 × 10$^8$ | −0.11 |
| Preparation according to example 8 | 2 × 10$^5$ | −1.45 |
| Check | 2 × 10$^8$ | — |

[a]Inhibitor concentrations are added in the in vitro cell cultures of 100 $\mu$M.
[b]The plaque assay was carried out in accordance with K. Tobita. A. Suginire. C. Enamote and M. Fusiyama. Med. Microbiol. Immunol.. 162. 9 (1975) on renal epithelial cells (dog. MDCK) in the presence of trypsin.
[c]The inhibition is given as the negative decadic logarithm of the quotient of the plaque forming units in the presence of the inhibitor to that without inhibitor: $^{10}$log (pfu/ml of the inhibitor/(pfu/ml check)).

FIG. 7 shows the variance in the hydrodynamic radius $R_H$, of this preparation. It also shows the separation described above according to the invention of the atropine into its optimum antipodes in the presence of Hg(CN)$_2$.

EXAMPLE 9

5 mg of an N-quaternary ammonium base given in Table 3 (usually No. 1, 2 or 4) and 2.0 mg 5-fluorouracil or 1.5 mg 5-fluorodeoxyuridine is dissolved in 10 ml of a chloroform/methanol/ether mixture (3/1/1) and this microemulsion dispersed by vigorous shaking at 25° C. for two hours. There are two methods for the further processing:

a) The suspension is evaporated to form a thin film (under N$_2$ and UV protection). The film-like residue is then dispersed in water or buffer, for example 0.01M to 0.001M KH$_2$PO$_4$, set to pH 4.5–6.5. After previously subjecting this partially opalescent solution to ultrasonic treatment (10 watt, 2 min) to increase the yield, the clear micellar solution is subsequently separated on a Bonder Pack I-250 or an RP 18 column by high-pressure liquid chromatography (HPLC) from any monomers present and any unincluded pharmaceutical active substances. In a stirred ultrafiltration cell (Amicon ®) concentration is carried out with a filter of polycarbonate with a pore diameter of 0.015 μm.

b) 10% (g/g) dimethylsulfoxide (DMSO) and 2.5% (g/g) alginate are stirred into this suspension at 25° C. The resulting gel forms spontaneously. In the X-ray small angle diagram a uniform spacing of d=125 Å is found which is very different from alginate gels (d=25.45 Å). The gel has thixotropic properties and becomes liquid at 45° C. Reformation of the gel takes place at 42° C. and its constant rheological parameters are achieved after 2 hours at 20° C. and 37° C. respectively.

The final concentrations per 100 g pharmaceutical preparation are as follows:

| 100 g solution contain: | |
|---|---|
| a) N+-tenside (Table 3, No. 4) | 0.01 g |
| 5-fluorodeoxyuridine | 0.10 g |
| glycerol | 11.89 g |
| water | 88.00 g |
| T = 293° K., pH = 5.5 | |
| b) N+-tenside (Table 3, No. 2) | 0.05 g |
| 5-fluorodeoxyuridine | 0.05 g |
| dimethylsulfoxide | 10.00 g |
| alginate | 2.50 g |
| water | 86.50 g |
| T = 293° K., pH = 5.5 | |

EXAMPLE 10

15 mg (0.02 mMol) benzethonium chloride and 2 mg 2-acetamido-4-morpholino-1,3,5-triacine are dissolved in 30 ml of a water/ethanol mixture (80:20 or 90:10) at 20° C. under ultrasonic treatment in 0.01M $K_2HPO_4$, pH 6.5, under an $N_2$ stream. An opalescent aqueous phase is obtained. By separating the reversed micelles from the micelles in aqueous phase on a Sepharose 2B column (1.5×100 cm) a uniform monodisperse micelle formation is obtained having an average hydrodynamic radius of 50 Å. The chromatograph solution can be concentrated as in example 9 by an ultrafiltration. The solution is stabilized by using 5% (w/w) glycerol or adding 2% (w/w) salicylate. The solutions thus made do not change their hydrodynamic radius, their partially specific volume or molecular weight distribution in the temperature range of 15°–45° C.

100 g solution contain:

| benzethonium chloride | 0.15 g |
|---|---|
| 2-acetamido-4-morpholino-1,3,5-triazine | 0.006 g |
| salicylic acid | 0.05 g |
| glycerol | 5.00 g |
| water | 94.894 g |
| T = 239° K., pH = 5.5 | |

EXAMPLE 11

30 mg (0.020 mMol) 3.5-bis[(n-hexadecyloxy)carbonyl]-N-methylpyridinium chloride and 1.0 mg (~0.005 mMol) polyoxin A are dissolved in 10 ml 0.01M $KH_2PO_4$, pH 6.5, at 20° C. containing 1 ml of a mixture of tert.butanol/methanol/ethanol (2:1:1). The solution is ultrasonically treated (20 watt, 5 min) in an ice bath at 0° C. and thereafter made up to 20 ml with phosphate buffer, pH 7.0. The clear non-opalescent solution is chromatographed on a Sepharose 2B column at pH 7.0 in the presence of phosphate at room temperature. The vesicles doped with the pharmaceutical active substance are concentrated in an ultrafiltration cell (Amicon ®) with a pore diameter of 0.05 μm under slight excess pressure. After passage of 0.3–0.5 ml filtrate all the vesicles with a diameter of 350 Å are separated and the supernatant dispersion can be introduced into ampoules and used for therapeutic tests. FIG. 13 shows the inhibition of chitin synthetase in digitonin-treated cells (Saccamyces cerivisiae and Candida albicans) after addition of this preparation in dependence upon the polyoxin A concentration. In FIG. 13, the points represented by squares indicate data taken with polyoxine A, the points represented by triangles indicate data taken with polyoxine A plus $Hg(CN)_2$ (D4), and the points represented by circles indicate data taken with polyoxine A plus $ZnCl_2$ (gluconate) (D4).

EXAMPLE 12

Analogously to example 2 10 mg $Hg(CN)_2$ and 40 mg Na ascorbate at pH 7.0 are dissolved in 10 ml phosphate buffer. The suspension is subjected to an ultrasonic treatment at 0° C. for 5 min, slowly heated to 20° C. and centrifuged to a 10% (w/w) linear glycerol gradient in a preparative ultracentrifuge at 1000 xg for 6 hours (20° C., Polyalomer tubes). After the dripping out the UV-active fractions are united and concentrated in an Amicon flow cell and subsequently analyzed for Hg and ascorbate (HPLC; mobile solvent $CH_3OH/H_2O$ (50/50) Hg detection with Na-diethylthiocarbamate, hexadecylpyridinium Cl, e.g. by UV detection at 251 nm; Hg $(CN)_2$ ascorbate by UV detection at R=245 nm at pH 2.0 and R=265 nm at pH 7.0). These micellarly included $Hg(CN)_2$ ascorbate complexes (MW—1.500) have in accordance with Table 5 the following representative inhibitor concentrations with respect to B. subtilis DNA polymerase III.

TABLE 5

| Nr. | Tensid | $Hg(CN)_2$ $K_i$, μM | $Hg(CN)_2$ Ascorbat $K_1$, μM | Competitive with |
|---|---|---|---|---|
| 1 | Hexadecyl-pyridinium-Cl⊖ | 7,9 | 15,3 | dGTP |
| 2 | Hexadecyl-pyridinium-Cl⊖ | | | dGTP |
| 3 | Benzethonium-Cl | 33,1 | 12,0 | dATP |
| 4 | Benzethonium-Cl | | | dATP |
| 5 | 8-Keto-hexadecyl-pyridinium-Cl | 0.4 | 0,05 | dGTP |
| 6 | 8-Keto-hexadecyl-pyridinium-Cl | 2,5 | 7,5 | dGTP |
| 7 | 3,5-bis (n-hexadecyloxy-carbonyl-N-methyl-pyridinium-Cl | 2,0 | 9,2 | dGTP |
| 8 | 4-(17-tritriacontyl)-N-methyl-pyridinium-Cl | 4 | 10,1 | dGTP |
| 9 | acc. to Table 3 Nr. 9 | 9 | 0,5 | dGTP |
| 10 | acc. to Table 3 Nr. 10 | 0,1 | 7,9 | dATP |

The inhibitor concentrations are given in 50% of the complete inhibition. The assay which was used is that according to Clements, J; D'Ambrosio, J; Brown, N. C; J. Biol. Chem. (1975) 250, 522 and Wright, G. E.; Brown, N. C; Biochem. Biophys. Acta (1976) 432, 37.

Pharmacodynamic Tests

The significance of highly reactive oxygen molecules (superoxide radicals $.O_2$, peroxides $H_2O_2$, hydroxyl radicals. OH, singlet oxygen $^1O_2$) in the inflammatory process is known (cf. e.g. McCord, J. M., K. Wong; Phagocytosis-produced free radicals: roles in cytotoxicity and inflammation. In: Oxygen Free Radicals and Tissue Damage, Excepter Medica, Amsterdam-Oxford-New York, 1979, 343-360; Allgemeine und spezielle Pharmakologie, Herg. W. Forth, D. Henschler, W. Rummel, Biowissenschaftlicher Verlag, 1983). They arise inter alia in the phagocytosis by activated leucocytes (monocytes, macrophages, polymorphonuclear, neutrophilic granulocytes) and can be used for killing exogenous cells and bacteria, bacilli, etc., and for certain viruses when the immunological system and the receptors of the phagocytes specific to IgG or the complementary component $C_3$ are functioning normally. The phagocytizing cells themselves are intracellularly protected from damage by these particularly active forms of oxygen by a system consisting of several enzyme systems.

It has now been found that quaternary ammonium bases of the general formulae I and II

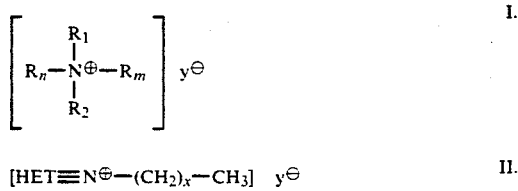

wherein $Y^\ominus$ may be a counter ion both of an inorganic, e.g. $Cl^\ominus$, $Br^\ominus$, $H_2PO_4^-$ or organic nature, e.g. fumarate, malate, salicylate, acetate, propionate, gluconate and alginate and the heterocycle may be both a pyridine, pyrimidine, pyrazine, imidazole, thiazole or purine, but a $\pi$-excess or $\pi$-defective aromatic system, which are all able at $pH \leq 7.0$ to eliminate these oxygen radicals in accordance with the following reaction mechanism:

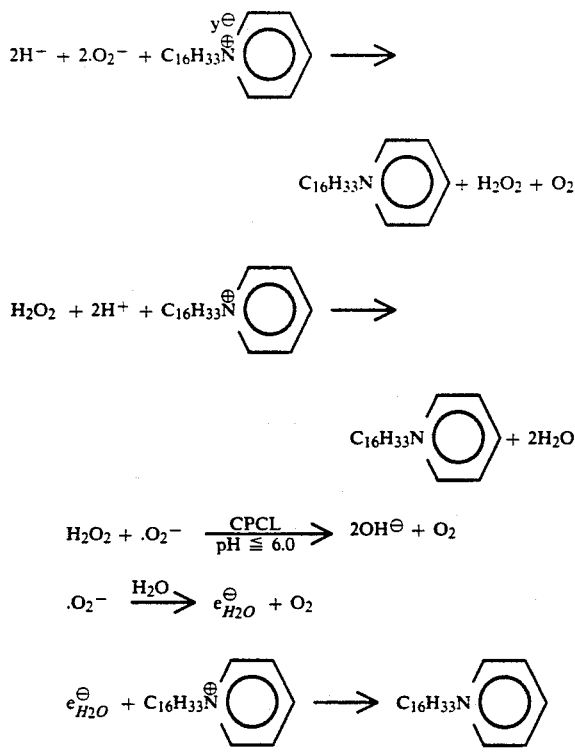

All reactions which take place in the inflammatory range between pH 5.0 and 6.0 require a pH range $\leq 7.0$, which is ensured by the preparations made according to this invention. The resulting aggressive oxygen radicals are intercepted in accordance with the reaction 1-4 by the N-tenside, e.g. cetylpyridinium chloride, as are the resulting hydrated short-life electrons which can originate from collisions of $.O_2^-$ radicals with $H_2O$. As a result the N-tensides in the pH range $\leq 7.0$ according to the invention have a membrane-protective effect so that the inflammation reactions according to a prostaglandin mechanism cannot occur. The high capture rate of $.O_1^-$ radicals in the N-tensides of $k = 5 \times 10^{12} M^{-1}$ and its dependence on the ionic strength, which however can be held constant by adding ethanol/glycerol, is explained by the electrostatic double-layer structure of the quaternary ammonium bases.

Thus, the invention prevents misdirected lytic reactions in which aggressive oxygen radicals participate as pathogenic mechanisms of the inflammatory diseases due to microorganisms and viruses. Thus, inter alia the cytotoxic effect of the resultant products of these aggressive $.O_2^-$ radicals is prevented by the N-tensides according to the invention as shown by the example of cetylpyridinium halide, and inter alia the invention prevents depolymerization of hyaluronic acids, proteoglycanes, collagen fibriles, cytoskeletons, etc., this also applying to mucous and membranous tissues (outer surfaces).

Furthermore, with the preparations made according to the process described it has been found that compounds of the structure I and II reduce the infection of human cells in vitro so that the micellar solutions I and II made according to the invention represent a protection for the cells and their external surface.

It has further been found that this protection is intensified by incorporation of $Hg(CN)_2$, ZnEDTA and/or antiviral, antifungal and antibacterial active substances.

It was found that on incubation of monolayer cell cultures, infected with influenza virus, subgroup $A_2$, of Vero cells and also with *Herpes simplex* virus HSV I-III in vitro more than 60% of the cells are protected from infection by the respective virus.

It has further been found that the effect of the protection by the $N^+$-tensides according to the general formula I and II for monolayer cell functions in vitro is not intensified by the antiviral active substances although the inhibition concentrations of the antiviral active substances are lowered by 30% by cytarabine, idoxuridine, trifluorothymidine, as well as monolayer cells infected with *Herpes simplex* virus type 1 or influenza virus type $A_2$, compared with applications not containing any quaternary ammonium bases according to formula I and II. The combination of $N^+$-tenside according to the general formula I and II thus proved to be the effective virostatic in combination with micellarly bound antiviral active substances (FIG. 4).

It was further found that the $N^+$ tensides according to the general formula I and II intensify the antifungal effect in combination with antifungal active substances such as econazole, clotrimazole and miconazole ($\approx 35\%$) since the $N^+$ base with a suitable counter ion is able to extract cholesterol from the external membrane of the fungus or hyphae to form mixed micelles and is then able to inject the antifungus active substances, which are again bound, into the cell interior of the fungus.

It has further been found that the antifugal effect is intensified tenfold by a mechanism hitherto unknown by amphotericin B and N-tenside of the formula II, preferably hexadecyl-pyridinium bromide, decyl and hexadecyl-1-pyridinium chloride or hexadecyl-4-hydroxypyridinium chloride. This means that in accordance with the invention a substantially smaller active substance concentration of the pharmaceutical agent suffices to achieve the same therapeutical effects.

It has been found inter alia that the fungistatic effect is intensified by micellar incorporation of ZnEDTA and ZnO, in particular also by $Hg(CN)_2$, into the N-tensides of the formula I and II, in particular in the case of hexadecyl-pyridinium chloride and hexadecyl-4-hydroxypyridinium bromide, in particular at concentrations of the inorganic active agents at which said agents themselves are not yet effective.

It has been found that according to the invention the micelles of the N-tensides in the aqueous phase at $pH \leq 7.0$ can micellarly bind therapeutic amounts of benzoylperoxide, which is sparingly soluble in water and alcohol. Thus, for example, 1 g benzoylperoxide can be dissolved in 20 ml benzethonium chloride or in 25 ml hexadecylpyridinium chloride, in particular however in 3-hexadecylbenzothiazonium bromide. On local administration the micellar solution causes at the skin similar peeling effects as Tetrinoin. Due to its additional very bacteriostatic properties, both of the benzoylperoxide and of the N-tenside, this combination according to the invention is particularly suitable in the case of inflammatory forms of acne, e.g. acne comedonica, acne papulo-pustulosa and acne conglobata.

It has been found that the micelles made according to the invention in aqueous phase of the N-tensides, in which $Hg(CN)_2$ or ZnO, $ZnSO_4$, ZnEDTA is micellarly included, in the cell culture irreversibly and virus-specifically inhibit the reproduction of Herpes simplex viruses due to inhibition of the viral DNA polymerase. The non-infected cells remain largely uninfluenced so that the methods according to the invention described for example for hexadecylpyridinium chloride, 3-hexadecylbenzothiazolium bromide (sulfate), including the aforementioned inorganic active substances, lead to a therapeutic agent involving no risk. The astringent properties of $Hg(CN)_2$, ZnO, $ZnSO_4$, ZnEDTA play no part because in the hydrophobic core of the micelles there are no free ions since a) for example $Hg(CN)_2$ (more correctly $Hg_2(CN)$) is undissociated, b) the inorganic active substances are included by their lipophils and c) there is practically no water in the hydrophobic core.

The combined effect, the formation of mixed micelles of the N-tensides according to the general formulas I and II with the membrane effected by the virus and and the phospholipid double membrane of the virus itself and the subsequent antiviral effect on the virus DNA polymerase by the aforementioned inorganic and organic active substances such as 5-ethyl-2'-deoxyuridine and viderabine, analogous to the nucleoside, was detected as illustrated in FIGS. 4a, b.

It was also possible to detect this mechanism in the case of rhino and influenza viruses. Other effects were found, with however smaller active substance concentrations, for 1,1':3,3'-biscyclobutane and for 1,1':3,3'-amine-substituted cubanes.

It was found that the intensified antiviral effect for phospholipid viruses, adeno viruses and Herpes simplex I due to the N-tenside and the micellarly included active substances develop their effect synergistically by the following biochemical mechanisms:

a) Binding to DNA, RNA-forming enzyme systems, unfolding of the polypeptide chain is intensified by the N-tenside (denaturing).

b) Template binding, e.g. daunomycin, adriamycin c) Binding of nucleoside analogs, e.g. the aforementioned ara-CTP-C5'-triphosphate of cytosine arabinoside, azathioprine d) Binding of inorganic active substances, e.g. $Z_nSO_4$, $Z_nO$, $Hg(CN)_2$, wolframic acid antimonates, e.g. $(NH_4)_{18}(NaW_{21}Sb_9O_{86})_{17}$ and $K_{18}(KW_{21}Sb_9O_{86})_{17}$, as well as Hg-substituted cubanes of the aforementioned type. In combination with the antiviral effect of the micellarly included antiviral active substances employing the procedure according to the invention a reduction of the $ED_{50}$ by 20–25% in vitro compared with the pure active substance is noted so that the same molecular biological action can be achieved with an approx. 20% dose by the micellar effect. This applies in particular to micellarly included rubaricine in hexadecyl-pyridinium bromide, hexadecylbenzothiazolium chloride and benzethonium chloride. DNA viruses and Herpes viruses are most sensitive in these examples, in contrast to rimantadine+N-tensides of the formulas I and II, which are primarily effective in vitro against RNA viruses.

It has further been found that the antitumor activity of adenosine-desaminase inhibitors dissolved micellarly according to formulas I and II by the process of the invention, e.g. erythro-9-(2-hydroxy-3-nonyl)-adenine, deoxycoformycin, is intensified tensolf. The same was found for aspartate-transcarbamylase inhibitors; thus, the biosynthesis of pyrimidine was intensified 20-fold by micellarly induced N-(phosphonoacetyl)-aspartate by blocking of the carbamylation of aspartate.

It has also been found that both micellarly included $Hg(CN)_2$, $ZnSO_4$, ZnO or ZnEDTA, as also 5-trifluoromethyl-2'-deoxyuridine, which is formed in vitro from trifluoromethyl uracil, irreversibly inhibits the thymidine synthetase, a key enzyme of the DNA synthesis.

The pyrimidine biosynthesis is irreversibly inhibited by 20% by pyrazofurine, a naturally occurring antibiotic which is micellarly included, and at the same time the cell toxicity is reduced.

It has further been found that the diffusion barriers for antibiotics, e.g. tetracyclines, aminoglycocides, this applying to $\beta$-lactam antibiotics (penicillin), after a certain time in the case of E. coli bacteria are reduced for the micellarly included effective substances. This diffusion barrier is concentration-dependent for the aforementioned active substances but not for the N-tensides prepared according to the invention. These are folding processes at the outer membrane, primarily a change in the structure of the porines within the outer membrane of E. coli, so that for example the inorganic active substances $Hg(CN)_2$, $ZnSO_4$, ZnEDTA can diffuse into the periplasma of the external cell membranes of gramnegative bacteria.

The porines are membranous water-filled pores through which the hydrophilic pharmaceutical active substances can diffuse into the interior of the cell. Hydrophobic pharmaceutical active substances cannot pass through these porines. The $N^+$-tensides, in particular of the general formula $HET=N-(CH_2)_x-CH_3 y^{\ominus}$ and also benzethonium derivatives, can pass through these water-filled pores. Thus, micellarly included pharmaceutical hydrophobic (lipophilic) active substances, in particular of an inorganic nature, due to the hydrophilic outer form of the N+-tensides can reach the cell interior by passive diffusion. There they then react also with the cell-wall-synthesizing enzymes, in particular in the case of $Hg(CN)_2$ at concentrations of 10 µg/ml and ZnEDTA at c=5 µg/ml. The rate of the diffusion of micellarly included active substances increases with increasing hydrophobic character; normally, this is exactly *converse*, e.g. the diffusion rate for gramnegative bacteria decreases with increasing hydrophobic character. Furthermore, a positive charge promotes the diffusion and the formation of mixed micelles of these N-tensides to be prepared according to the invention. The validity of these findings could be proved as a function of the concentration by investigations of the diffusion and dissolving rates of various radioactively ($C^{14}$) marked N-tensides at the membrane (periplasma).

It was also found in vitro that the thymidilate synthetase (TS) (EC2.1.1.45) is inhibited both by $Hg(CN)_2$ in aqueous solution and in micellar solution of an N-tenside of the formulas I and II, in which the $Hg(CN)_2$ is hydrophobically dissolved. TS catalyzes the conversion of dUMP and $CH_2$—$H_4$ folate to dTMP and $H_2$ folate. Since this enzyme is essential to the synthesis of dTMP, i.e. to DNA synthesis itself, it thus represents a target for pharmaceutical active substances against neoplastic cells. It has now been found that for example a solution made according to the invention of hexadecylpyridinium chloride which keeps $Hg(CN)_2$ hydrophobically bound, has the cytostatic activities listed in Table 1 against leukaemia cells (L1210 cells). It was thus possible to find inter alia that TS, dUMP and $Hg(CN)_2$ as inorganic pharmaceutical active substances form a ternary complex according to (A, B)

quaternary ammonium bases according to formulas I and II at pH $\leq 7.0$ which keep $Hg(CN)_2$ hydrophobically bound are therefore therapeutical for slowly growing tumors where other inhibitors are ineffective as regards TS *and* the observed cytotoxicity for the normal cells of other antimetabolites can therefore be slowed down in the case of rapidly growing proliferating cells.

Ribavirin, which is a synthetic 1,2,4-triazolenucleoside, has a broad antiviral spectrum for DNA and RNA viruses. Ribavirin micellarly included by cationic tensides of the form $(HET=N^+—(CH_2)_x—CH_3)Y^\ominus$ passes very rapidly through the membrane barrier, more rapidly than the pharmaceutical active substance itself. The conversion of ribavirin to mosphosphates, diphosphates and triphosphates is also increased by the specific cellular enzymes so that the inhibition of the virus-induced enzymes necessary for the viral nucleic acid biosynthesis is accelerated. Whereas ribavirin on its own only has a moderate effect on the cellular DNA synthesis and is cytotoxic in the range of 200–1000 µg/ml for normal cell lines, the citotoxicity drops in the presence of cationic micelles, when it is micellarly included, to 50 µg/ml (in vitro tests), measured with respect to cells infected with Herpes simples (DNA virus).

Amantadine (1-adamantanamine-HCl) has a particular pharmadynamic action against influenza viruses (class A). The replication of most influenza A strains is inhibited in vitro between 0.2–0.6 µg/ml. Micellarly included amantadine in cationic micelles, in particular of the form $(Het=N—(CH_2)_x—CH_3)Y^\ominus$, effect a reduction of the concentration of pharmaceutical active substance to 0.05 µg/ml amantadine, measured by Hayden et al. (Plaque inhibition assay for drug susceptibility resting of influenza viruses. Antimicrob. Ag.

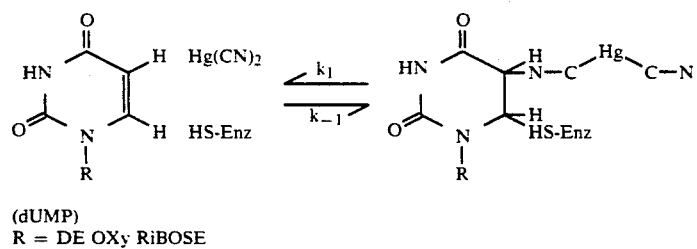

(dUMP)
R = DE OXy RiBOSE

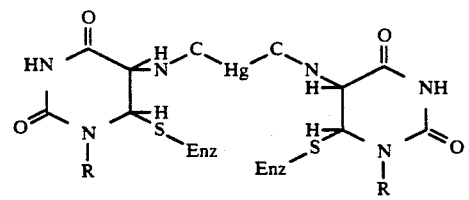

which can be isolated by column chromatography on Sephadex G-25 and BiO-Gel P10. The formation of the complex according to equation A has a formation constant of $k_1=0.51$ $h^{-1}$ in the case of hexadecylpyridinium chloride and $k_1=0.70$ $h^{-1}$ in the case of benzethonium chloride and micellarly included $Hg(CN)_2$. The dissociation constants are $k_{-1}=0.015$ $h^{-1}$ (CPCl) and $k_{-1}=0.02$ $h^{-1}$ i.e. both are very slow, that is the formation and the dissociation of the complex. In contrast the formation of the dimer according to B is substantially faster: $k_1=0.02$ $h^{-1}$ and $k_{-1}=0.015$ $h^{-1}$ for CPCl and $k_1=0.01$ $h^{-1}$, 0.03 $h^{-1}$ for benzethonium chloride. This means that micellar solutions of Chemother. 1980, 17: 8657–70; Grunert et al.; Sensitivity of influenza A/New Jersey 18/76/(Hsw1-N1) virus to amantadine HCl, J. Inf. Dis. 1977, 136, 297–300). Whereas amantadine has practically no activity against influenza virus type B inhibition is exhibited by micellarly included amantadine in the cationic tensides of the formula

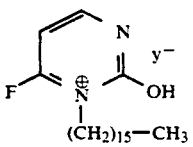

y− = fumaric acid radical (2-hydroxy-5-fluoro-hexadecylpyrimidinium fumarate)

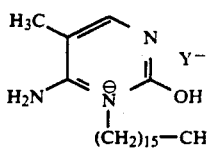

y− = fumaric acid radical

With a concentration of 0.01% by weight of amantadine for influenza virus type B corresponding to a concentration of 0.5 μg/ml pharmaceutical active substance in vitro.

A surprising effect of micellarly included amantadine in the two cationic tensides of the above formula has been found: whereas the influenza virus type A is not resistant to amantadine in vitro it is resistant with amantadine on its own.

Rimantadine-HCl (α-methyl-1-adamantanemethylamine hydrochloride) has the same pharmacodynamic actions in vitro as amantadine but has a greater effect for the same dose. Here too it has suprisingly been found that rimantadine micellarly included in a cationic tenside, in particular of the two above formulae, has the same in vitro effect as the pure pharmaceutical active substance although with a substantially smaller dose of 0.05 μg/ml.

Of the inorganic pharmaceutical active substances, $Hg_2(CN)_4$ and micellarly bound $Hg(CN)_2$ in cationic micelles exhibit a surprising antiviral interferon-induced spectrum. In cell cultures of lymphocytes and fibroblasts it was possible to detect an induction of interferon $\alpha_1$ and interferon β after incubation with micellarly included $Hg(CN)_2$ in a cationic tenside of the formula 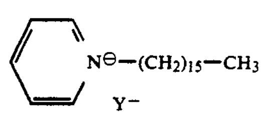 y−chloride Hexadecylpyridinium chloride 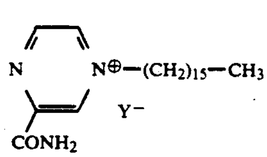 y− = salicylate 2-carboxamide-hexadecyl-pyrazinium-salicylate at a concentration of $Hg(CN)_2$ of 5 μg/ml to 15 μg/ml in a 0.1% (g/g) cationic tenside. In the case of interferon $\alpha_1$ concentrations of 20–50 units/ml were found and in the case of interferon β 10–20 units/ml. The micellar incorporation of mercury cyanide increases the liberation of the interferon $\alpha_1$ in particular however of the interferon β in the case fibroblast cultures by 10 to 100-fold compared with simple aqueous buffered solutions of mercury II cyanides.

Secondary Effects

The observed secondary effects of interferon $\alpha_1$, for example headache, lymphocytopenia, slight to medium sickness symptoms, are not present, or were not observed, with the pharmaceutical preparations described here, in particular against influenza and rhino viruses. This is due primarily to the fact that substantially less units/ml of interferon A, induced by the inorganic pharmaceutic active substance, are used therapeutically than in a therapy with interferon α on its own. Thus, no toxic effects are observed, for example gastrointestinal disturbances, loss of weight, alopecia, peripheral spasms, paraesthesia and bone mark depressions, although these are reversible.

The hematological toxicity, which in the case of interferon $\alpha_1$ depends on the dose (threshold dose $3\times10^6$ units/ml), does not manifest itself with these pharmaceutical preparations for mercury cyanide, rimantadine, amantadine and ribavirin.

b) The pharmaceutical preparation consisting for example of hexadecylpyridinium chloride or a pyrimidinium derivative and a hexadecyl radical in the presence of micelarly included mercury cyanide results in interferon production in the cell culture. This is an interferon induction by liberated mercury cyanide which occurs locally in high concentrations and with a relatively high molecular weight of 4500 by formation of polymeric structures (Paradies, Oligomeric Structure of Mercury Cyanide in Solution, lecture before the German-Austrian Chemical Society, Innsbruck, May 1986). This pharmaceutical preparation thus belongs to the substances of defined interferon inductors of high molecular weight such as synthetic double-stranded RNA: PolyI:PolyC and of low molecular weight such as 10-carboxymethyl-9-acridanone. In spite of this heterogeneity of the interferon action it is antivirally effective. This effect was used for the biological detection of this pharmaceutical preparation. It can be stated that the interferon treatment of cells in the cell culture is modified so that a subsequent virus replication in said cells is inhibited. Interferons thereby differ in their action mechanism fundamentally from virustatics which inhibit the metabolism of the viruses themselves. Since interferons act on the cells it is not surprising that they can also exert other effects on the cells. This applies not only to cell cultures but manifests itself in the entire organism. It is known from a great variety of investigations that interferon inhibits the replication of a great number of viruses. The extent of the inhibition depends on the particular virus system. Thus, the replication of almost all viruses appears to be subject to inhibition by interferon treatment of the cell. There are apparently various mechanisms by means of which interferons can become effective. Thus, for example, the replication of retroviruses is influenced by the formation of budding, i.e. the throwing out of newly formed viriones. A similar mechanism also appears to apply to the pharmaceutical preparation with micellarly included $Hg(CN)_2$. Thus, within the scope of the invention in the case of Herpes simplex virus (HSV 1-3) with the pharmaceutical preparation consisting of cetylpyridinium chloride and mercury cyanide (see example) the effect of induced interferon was detected on the synthesis of early viral-coded proteins of the HSV, the so-called β-proteins. In the case of the SV40 virus interferon also appears to act on a very early step of the replication lying even before the primary transcription.

The pharmaceutical preparation according to the invention, in particular micellarly included mercury cyanide in 7-hexadecylimidazolium-2,6-diamino-[4,5-d]-pyrimidine chloride, exhibited the interferon-induced inhibition in the case of various lytic RNA viruses. The inhibition takes place on the level of the regulation of the viral proteins. It is caused by induction of specific cellular enzymes. A more exact investigation showed that the enzymes inhibit the 2',5'-oligodenylate synthetase, the 2,5-A-dependent endoribonuclease and the dsRNA-dependent protein kinase. By correlation studies and characterization of cell mutants it was possible to prove for the two former substances participation in the antiviral activity against lytic RNA viruses by micellarly bound $Hg(CN)_2$.

In these experimentally proved effects it was also possible to detect an antiproliferative effect of this pharmaceutical preparation on the interferons in many ways on the membranes and on the cytoskeleton of cells. Thus, they also influence the expressions of a number of important genes, for example that of the main histocompatibility locus, the so-called transplantation antigens. Thus, immunological regulatory effects are also apparent (interleukin-1 synthesis). This gives the following therapeutic and pharmacodynamic aspects: The induction of the interferons by this pharmaceutical preparation leads to increased expression of the cell surface proteins which play the most important part in the immunological response. These are the so-called transplantation antigens. It should further be noted that at least two important cellular components of the endogenous immune system are activated, that is, the macrophages and the natural killer cells. Also, in particular as regards interferon γ, the functions of the B-lymphocyte appear to be decisively influenced by this pharmaceutical preparation.

Thus, for the pharmaceutical preparation according to the invention, in particular in the case of hexadecylpyridinium chloride and micellarly included mercury cyanide or 7-hexadecylimidazolium-2,6-diamino-[4,5-d]-pyrimidine chloride, or also the bromide, an induction of interferon results, although not a specific one. There can be no doubt that interferons have an immunological regulatory effect and not only an antiviral effect both in vitro and in vivo. Although the direct antiviral effect can also be of significance in vivo, in the organism as regards the interferon effect as explained above other indirect mechanisms play a part, for example the activation of macrophages in particular in the case of the influenza virus A and B. The fact that interferon γ can activate macrophages also appears to be important with regard to bacterial and parasitical infections because macrophages play a significant part in the defence against such infections.

Posolgy and Therapeutic Indications

The therapeutic indications and the dose depend on the micellarly included concentrations of the pharmaceutical active substance:
thus, indications exist for incipient and existing colds caused mainly be influenza and rhino viruses;
catarrhal inflammations of viruidic origin;
skin infections and infectious dermatoses;
persistent antiseptic treatment of wounds;
dermatomycoses;
mycoses;
prophylaxis and therapy of bacterially induced skin lesions such as pyodermia, otitis media;
microbial and secondarily infected exzema;
oversensitivity to macrolide antibiotics;
acne, in particular inflammatory forms with papules and pustules;
bacterial infections and secondary infections of the skin in so far as they are due to grampositive and-/or gramnegative meclocycline-sensitive germs;
acne vulgaris;
prevention of navel infections;
surgical and traumatic wounds;
local protection from infections and wounds infected with antibiotic-sensitive germs;
furuncles, carbuncles, abscesses;
dermatomycoses caused by dermatophytes, saccharomycetes, hyphomycetes and other fungi, pityriasis versicolor,
erythrasma through corne bacteria;
candidiaces of the skin and mucus membranes;
Herpes simplex I-III, Herpes Keratitis;
solar and senile keratoses, premalignant changes and superficial basalioma, also in radiation-damaged skin;
squamous cell carcinoma of the skin and mucosa in the head and neck region; dermatological malignant growths.

The specific dose depends on the diagnosis and pharmaceutical active substance. Since the maintenance and initial dose of the pharmaceutical active substances described here are known, depending on the type of application and galenic preparation, e.g. creams, suppositoris, drops, tablets, capsules and liposome-like encapsulations, only 50% of the normal therapeutical total dose is required, depending on the concentration of the micellarly included pharmaceutical active substance.

Outline of the Dose Reduction Due to the Potentiating (Synergistic) Effect

Micelles in aqueous solution, also those with included lipophilic active agents, are in dynamic equilibrium with their monomeric tensides, i.e. the micelles change form, size and hydration. Under some circumstances monomeric cationic tensides leave a particular micelle to join again another micelle in aqueous solution so that even when the concentration of the tenside is far above the cmc there is always a certain concentration of fluctuation monomers. By addition of the potentiating mixture these dynamics are destroyed in that 1) at constant temperature and chemical potential the form, size and monodisperse homogeneity of the isotropic solution is retained and consequently there is no loss of micellarly included lipophilic (hydrophobic) pharmaceutical active substance.

2) The concentration of monomers which has a destablizing effect on the geometrical form of the micelle is restricted in favour of incorporation into the "complete" micelle in isotropic solution. As a result the system, including the micellarly included hydrophobic pharmaceutical active substances, "leaks". This is prevented mainly in that the potentiating mixture, in particular glycerol and dimethylsulfoxide freezes the water structure at the external surface of the micelle (tridymit structure) in such a manner that it assumes ice-like structures and the water molecules become very immobile.

3) Due to the potentiating effect of the glycerol, as has been demonstrated for example in vitro, the pharmaceutical preparation is less cytotoxic, i.e. it damages primarily the affected (infected) cell and not so much the healthy cell in the cell unit.

The invention has in particular the following advantages:

The N-tensides prepared according to this invention, together with the inclusion according to the process of the invention of the active agents, results in a considerable reduction, in some cases up to 80%, of the toxicity of the inorganic active agents or substances, e.g. with $Hg(CN)_2$, (also $HgCl_2$, $HG(NH_2)Cl$ [precipitate], ZnEDTA) and Zn salts in general, as well as with nephrotoxic, ototoxic antibiotics, in particular polymixins, erythromycin, gentamycin, tetracyclin, of about 30% because 1) the micelles, and their included active substances, are not resorbed, due to their size,
2) the micellarly included active substances develop their effects *only* at the location, usually topically, so that small concentrations of active substances are adequate since additionally there is the synergistic effect of the N-tenside.

It has thus been found inter alia that the inhibitory effect on salivary secretion of atropine by hexadecylpyridinium chloride and by benzothiazolium sulfate is intensified tenfold by micellar catalysis with N-tensides made according to the process of the invention, pH $\leq 7.0$. The increased effect on the periphery is inter alia due to the micellar separation of the racemate into $L(-)$ hyocyamine (see FIG. 1).

Also, hexadecylbenzthiazolium sulfate for example stabilizes the atropine by incorporating the hydrophobic molecule regions of the atropine into the micellar core.

This content of the claim extends also to the antiphlogistic properties of the quaternary organic ammonium bases described here. The counter ion $Y^-$ has a process-inherent influence on the size, form and micellar stability but may also itself be a pharmaceutical active agent so that a drug action can be pharmacodynamically intensified. The tensides described here have the great advantage that in addition to the intrinsic pharmacodynamical properties they are environment-dependent and moreover stable in the acidic pH range. The micelles which can be obtained by the process as pharmaceutical preparation with included lipophilic (hydrophobic) pharmaceutical active substances act as carriers for antimicrobial, antiviral, keratolytic, antifungal and antineoplastic active substances but may also themselves inter alia have an antimicrobial, antifungal and antiviral and antiphlogistic (topical) effect.

In particular, the present invention describes a pharmaceutical preparation for providing micellar dissolved hydrophobic inorganic substances such as mercury II cyanide, zinc, tungsten and antimony compounds as well as salts of phosphonic acid. It has been found that these organic compounds have both antiviral and antineoplastic effects.

The formation of the vesicular structures of the quaternary ammonium bases of 4 and 3,5-substituted hexadecylpyridinium-$Y^-$ also takes place spontaneously at constant temperature, pressure, ionic strength, also in the presence of stoichiometrically pharmaceutical active substances which can be bound both vesicularly (void) and micellarly (in the manner of double membranes).

In particular the invention relates to an improved preparation method for making multilamella lipid bubbles on the basis of cationic tensides which can be used in particular to encapsulate lipophilic (hydrophobic) pharmaceutical active agents.

Most hitherto known processes suffer either from inadequate encapsulation effect or from a limitation of the types of materials which can be included or from both these defects. Thus, as is known most of these processes are restricted to the inclusion of hydrophilic materials and pharmaceutical active substances and cannot efficiently perform the inclusion of lipophilic pharmaceutical active substances. In contrast thereto, all the presently available methods with the exception of that of Banghan et al. (Biochem. Biophys. Acta 443: 629-634, 1976) are suitable only for the encapsulation of biologically active substances in oligo-multilamella or unilamella liposomes.

A particular advantage of this pharmaceutical preparation on the basis of vesicular structures of $N^+$-tensides is the hydrophobic encapsulation of pharmaceutical active agents. A particularly advantageous consequence of the large-size vesicles made by ultrasonic treatment and counter ions is to be seen in that the danger of emergence of the pharmaceutical active substance from the bubble skin of the preparation is reduced or eliminated. Consequently, this form of the quaternary $N^+$-tensides on the basis of six-member heterocycles can be employed in particular for encapsulation of hydrophobic pharmaceutical active substances which may be used to achieve local, i.e. topically restricted, effects instead of systemic effects.

Whereas most of the known processes are restricted to the encapsulation of hydrophilic active agents with this invention encapsulation of hydrophobic pharmaceutic active agents may be carried out. Tests have shown that even inorganic lipophilic pharmaceutical active agents such as mercury II cyanide can be included with high efficacy and their pharmocodynamic effect can be further enhanced by the potentiating mixture.

This disadvantage is eliminated by the novel N-tensides of the general formula II and novel benzethonium compounds and also the vesicles on the basis of $N^+$-tensides either by micellar inclusion of the pharmaceutical active substances or by covalent linking of the active substances to the $N^+$-tenside whilst retaining the outer morphological form of the overall micelle.

The bactericidal effect of chlorhexidine on gramposi-tive and gramnegative bacteria is known but gramnegative bacilli are resistant. It has been found that micellar solutions of quaternary ammonium bases according to the general formula I and in particular II which bond 2-4% by weight chlorhexidine hydrophobically in the micellar core cancel the resistance to gramnegative bacilli and increase their therapeutical efficacy compared with chlorhexidine alone. The secondary effects observed of chlorhexidine such as contact dermatitis, skin effects of topical nature, photosensibility of the skin, do not take place with the micellar solutions of the N-tensides of the formula I and II made by the present process.

It is the object of the present invention to eliminate the heterogeneity mentioned at the beginning of the form of size of the micelles even in the presence of potentiating mixtures. It is thus ensured that a monodisperse form of cationic organic ammonium bases is achieved even in the presence of pharmaceutical active substances and potentiating mixtures in the preparation thereof.

These organic ammonium bases according to the invention obviate the aforementioned disadvantages of the hitherto known conventional invert soaps. Thus, there is also great interest in the therapeutic use of quaternary ammonium bases which function both as pharmaceutical active agent *and* carrier of active agents of a great variety of types, for example antimicrobial, antiviral, antifungal or antineoplastic nature, can absorb substances micellarly. They should therefore not have the aforementioned disadvantages dependent mainly on the environment.

The active substances covalently bound pharmaceutically, such as pyrimidine and purine derivatives at the $N_1$ or $N_7$, on the basis of quaternary ammonium bases, have the advantage 1. that these masked antimetabolites from the pyrimidine or purine series do not enter any intramolecular interactions of an anionic or cationic nature. They are neutrally charged (e.g. no nucleotide dianion by the phosphate) and can thus diffuse unrestrictedly into the pro or eukaryotic cell so that high intracellular antimetabolite (e.g. 5'-nucleotide) concentrations are achieved;

2. that the pharmaceutical active substances by N-C-hydrolysis by means of the enzyme systems present of the germinal or eukaryotic cells are liberated at the target or also topically;

2. by the increase in the hydrophobicity of the alkyl or aryl chain or the radical at the $N^+$-tenside the membrane permeability is increased so that the pharmaceutical active substances can pass quantitatively and passively into the cytosol. In contrast to dianions or cations which have difficulty in passing through the membrane under physiological pH conditions and ionic strengths this can be done by the $N^+$-tensides according to the invention without restriction;

4. the high hydrophobicity also gives a high distribution coefficient in the system $CHCl_3$—$H_2O$ at pH 8.0;

5. by the concentrated absorption of hydrophobic or hydrophilic pharmaceutical active substances, in addition to the covalently anchored substances, the active substance concentration is increased after penetration through the germinal membrane, fungal cell wall (inhibition of chitin synthetase) or viral phospholipid double membrane by a concentration gradient (extracellular-intracellular). This results in a low flooding time.

In contrast to liposomes as carrier of pharmaceutical active substances as described for example in U.S. Pat. No. 3,993,754 or European patent 0,102,324, the micelles of quaternary ammonium bases described according to the invention have the advantages 1. that they can absorb water-insoluble active substances micellarly in the so-called liquid core and as a result these water-insoluble active substances can be liberated in controlled manner both topically and enterally by opening of the micelle, said active substances being for example rimantadine, amantadine, tromantadine, which are effetive against influenza viruses and Herpes simplex viruses both of the skin and of the eye.

2. Water-soluble active substances can be dissolved both in the Stern layer and also micellarly if they themselves have hydrophobic ranges, for example polyene compounds, tetracylines, aminoglycosides and aromatic antimetabolites, e.g. trifluorothymidine, viderabine, cytarabine, 5-iodo and 5-fluorodeoxyuridine, 5-ethyl-2'-deoxyuridine, erythromycin and nalidixic acid.

3. The cationic N-tensides according to the invention have two specific bonding sites with high bonding constants ($K_B = 10$–$15$ $\mu M$) and high bonding capacity (capacity 100 $\mu g$/micelle): the first is due to the hydrophobic interaction between the liquid core of the micelle and the hydrophobic range of the active substance ($\Delta G = 15$–$20$ kcal/Mol) and also the $\pi$-$\pi$-interactions of the active substances described here between the N-heterocycles of the N-tensides and the pharmaceutical active substances; the second binding site is nonspecific and is localized at the interface between the Stern layer and the hydrophobic core. The binding constant lies in the region of $K_B = 20$ mM and the bonding capacity is 100–200 $\mu g$/micelle. The nonspecific binding sites are almost without exception in the Guy-Chapman layer. In contrast to liposomes where the number of nonspecific binding sites is substantially higher the number of nonspecific binding sites can be eliminated by addition of ethanol/glycerol since the forces which act in the Guy-Chapman layer are eliminated by concentrations of ethanol and glycerol up to 30–35% by weight without influencing the bonding capacity and strength of the hydrophobic forces (only polarity and configuration).

4. The invention described here has the advantage that the micellarly included or enclosed pharmaceutical active substances do not leave the micellar union as for example in the case of liposomes which with the hitherto known methods "leak". The sealing of the present invention of micellarly enclosed active substances can be detected for example in micellarly bound radioactively marked trifluorothymidine, cytarabine and idoxuridine. It has been found inter alia that idoxuridine loses 5% by weight of its original micellarly included concentration (2000 $\mu g$) in the case of hexadecyl-pyridinium or benzethonium chloride micelles only after 200 days. The corresponding values for radioactively marked trifluorothymidine and cytarabine are 210 and 300 days (20° C.).

5. According to the process of the present invention these micelles with the included inorganic and organic active substances at pH = 7.0 can be made in simple manner without excessive apparatus expenditure in aqueous phase containing simple micelles with a diameter of about 50–100 Å and large micelles with a diameter of 600–10000 Å, depending on the counter ion. In addition, by a mixture of glycerol/ethanol in a ratio of 2% by weight: 15% by weight with respect to water both micelles of the different order of magnitude are stabilized both in their form (sphere, hemicylinder, rod, disk) and in their compactness by lowering the cmc, as also by reduction of the free energy of the total micelle in the aqueous phase due to thinning of the electron density at the external surface. Small micelles can be preparatively separated from large micelles by appropriate separation methods, e.g. HPLC, ultrafiltration, gel filtration and/or preparative centrifugation.

6. The stability, durability and storability of these micelles made in this manner from quaternary organic ammonium bases, pH = 7.0, to temperature, sealing and leaking and storage is increased by the incorporation of the pharmaceutical active substances into the hydrophobic core of the micelles compared with micelles without active substances for the same $Y^-$. In contrast to the liposomes in this case no melting occurs at higher temperature (>40° C.); with the preparation according to the invention the hydrodynamic conditions change only from >60° C. Since with increasing temperature the micelles of quaternary ammonium bases made in this manner tend rather to undergo a reduction in the hydrodynamic radius and therefore become more compact, this type of micelle is thermodynamically more stable than synthetic liposomes or liposomes+quaternary ammonium bases. These processes can easily be checked by routine methods by inelastic light scattering in their preparation.

7. The hydrophobicity or penetration of the $H_2O$ molecules into the micelles made in this manner and their influencing by inorganic pharmaceutical active substances, e.g. $Hg(CN)_2$, ZnEDTA, $ZnSO_4$, ZnO, wolframic acid antimonates, $K_{18}(KW_{21}Sb_9O_{86})_{17}$, and also organice substances, can be determined by NMR spectroscopy:

Taking as example 8-ketohexadecylpyridinium chloride (8-KHPCl) the incorporation of pharmaceutical active substances according to the invention can be demonstrated. It has consequently now been found that a chemical displacement of 146.6 ppm occurs for a 0.1 molar micellar solution in water which is however shifted by for example $Hg(CN)_2$ to 147.2 ppm. Micelles in aqueous solution which are 0.05 molar in 8-KHPCl and 0.2 molar in CPCl (cetylpyridinium chloride) however gave a chemical displacement of 147.2 ppm for the $^{13}C$-carbonyl signal of 8-KHPCl. If these two Figures are compared with the displacements of 8-KHPCl in methanol (145.7 ppm) and acetonitrile (144.0 ppm) it becomes clear that the CO group in this micelle assumes a largely aqueous environment. $Hg(CN)_2$ plays here a double role which thus also governs the therapeutic width in vitro: the hydrophobic character of the $Hg(CN)_2$ effects a high solubility in the hydrophobic core of for example hexadecylpyridinium chloride as monomer and gives a chemical displacement of $\delta_{c8}$ 27.5 ppm $^{13}C$ of $CH_2$ chain to 32.5 ppm whilst in 8-KHPCl micelles mercury II cyanide is dissolved in the vicinity of the keto group ($C_8$) as $Hg_2(CN)_4$ in $H_2O$ (see above) and by this $H_2O$ solubility the concentration of $H_2(CN)_4$ is limited.

FIG. 5 shows the dependence of the extinction of the micellarly included inorganic active substances and of the N-phosphono-acetyl-L-aspartate in hexadecylpyridinium chloride.

Hereinafter a modification of the invention is described which concerns in particular N-alkylated quaternary nitrogen-containing heterocycles.

State of the Art

Known are the quaternary ammonium bases with tenside-like effect of the general structure (I)

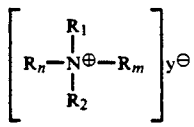

wherein generally
$R_1$ = an alkyl radical with 1-12 C atoms
$R_2$ = an alkyl radical with 1-12 C atoms
$R_n$ = a straight-chain or branched alkyl radical with 10-20 C atoms or an alkenyl radical with 8-10 C atoms or a 5 or 6-member aromatic heterocycle with one or 2 nitrogen atoms and
$R_m$ = a straight-chain or branched alkyl radical with 10-20 C atoms or an alkenyl radical with 8-10 C atoms or a 5 or 6-member aromatic heterocycle with one or 2 nitrogen atoms.

$y^-$ = a monovalent anion

Compounds of this general formula have partly been described in the Tensid-Taschenbuch, published by Dr. H. Stache, Carl-Hauser-Verlag, Munich, Vienna, 1981, pages 8/9.

Some of these compounds are also the subject of a European patent application, application no. 83810338. 0 of Jul. 24, 1983, and these tensides are used to prepare unilamellar liposomes in aqueous phase for the dispersion.

It must also be taken into account here that these known $N^+$-tensides of the general formula I form both micellar and vesicular structures in aqueous and nonpolar solvents ((cf. for example J. Fendler, Acc. Chem. Rees 1976, 9, 153; H. H. Paradies, J. Phys. Chem. 1986, 90, 5956; H. H. Paradies, 1982, Angew. Chem 10, 737; Angew. chem. Int. Ed. Engl. 1982, 21, 765, Supplement 1982, 1670-1681) and here also micellarly catalyze defined chemical and biophysical reactions depending on the objective.

In contrast, cationic tensides having a quaternary nitrogen within a $\pi$-excess or $\pi$-defective aromatic, substituted or not substituted in the core, are less well known. Descriptions exist for example for hexadecylpyridinium halide (cetylpyridinium halide), cf. inter alia Merck Index 9, quinoline, cf. K. Lindner, in Tenside-Textilhilfs-stoffe-Waschrohstoffe 1964, volume 1, 987) and benzthiazolium salts (European patent application 85400876.0 of May 6, 1987, no. 660,802 Belgium, of Mar. 8, 1965) with various alkyl chain lengths and counterions for use in photography and electron transmission by suitable formation of charge-transfer complexes. These are however 2-methyl or 2-substituted benzthiazolium compounds with variable hydrophobic alkyl chain length of 12-30 carbon atoms at the hetrocycle of the condensed-on benzene ring.

Furthermore, in the prior art the 2-substituted imidazolium salts and 2-thiazolium compounds are described (cf. Tensid-Taschenbuch, H. Stache, 2nd edition, 1981, pages 8/9), without however the cmc and other micellar properties being specified. Corresponding matter is also described for the imidazolium compounds, cf. for example Tensid-Textilhilfsmittel-Waschrohstoffe K. Lindner, 1964, 993; wissenschaftliche Verlagsgesellschaft, Stuttgart.

For vesicular compounds having a pyridine ring as aromatic substances only 4 and 3.5-alkyl or alkoxyl compounds have been described containing a methyl group at the quaternary nitrogen (cf. for example Sudholter et al. 1982, J. Amer. Chem. Soc. 104, 1069, Sudholter et al. 1979, J. Amer. Chem. Soc. 102, 2467).

An objective of the present invention is to provide new N-akylated quaternary nitrogen-containing heterocycles. This problem is solved according to the invention in that the N-alkylated quaternary nitrogen-containing heterocycles have the general formula

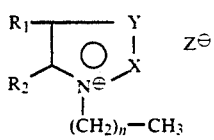

X = CH; C—CH₃; N
Y = N; S; CH
R₁ = H; CH₃; OH
R₂ = H; CH₃; OH wherein
n = 8–20, in particular 15 and
Z⁻ = chloride, bromide, iodide, maleate, formate, acetate, propionate, hydrogen sulfate, malate, fumarate, salicylate, alginate, gluconate, glucoronate, galactoronate, ethyl sulfate or hydrogen phosphate H₂PO₄⁻.

Hereinafter some advantageous embodiments of the invention will be described:

1. 4-substituted 2-n-alkylpyrazolium compounds of the formula

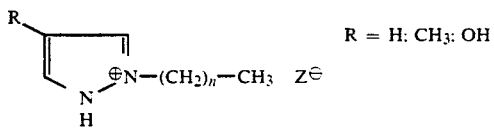

R = H; CH₃; OH wherein Z⁻ denotes the above 17 anions and n = 8–20.

2. 4-substituted 2-hexadecylpyrazolium compounds of the formula

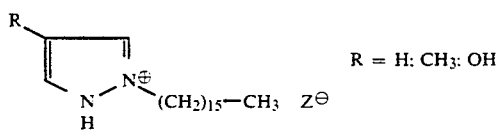

R = H; CH₃; OH wherein Z⁻ denotes the above 17 anions.

3. 1-n-alkyl-4-substituted imidazolium compounds of the formula

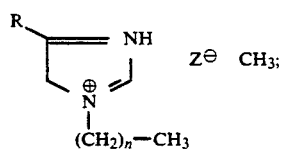

wherein Z⁻ denotes the above 17 anions and n = 8–20

4. 1-hexydecyl-4-substituted imidazolium compounds of the formula

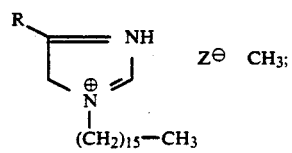

wherein Z⁻ denotes the above 17 anions.

5. 3-n-alkyl-2,5 substituted thiazolium compounds of the formula

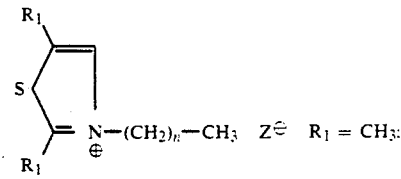

R₁ = CH₃;

wherein Z⁻ denotes the above 17 anions and n = 8–20

Preparation of the N-alkylated Quaternary Nitrogen Containing Heterocycles According to the Invention a) General Remarks on the Preparation These cationic tensides are characterized in that they have a very small micellization constant (cmc) of about $1.0 \cdot 10^{-6}$–$1.5 \times 10^{-7}$ mol/liter, have a very strong antimicrobial and antifungal effect, do not exhibit polydispersity in the presence of inorganic anions or potentiating mixtures and in some cases themselves are microbial metabolism products (antimetabolites) which are not toxic for the host cell.

The formation of the salt-like structure of this class of cationic tensides of the form (HET≡N⁺—(CH₂)ₓ—CH₃) Y⁻ is due inter alia to the electron density distribution of the heteroaromatic nuclei and to their basicity, including the influence of the substituents. A necessary condition for the formation of quaternary salts of this five and six-member heteroaromatic class is that the electron density at the nitrogen which is quaternized in accordance with MO-SCF calculations must have a magnitude of −0.08 (e.g. pyrazine-N₄) to −0.159 (e.g. imidazole-N₁, purine-N₇). This stability of the heterocyclic cationic tensides described here depends also on its symmetry and chain length of the alkyl chain at the quaternary nitrogen.

In the case of imidazole, benzimidazole, for example stabilization is effected by the formation of the salt and the quaternary nitrogen N₁ and the free electron pair at the N₃ and the resulting high symmetry. The same applies to the H₉-tautomers of purine and its symmetrically arranged substituents which influence the negative charges at the N₁(−0.124 N₃ (−0.108) and N₉ (0.149) in such a manner that the quaternization at the N₉ is preferred in that the aforementioned order N₁→N₃→N₉ is reversed. By the choice of suitable solvents the yields can be increased. Whereas for pyridine, pyrimidine and imidazole radicals symmetrical effects at the core play an important part, in the case for example of pyrazine the electronic effect in the 2-position is of significance but there are also very pronounced inductive effects (e.g. 2-amino group), less than mesomers. This also applies to pyrazole.

The length of the alkyl chain at the quaternary nitrogen atom governs not only the melting point and hydrophobicity of the cationic micelles subsequently formed in aqueous solution but in addition the yields decrease with increasing chain length whilst the reaction times increase for example in nitrobenzene or 2-ethoxyethanol.

Stable and easily crystallizable compounds are obtained for C₁₂–C₁₈, the counter ion Y⁻ being always bromide and chloride. The other compounds can easily be recrystallized from acetone or chloroform. The corresponding iodine compounds are temperature-sensitive and light-sensitive.

b) Specific Preparation

Preparation of this Specific Compound Class a) The compounds of the substituted imidazole as 5-member heterocycle can be prepared from the corresponding substituted alkyl bromides or iodides in methanol at 35° C. and substituted imidazoles with high yield of 70%. The corresponding molar amounts of the substituted alkyl bromides, which are all available commercially but must be subsequently purified by high-pressure liquid chromatography (HPLC), are first dissolved in methanol with 10-times volume excess compared with the substituted imidazoles and under nitrogen the stoichiometric amount of the respective substituted imidazole which is also dissolved in the methanol is added dropwise whilst stirring. Reflux heating at 70° is carried out for 6 hours so that the reaction yield is almost quantitative. Thus, for example, the yield of hexadecyl-4-methyl chloride or bromide in methanol as solvent is 95%, with ethanol 80% and in ether/ethanol only 40%. N(1)-dodecylimidazolium bromide forms quantitatively in accordance with the aforementioned provision from dodecyl bromide and 4-methylimidazole in boiling chloroform after 4 hours (melting point 108° C.).

Purification of the corresponding 4-methylimidazolium compounds. After repeated recristallization from mixtures of methanol/ether, starting at 40/60 (v/v); 50/50 (v/v) and finally 90/10 (v/v) the desired products are obtained with constant melting point, unitary molecular weight and specific surface-active properties (measured by the concentration dependence of the surface tension). In addition these compounds exhibit the typical $^1$H-NMR signals mentioned above. The numerous $CH_2$-groups and the $CH_3$-group generate a clearly visible absorption line in the IR spectrum at 2930 $cm^1$ and 2850 $cm^{-1}$ (methylene group), a medium weak band at 2960 $cm^{-1}$ and a far weaker band at 2870 $cm^{-1}$ which can be assigned to the methyl group.

A rapid and quantitative separation of the N(1) alkyl-4-substituted imidazolium or N(1), N(3)-dialkyl-4-substituted imidazolium salts, in particular the bromides, from non-converted n-alkyl bromides is achieved by preparative high-pressure liquid chromatography on an RP-18 column with the aid of an elution mixture consisting of 60% (v/v) methanol (ethanol) and acetonitrile 40% (v/v) isocratically at 9.53 atm column pressure (UV detection at 248 nm).

A further successful separation of mono and disubstituted alkyl-4-substituted imidazolium salts from unconverted n-alkyl halides can be effected by pressure hollow fiber concentration. The separation of the N(1)-monoalkylated 4-substituted imidazolium salts from the corresponding di N(1) and N(3)-4-methylimidazolium compounds can be effected by column chromatography on a DEAE-sephadex A 50 (1.5×10 cm) in 70% v/v methanol and 20% (v/v) acetonitrile) with which 10% water is admixed.

A further method for the preparation of the N(1) alkylated 4-methylimidazolium salts consists in the reaction under pressure in stainless steel autoclaves in 3-ethoxyethanol at 120° C. from the corresponding n-alkyl bromides with the 4-methylimidazole. The reaction duration is as a rule 8 hours and the yield mounts to 60–70% independently of the alkyl chain length of the n-alkyl halides.

A separation of mono and dialkylated imidazolium compounds, which must form in an amount of about 10%, is carried out as described above.

Tables 1 and 2 show the characteristic compositions and properties of these $N^+$-tensides including their hydrodynamic radius in dependence upon $Z^-$.

b. N(2)-n-alkylpyrazolium compounds and their preparation.

The corresponding salts of N(2)-alkylated compounds of pyrazole can be very successfully made by reaction of triethyloxonium tetrafluoroborate ($Et_3O^+BF_4$) and n-alkyl bromides in nitrobenzene (70° C.) or acetone (50° C.) with good yields.

c. The corresponding N(2)-n-alkylpyrazolium salts can be obtained in good yields by reaction of n-alkyl-MgX (X=Br, Cl, J) with 4-methyl or 4,5-dimethylpyrazole in n-heptane or alternatively diisopropylether. No hetarine or addition and elimination addition mechanism takes place. The 4-H-pyrazolium salts with $R_1=CH_3$ and OH form as a rule with high yields of 60–70%.

Since the n-alkyl radical may be located both at the N(1) and at the N(2) or at both nitrogens it is necessary to separate the reaction product by high-pressure liquid chromotography on an RP-18 column, for example by an elution mixture consisting of acetone/acetonitrile. This is also necessary when the corresponding n-alkyl bromide is brought to react in a bomb tube or autoclaves with a 4,5-substituted pyrazole derivative at 100° C. in the presence of piperidine. The ratio of di-N-alkylated to mono-N(2)-alkylated pyrazolium salts is 1.5:1 irrespective of the alkyl chain length (n=8–20) under the aforementioned preparation conditions.

Table 1 represents characteristic properties of this compound class whilst table 2 shows the hydrodynamic radii in dependence upon $Z^-$.

As usual and explained above, the $(CH_2)_x$ chain with $x=10-20$ or the $(CH_2)_n$ chain with $n=10-20$ governs the size and the cmc in aqueous solutions. The resulting size, shape and molecular weight distribution of the micelle in aqueous solution at pH <7.0 depends on the nature of the counter ion $Y^-$ or $Z^-$.

The corresponding thiazolium compounds may be made easily and in good yields (about 60%) by reaction of the corresponding alkyl chlorides with thiazole in a bomb tube or autoclaves in the presence of piperidine at 60° C. with 8 hours reaction time.

The thiazole, in particular when no electron-donating groups ($NH_2$, OH) are present in the 2-position, behaves similarly to pyridine, in particular 3,5 and 4-substituted pyridines with regard to the alkylation reactions with n-alkyl halides. Thus, the analogous processes as with pyridine can be used for alkylation with n-alkyl halides for thiazole and 4,5-substituted thiazole derivatives.

Table 1 shows the elementary composition, melting point and cmc of some thiazolium salts made in this manner whilst table 2 shows the dependence of the hydrodynamic radii $<R_{:n}>$ on $Z^-$.

In contrast to thiazole the $^1$H-NMR signals of N(3)-thiazolium salts do not exhibit any widening of the 2-H and 4-H signals caused by the influence of the first —$CH_2$ group of the n-alkyl chain at the N(3)-nitrogen. Normally, no widening of the 2-H and 4-H signals arises in the $^1$H-NMR spectrum due to the quadrupole relaxation of the nitrogen which is reduced by the quaternization.

Both for the pyrazolium and imidazolium compounds as well as the thiazolium compounds with their long alkyl chains at the quaternary nitrogen sharp signals are observed in the nuclear resonance spectrum with weak line width which provides an indication of the formation of micelles with a diameter smaller than 600 Å. Sharp signals at δ about 0.89 ppm (—CH$_3$), δ about 1.28 ppm (CH$_2$—) and δ 3.23 ppm (—N—(CH$_2$)$_2$) are for example characteristic of these micelles of the N$^+$-tensides described. The methyl signal occurs predominantly as singlet at δ=0.89 ppm and originates exclusively from the micelle.

Table 1 shows some characteristic compounds of the class of the heterocycles according to the invention.

Table 2 shows the hydrodynamic radii of some characteristic heterocycles made according to the invention in dependence on the anions Z$^-$.

manner in the transcription and in the translation. This is of particular significance for infectious processes of bacterial (prophages) or above all viral nature.

Of significance for subsequent use of these N$^+$-tensides is the control of the colloidal-chemical "aggregates" (micelles) by the counter ions Z$^-$ of both inorganic and organic nature. In contrast to many other amphiphiles, which are not water-soluble, these N$^+$-tensides, due to their hydrophobic effect, can form sheet-like double membrane structures in water or aqueous solutions. Usually they have a cylindrical form which depends however very much on the counter ion: in the presence of primary phosphate (H$_2$PO$_4^-$) and in the presence of gluconate or galactoronate highly oriented micellar fibril structures are formed which are

TABLE 1

| | Characteristic substance constants of N-alkyl 5-ring (heterocycles) | | | | | | | |
|---|---|---|---|---|---|---|---|---|
| | | | \multicolumn{4}{c}{Analysis (%) found} | | cmc × 10$^{-6}$ |
| Nr. | N-Tenside | Z$^-$ | Z | C | H | N | Fp(°C.) | Mol/Liter |
| 1. | 4-Methyl-N(1) Hexadecyl-imidazolium | Cl$^-$ | — | 69.69 | 11.89 | 8.12 | 142 | 3.90 |
| 2. | 4-Methyl-N(2)-Hexadecyl-pyrazolium | Cl | — | 69.67 | 11.89 | 8.14 | 172 | 0.70 |
| 3. | 4-Methyl-N(1)-Octyl-imidazolium | Cl$^-$ | 15.4 | 62.45 | 8.72 | 12.15 | 169 | 0.85 |
| 4. | 2,5-dimethyl-N(3) Hexadecyl-thiazolium | Br$^-$.1H$_2$O | — | 57.15 | 20.50 | 3.34 | 170 | 1.51 |
| 5. | 2,5-dimethyl-N(3) Octyl-thiazolium | Br$^-$ | 29.52 | 44.44 | 8.97 S: 11.87 | 5.18 | 180(dec) | 1.15 |
| 6. | 4-Methyl-N(1) Dodecyl-imidazolium | Cl$^-$ | 14.5 | 63.39 | 10.30 S: 14.32 | 11.44 | 210 | 0.95 |
| 7. | 4-Methyl-N(1) Nonyl-imidazolium | Cl$^-$ | 15.7 | 53.42 | 10.31 | 6.23 | 200.5 | 0.75 |

TABLE 2

Dependence of the hydrodynamic radius of the N$^+$-tensides on Z$^-$

| N-Tenside | Z$^-$ | <R$_H$> | (Å) |
|---|---|---|---|
| N(1) Cetyl-4-Methyl-imidazolium | Br$^-$ | 140.0 | +/−10.0 |
| | Cl$^-$ | 70.0 | +/−5.0 |
| | NO$_3^-$ | 120.0 | +/−10.0 |
| N(1) Octyl-4-Methyl-imidazolium | Cl$^-$ | 210.0 | +/−10.0 |
| | HSO$_4^-$ | 650.0 | +/−25.0 |
| | H$_2$PO$_4^-$ | 300.00 | +/−15.0 |
| 2,5-dimethyl-N(3)-hexadecyl-thiazolium | Cl$^-$ | 150.0 | +/−10.00 |
| | Br$^-$ | 200.0 | +/−10.00 |
| | Salicylate | 1000.0 | +/−25.0 |
| 4-Methyl-N(2)-hexadecyl-pyrazolium | Cl$^-$ | 200.0 | +/−10.0 |
| | Br$^-$ | 300.0 | +/−25.0 |
| | H$_2$PO$_4^-$ | 1500.0 | +/−100.0 |
| | NO$_3^-$ | 300.0 | +/−20.0 |
| 4-Methyl-N(1)-dodecyl-imidazolium | Cl$^-$ | 150.0 | +/−10.0 |
| | Br$^-$ | 170.0 | +/−200 |
| | NO$_3^-$ | 200.0 | +/−10.0 |

USES

The compounds newly described here surprisingly have a very small cmc in the range of $10^{-5}$–$10^{-7}$ mol/liter which is largely independent of the pH and ionic strength (=0.1M). In addition, since in some cases they are themselves antimetabolites, they have a biochemical and pharmacodynamic effect. Due to their "monovalent" cationic nature they are able to penetrate the cell membranes of neoplastic tissues and the by unknown mechanisms after formation of the corresponding nucleosides and phosphorylation intervene in inhibitory stabilized by these anions. Thus, for example, gel-like preparations have helical structures on the basis of micellar cylinders.

I claim:

1. A method for the treatment of a human subject suffering from a bacterial, viral or fungal infection, said method comprising administering to said subject a therapeutically effective amount of a micelle formulation comprising a combination of a pharmaceutically active substance and a compound having the formula

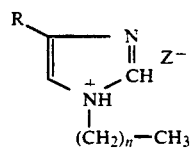

in which:
R is a member selected from the group consisting of H, CH$_3$ and OH;
Z is a member selected from the group consisting of chloride, bromide, iodide, maleate, formate, acetate, propionate, HSO$_4^-$, malate, fumarate, salicylate, alginate, gluconate, glucoronate, galactoronate, ethylsulfate and H$_2$PO$_4^-$; and
n is 8 to 20.

2. A method in accordance with claim 1 in which n is 15.

* * * * *